United States Patent
Imai et al.

(10) Patent No.: US 11,000,037 B2
(45) Date of Patent: May 11, 2021

(54) BENZYLAMIDE COMPOUND, METHOD FOR PRODUCING THE SAME, AND MITICIDE

(71) Applicant: OAT AGRIO CO., LTD., Tokyo (JP)

(72) Inventors: Tetsuya Imai, Rajasthan (IN); Surendra Kumar Kumawat, Rajasthan (IN); Manish Kumar Singh, Rajasthan (IN); Pramod Kumar Chauhan, Rajasthan (IN); Amol Vasant Shelke, Rajasthan (IN); Rajesh Kumar Singh, Rajasthan (IN); Ram Kishore, Rajasthan (IN); Ashish Bhatt, Rajasthan (IN)

(73) Assignee: OAT AGRIO CO., LTD., Tokyo (JP)

( * ) Notice: Subject to any disclaimer, the term of this patent is extended or adjusted under 35 U.S.C. 154(b) by 32 days.

(21) Appl. No.: 16/318,598

(22) PCT Filed: Jul. 14, 2017

(86) PCT No.: PCT/IB2017/054259
§ 371 (c)(1),
(2) Date: Jan. 17, 2019

(87) PCT Pub. No.: WO2018/015852
PCT Pub. Date: Jan. 25, 2018

(65) Prior Publication Data
US 2019/0281824 A1 Sep. 19, 2019

(30) Foreign Application Priority Data
Jul. 18, 2016 (IN) .............................. 201611024522

(51) Int. Cl.
| | | |
|---|---|---|
| A01N 41/10 | (2006.01) | |
| C07C 233/07 | (2006.01) | |
| C07C 327/42 | (2006.01) | |
| C07C 323/41 | (2006.01) | |
| C07D 213/16 | (2006.01) | |
| C07D 239/49 | (2006.01) | |
| C07D 213/56 | (2006.01) | |

(52) U.S. Cl.
CPC ............ *A01N 41/10* (2013.01); *C07C 233/07* (2013.01); *C07C 323/41* (2013.01); *C07C 327/42* (2013.01); *C07D 213/16* (2013.01); *C07D 213/56* (2013.01); *C07D 239/49* (2013.01)

(58) Field of Classification Search
None
See application file for complete search history.

(56) References Cited

U.S. PATENT DOCUMENTS

| | | | | |
|---|---|---|---|---|
| 6,596,772 B1 * | 7/2003 | Huang | .................... | A61P 19/10 |
| | | | | 514/602 |
| 8,536,221 B2 * | 9/2013 | Mortell | .................... | A61P 25/06 |
| | | | | 514/464 |
| 9,067,894 B1 | 6/2015 | Weaver | | |

FOREIGN PATENT DOCUMENTS

| | | |
|---|---|---|
| EP | 3002279 A | 10/2014 |
| JP | 2011042611 | 3/2011 |
| WO | WO2007131680 A1 | 11/2007 |
| WO | WO2012082817 | 6/2012 |
| WO | WO2012176856 A2 | 12/2012 |

OTHER PUBLICATIONS

STN RN 1595101-81-7 Registred Entered STN: May 1, 2014, CN 4-Piperidinecarboxamide, N-[3-[(difluoromethyl)sulfonyl]phenyl]-4-phenyl-, hydrochloride (Year: 2014).*
RN 1590230-75-3 Registryed Entered STN: Apr. 25, 2014 CN Benzeneacetamide, 4-amino-N-[2-methoxy-5-[(trifluoromethyl)sulfonyl]phenyl]-, hydrochloride (Year: 2014).*
RN 1582627-38-0 Registryed Entered STN: Apr. 10, 2014 CN Benzeneacetamide, 2-amino-N-[3-[(difluoromethyl)thio]phenyl]-, hydrochloride (1:1) (Year: 2014).*
RN 1572955-44-2 Registryed Entered STN: Mar. 25, 2014 CN Benzeneacetamide, 4-amino-N-[3-[(difluoromethyl)thio]phenyl]-, hydrochloride (Year: 2014).*
RN 1568845-29-3 Registryed Entered STN: Mar. 14, 2014 CN Benzeneacetamide, 2-amino-N-[3-[(difluoromethyl)sulfonyl]phenyl]-, hydrochloride (Year: 2014).*
STN RN 1568512-39-9 Registryed Entered STN: Mar. 14, 2014 CN Benzeneacetamide, 4-amino-N-[3-[(difluoromethyl)sulfonyl]phenyl] hydrochloride (Year: 2014).*

(Continued)

*Primary Examiner* — Alton N Pryor
(74) *Attorney, Agent, or Firm* — Haley Guiliano LLP; James F. Haley, Jr.; Brian M. Gummow

(57) ABSTRACT

An object of the present invention is to provide a benzylamide compound or a salt thereof that controls a mite. The present invention provides a benzylamide compound represented by Formula (1): or a salt thereof, wherein $R^1$ represents $C_{1-6}$ alkyl or $C_{1-6}$ haloalkyl; $R^2$ and $R^3$ are identical or different and each represent hydrogen, halogen, cyano, nitro, $C_{1-6}$ alkyl, or the like; $R^4$ represents hydrogen, formyl $C_{1-6}$ alkyl, or the like; $R^5$ and $R^6$ are identical or different and each represent hydrogen, halogen, or $C_{1-6}$ alkyl, or the like; $R^7$, $R^8$, $R^9$, $R^{10}$, and $R^{11}$ are identical or different and each represent hydrogen, halogen, or the like; X represents oxygen or sulfur; and n represents an integer of 0 to 2.

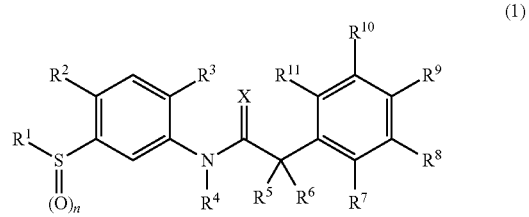

(1)

7 Claims, No Drawings

(56) References Cited

OTHER PUBLICATIONS

STN RN 1390591-78-2 Registryed Entered STN: Aug. 13, 2012 CN Benzeneacetamide, N[3-[(difluoromethyl)sulfonyl]phenyl]-2,5-dimethyl- (Year: 2012).*
STN RN 1390572-95-8 Registryed Entered STN: Aug. 13, 2012 CN 1,4-Benzodioxin-6-acetamide, N-[3-[(difluoromethyl)thio]phenyl]-2,3-dihydro-α,α-dimethyl- (Year: 2012).*
STN RN 1389968-95-9 Registry ED Entered STN: Aug. 12, 2012 CN Benzeneacetamide, N[3-[(difluoromethyl)thio]phenyl]-2,5-dimethyl- (Year: 2012).*
STN RN 1387899-88-8 Registry ED Entered STN: Aug. 8, 2012 CN Cyclobutanecarboxamide, N-[2-methoxy-5-[(trifluoromethyl)sul 1-phenyl- (Year: 2012).*
STN RN 1387780-34-8 Registry ED Entered STN: Aug. 8, 2012 CN Benzeneacetamide, 4-bromo-N-[2-methoxy-5-[(trifluoromethyl)sulfonyl]phenyl]-α,α-dimethyl- (Year: 2012).*
RN 1386956-15-5 Registry ED Entered STN: Aug. 6, 2012 CN 2H-Pyran-4-carboxamide, N-[3-[(difluoromethyl)thio]phenyl]tetrahydro-4-phenyl- (Year: 2012).*
STN RN 1386870-22-9 Registry EE Entered STN: Aug. 6, 2012 CN Benzeneacetamide, N-[3-[(difluoromethyl)thio]phenyl]-4-(trifluorometh (Year: 2012).*
STN RN 1385565-34-3 Registryed Entered STN: Aug. 2, 2012 CN Benzeneacetamide, N-[3-[(difluoromethyl)thio]phenyl]-4-nitro- (Year: 2012).*
STN RN 1385542-78-8 Registry ED Entered STN: Aug. 2, 2012 CN 1,4-Benzodioxin-6-acetamide, 8-chloro-N-[3-[(difluoromethyl)thio]phenyl]-2,3-dihydro- (Year: 2012).*
STN RN 1349051-13-3 Registry ED Entered STN: Dec. 5, 2011 CN 1,4-Benzenediacetannide, N 1[3-[(trifluoronnethyl)sulfonyl]phenyl]-N4-[4-[(trifluoromethyl)sulfonyl]phenyl]- (CA Index Name) MF C24 H18 F6 N2 O6 S2 (Year: 2011).*
STN RN 1318111-23-7 Registry ED Entered STN: Aug. 15, 2011 CN Cyclopropanecarboxamide, 1-(3-bromophenyl)-N-[2-methoxy-5- (Year: 2011).*
STN RN 1317542-56-5 Registry ED Entered STN: Aug. 14, 2011 CN Benzeneacetamide, 4-(acetylamino)-N-[2-methoxy-5-[(trifluoromethyl)sulfonyl]phenyl]- (Year: 2011).*
STN RN 1317541-84-6 Registry ED Entered STN: Aug. 14, 2011 CN 1,4-Benzodioxin-6-acetamide, 2,3-dihydro-N-[2-methoxy-5-[(trifluoromethyl)sulfonyl]phenyl] (Year: 2011).*
STN RN 1317541-82-4 Registry ED Entered STN: Aug. 14, 2011 CN Cyclobutanecarboxannide, 1-(4-chlorophenyl)-N-[2-methoxy-5-[(trifluoromethyl)sulfonyl]phenyl]- (Year: 2011).*
STN RN 1317541-77-7 Registry ED Entered STN: Aug. 14, 2011 CN 2H-Pyran-4-carboxamide, tetrahydro-N-[2-methoxy-5-[(trifluoromethyl)sulfonyl]phenyl]-4-phenyl- (Year: 2011).*
STN RN 1316626-61-5 Registry ED Entered STN: Aug. 12, 2011 CN Cyclopentanecarboxamide, 1-(4-fluorophenyl)-N-[2-methoxy-5-[(trifluoromethyl)sulfonyl]phenyl]- (Year: 2011).*
STN RN 1298842-08-6 Registry ED Entered STN: May 22, 2011CN Benzeneacetamide, 4-ethoxy-N-[2-methoxy-5- (Year: 2011).*
STN RN 1297083-89-6 Registry ED Entered STN: May 19, 2011 CN 2H-1,5-Benzodioxepin-7-acetamide, 9-chloro-3,4-dihydro-N-[2-methoxy-5-[(trifluoromethyl)sulfonyl]phenyl]- (Year: 2011).*
STN RN 1297083-82-9 Registry ED Entered STN: May 19, 2011 CN Cyclobutanecarboxamide, 1-(3-chlorophenyl)-N-[2-methoxy-5-[(trifluoromethyl)sulfonyl]phenyl]- (Year: 2011).*
STN RN 1293617-81-8 Registry ED Entered STN: May 12, 2011 CN Benzeneacetamide, 2,6-dichloro-N-[2-methoxy-5- (Year: 2011).*
STN RN 1293617-71-6 Registry ED Entered STN: May 12, 2011 CN Benzeneacetamide, 3-fluoro-4-methoxy-N-[2-methoxy-5-[(trifluoromethyl)sulfonyl]phenyl]- (Year: 2011).*
STN RN 1290011-93-6 Registry ED Entered STN: May 4, 2011 CN Benzeneacetamide, 3,4-dichloro-N-[2-methoxy-5-[(trifluoromethyl)sulfonyl]phenyl]- (Year: 2011).*
STN RN 1289293-59-9 Registry ED Entered STN: May 3, 2011 CN Benzeneacetamide, N-[2-methoxy-5-[(trifluoromethyl)sulfonyl]phenyl]-4-nitro- (Year: 2011).*
STN RN 1287165-32-5 Registry ED Entered STN: Apr. 28, 2011 CN Benzeneacetamide, 2-fluoro-N-[2-methoxy-5-[(trifluoromethyl)sulfonyl]phenyl]- (Year: 2011).*
STN RN 1278729-49-9 Registry ED Entered STN: Apr. 13, 2011 CN 2-Naphthaleneacetamide, 5,6,7,8-tetrahydro-N-[2-methoxy-5-[(trifluoromethyl)sulfonyl]phenyl]- (Year: 2011).*
STN RN 1278729-42-2 Registry ED Entered STN: Apr. 13, 2011 CN Benzeneacetamide, N-[2-methoxy-5-[(trifluoromethyl)sulfonyl]phenyl]-4-(trifluoromethoxy)- (Year: 2011).*
Borgna et al., "Attivita Inibente La Reazione Di Hill E Fitotossicita Di Fenilacetanilidi α-Sostituite [Action Inhibiting the Hill Reaction and Phytotoxicity of Alpha-Substituted Phenylacetanilides]," Il Farmaco, 28(10):800-810 (1973).
Database Caplus, "Phytotoxicity and inhibition of the Hill Reaction by m-alkylthioailides," (Jan. 1, 1974) (3 pages).
Database Caplus, "Plant growth regulating activities of 2[2-(arylamino)-2-oxoethyl]benzoic acids (part I)," (Jan. 1, 1992) (1 page).
Database Chemcats, "Uorsy Stock Screening Compounds," (May 31, 2016) (1 page).
Database File Registry, "Benzeneacetamide, 4-amino-N-methyl-N-[3-(methylthio)phenyl]-(CA Index Name)," (Apr. 3, 2014) (1 page).
Database File Registry, "Benzoic acid, 3-[2-[methyl[3-(methylthio)phenyl]amino]-2-oxoethyl]-(CA Index Name)," (Mar. 18, 2014) (1 page).
Ramos-Hunter et al., "Discovery and SAR of a novel series of GIRK1/2 and GIRK1/4 activators," Bioorganic & Medicinal Chemistry Letters, 23(18):5195-5198 (2013).
Modena et al., "Plant growth regulating activities of 2-[2-(acylamino)-2-oxoethyl]benzoic acids," Il Farmaco 46(6):825-832 (1991).
Borgna et al., Attivita Inibente La Reazione Di Hill E Fitotossicita Di m-Alchiltioanilidi [Phytotoxicity and inhibition of the Hill reaction by m-alkylthioanilides], Il Farmaco, 28:791-799 (1973).

\* cited by examiner

BENZYLAMIDE COMPOUND, METHOD FOR PRODUCING THE SAME, AND MITICIDE

Cross-Reference To Related Applications

This application is a United States National Phase Application filed under 35 U.S.C. § 371 from International Patent Application No. PCT/IB2017/054259, filed on Jul. 14, 2017, which claims priority from Indian Patent Application No. 201611024522, filed on Jul. 18, 2016. The contents and disclosures of each of these applications are incorporated by reference herein in their entireties.

TECHNICAL FIELD

The present invention relates to a novel benzylamide compound, method for producing the same, and miticide containing the compound.

BACKGROUND ART

Due to the emergence of mites resistant to miticides in recent years as a result of long-term use of miticides, it has become difficult to accomplish control by use of known miticides.

Under such circumstances, there has been an urgent demand for the development of new types of miticides that are expected to achieve excellent miticidal activity.

For example, Patent Literature (PTL) 1 discloses a compound represented by following Formula (A):

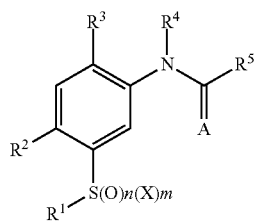

wherein $R^5$ represents substituted or unsubstituted $C_{1-20}$ alkyl, substituted or unsubstituted amino, N-containing heterocycles, or the like, and reports that this compound exhibits miticidal activity.

However, in PTL 1, mainly, urea compounds are produced, and although the amide compounds where $R^5$ is alkyl, haloalkyl, aryl, or cycloalkyl are also produced, no amide compounds where $R^5$ is benzyl is disclosed. In addition, PTL 1 nowhere discloses that the above compound (A) exhibits ovicidal activity.

CITATION LIST

Patent Literature

PTL 1: Japanese Patent Application Laid-open No. 2011-042611

SUMMARY OF INVENTION

Technical Problem

An object of the present invention is to provide a novel benzylamide compound or a salt thereof that exhibits miticidal activity.

Another object of the present invention is to provide a method for producing the benzylamide compound or the salt thereof.

A further object of the present invention is to provide a new type of miticide containing the benzylamide compound or the salt thereof.

Solution to Problem

The present inventors conducted extensive research to achieve the above objects, and succeeded in synthesizing a compound represented by the following Formula (1) or a salt thereof that has miticidal activity. The present inventors have conducted further research based on the above findings. The present invention has thereby been accomplished.

More specifically, the present invention includes the following embodiments:

Item 1:

A benzylamide compound represented by Formula (1):

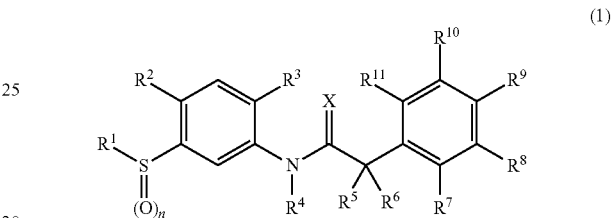

or a salt thereof, wherein $R^1$ represents $C_{1-6}$ alkyl or $C_{1-6}$ haloalkyl;

$R^2$ and $R^3$ are identical or different and each represent hydrogen, halogen, cyano, nitro, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl or $C_{3-8}$ cycloalkyl $C_{1-6}$ alkyl;

$R^4$ represents hydrogen, formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkylcarbonyl, $C_{1-6}$ haloalkylcarbonyl, $C_{1-6}$ alkoxycarbonyl, $C_{1-6}$ haloalkoxycarbonyl, arylcarbonyl, aryloxycarbonyl, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, aryl, aryl $C_{1-6}$ alkyl, arylsulfonyl, arylsulfinyl, arylthio, or heterocyclic, all the substituents defined as $R^4$ may optionally be further substituted;

$R^5$ and $R^6$ are identical or different and each represent hydrogen, halogen, $C_{1-6}$ alkyl, or $C_{1-6}$ haloalkyl; $R^5$ and $R^6$, taken together with the carbon atom, may bond to each other to form a 3- to 8-membered ring, via or not via at least one heteroatom;

$R^7$, $R^8$, $R^9$, $R^{10}$, and $R^{11}$ are identical or different and each represent hydrogen, halogen, nitro, cyano, hydroxyl, formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkylcarbonyl, $C_{1-6}$ haloalkylcarbonyl, arylcarbonyl, aryloxycarbonyl, $C_{1-6}$ alkoxycarbonyl, $C_{1-6}$ haloalkoxycarbonyl, $C_{1-6}$ cyanoalkyl, $C_{1-6}$ cyanoalkoxy, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, $C_{3-8}$ cycloalkylsulfonyl, $C_{3-8}$ cycloalkylsulfinyl, $C_{3-8}$ cycloalkylthio, $C_{3-8}$ cycloalkyl $C_{1-6}$ alkylsulfonyl, $C_{3-8}$ cycloalkyl $C_{1-6}$ alkylsulfinyl, $C_{3-8}$ cycloalkyl $C_{1-6}$ alkylthio, $C_{1-6}$ alkoxy $C_{1-6}$ alkylsulfonyl, $C_{1-6}$ alkoxy $C_{1-6}$ alkylsulfinyl, $C_{1-6}$ alkoxy $C_{1-6}$ alkylthio, $C_{2-6}$ alkenyloxy, $C_{2-6}$ haloalkenyloxy, $C_{2-6}$ alkynyloxy, $C_{2-6}$ haloalkynyloxy, $C_{1-6}$ alkylsulfonyloxy, $C_{1-6}$ haloalkylsulfonyloxy, $C_{1-6}$ alkylsulfinyloxy, $C_{1-6}$ haloalkylsulfinyloxy, carboxyl, OCN, SCN, $SF_5$, substituted or unsubstituted amino, aryl, aryl $C_{1-6}$ alkyl, aryloxy, aryl $C_{1-6}$ alkoxy, arylsulfonyl, arylsulfinyl, arylthio, aryl $C_{1-6}$ alkylsulfonyl, aryl $C_{1-6}$ alkylsulfinyl, aryl $C_{1-6}$ alkylthio, heterocyclic, heterocyclic $C_{1-6}$ alkyl, or heterocyclic oxy, all of which may optionally be further substituted;

$R^7$ and $R^8$, $R^8$ and $R^9$, $R^9$ and $R^{10}$, or $R^{10}$ and $R^{11}$, taken together with the benzene ring to which they bond, may bond to each other to form a 3- to 8-membered ring via or not via at least one heteroatom;

X represents oxygen or sulfur; and n represents an integer of 0 to 2.

Item 2:
The benzylamide compound or the salt thereof according to Item 1, wherein $R^1$ is $C_{1-6}$ haloalkyl.

Item 3:
The benzylamide compound or the salt thereof according to Item 1 or 2, wherein $R^2$ and $R^3$ are identical or different and each represent halogen, cyano, or $C_{1-6}$ alkyl.

Item 4:
The benzylamide compound or the salt thereof according to any one of Items 1 to 3, wherein $R^4$ is hydrogen, or $C_{1-6}$ alkyl.

Item 5:
The benzylamide compound or the salt thereof according to any one of Items 1 to 4, wherein $R^7$, $R^8$, $R^9$, $R^{10}$, and $R^{11}$ are identical or different and each represent hydrogen, halogen, nitro, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, substituted or unsubstituted amino, aryl, or heterocyclic.

Item 6:
The benzylamide compound or the salt thereof according to any one of the preceding items, wherein the benzylamide compound is represented by Formula (1-3):

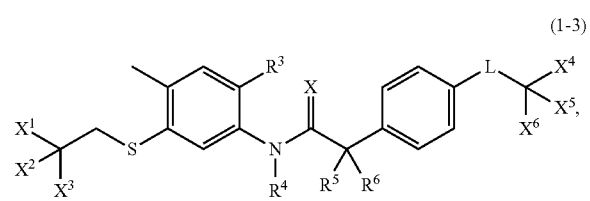

(1-3)

wherein
$R^3$ represents halogen;
$R^4$ represents hydrogen, $C_{1-6}$ alkyl, or $C_{1-6}$ haloalkyl;
$R^5$ and $R^6$ are identical or different and each represent hydrogen or halogen;
X represents O or S;
L represents a single bond, O, or S;
$X^1$, $X^2$, and $X^3$ are identical or different and each represent halogen; and
$X^4$, $X^5$, and $X^6$ are identical or different and each represent hydrogen or halogen.

Item 7:
The benzylamide compound or the salt thereof according to any one of the preceding items, wherein $X^4$, $X^5$, and $X^6$ are identical or different and each represent halogen.

Item 8:
The benzylamide compound or the salt thereof according to any one of the preceding items, wherein $R^5$ and $R^6$ are identical or different and each represent hydrogen, fluorine, chlorine, or bromine.

Item 9:
The benzylamide compound or the salt thereof according to any one of the preceding items, wherein $R^5$ and $R^6$ are identical or different and each represent hydrogen, fluorine, or chlorine.

Item 10:
The benzylamide compound or the salt thereof according to any one of the preceding items, wherein $R^5$ and $R^6$ are identical or different and each represent hydrogen or fluorine.

Item 11:
The benzylamide compound or the salt thereof according to any one of the preceding items, wherein $R^5$ and $R^6$ are hydrogen.

Item 12:
The benzylamide compound or the salt thereof according to any one of the preceding items, wherein $R^4$ represents hydrogen, methyl, or ethyl.

Item 13:
The benzylamide compound or the salt thereof according to any one of the preceding items, wherein L is O or S.

Item 14:
The benzylamide compound or the salt thereof according to any one of the preceding items, wherein X is O.

Item 15:
The benzylamide compound or the salt thereof according to any one of the preceding items, wherein $R^3$ is fluorine, chlorine, or bromine.

Item 16:
The benzylamide compound or the salt thereof according to any one of the preceding items, wherein $R^3$ is fluorine or chlorine.

Item 17:
The benzylamide compound or the salt thereof according to any one of the preceding items, wherein $R^3$ is fluorine.

Item 18:
The benzylamide compound or the salt thereof according to any one of the preceding items, wherein $X^1$, $X^2$, and $X^3$ are identical or different and each represent fluorine, chlorine, or bromine.

Item 19:
The benzylamide compound or the salt thereof according to any one of the preceding items, wherein $X^1$, $X^2$, and $X^3$ are identical or different and each represent fluorine or chlorine.

Item 20:
The benzylamide compound or the salt thereof according to any one of the preceding items, wherein $X^4$, $X^5$, and $X^6$ are identical or different and each represent fluorine, chlorine, or bromine.

Item 21:
The benzylamide compound or the salt thereof according to any one of the preceding items, wherein $X^4$, $X^5$, and $X^6$ are identical or different and each represent fluorine or chlorine.

Item 22:
A benzylamide compound selected from the group consisting of compounds 1A-12, 1A-14, 1A-42, 1A-43, 1A-24, 1A-47, 1A-48, 1A-49, 1A-51, 1A-52, 1A-53, 1A-54, 1A-56, 1A-58, 1A-59, 1A-60, 1A-62, 1A-69, 1A-72, 1A-73, 1A-74, 1A-75, 1A-76, 1A-77, 1A-78, 1A-82, 1A-83, 1A-91, 1A-92, 1A-112, 1A-116, 1A-117, 1A-137, 1A-138, 1B-28, 1B-39, 1B-53, 1B-54, 1B-56, 1B-79, 1B-80, 1B-86, and 1B-87, or a salt thereof.

Item 23:

A benzylamide compound selected from the group consisting of compounds 1A-14, 1A-42, 1A-47, 1A-48, 1A-49, 1A-51, 1A-54, 1A-56, 1A-58, 1A-59, 1A-62, 1A-73, and 1A-75, or a salt thereof.

Item 24:

The benzylamide compound or the salt thereof according to any one of the preceding items, wherein the benzylamide compound is represented by Formula (1-4):

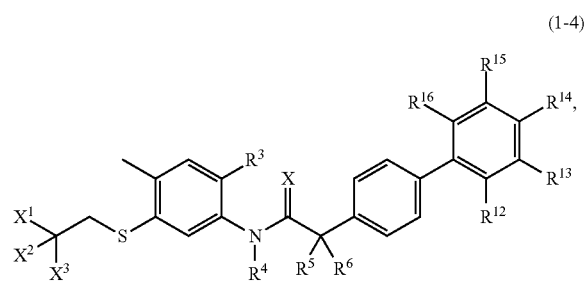

wherein
$R^3$ represents halogen;
$R^4$ represents hydrogen, methyl, or ethyl;
$R^5$ and $R^6$ are identical or different and each represent hydrogen, halogen, $C_{1-6}$ alkyl, or $C_{1-6}$ haloalkyl;
$R^{12}$, $R^{13}$, $R^{14}$, $R^{15}$, and $R^{16}$ are identical or different and each represent hydrogen, halogen, nitro, cyano, hydroxyl, formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkylcarbonyl, $C_{1-6}$ haloalkylcarbonyl, arylcarbonyl, aryloxycarbonyl, $C_{1-6}$ alkoxycarbonyl, $C_{1-6}$ haloalkoxycarbonyl, $C_{1-6}$ cyanoalkyl, $C_{1-6}$ cyanoalkoxy, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, $C_{3-8}$ cycloalkylsulfonyl, $C_{3-8}$ cycloalkylsulfinyl, $C_{3-8}$ cycloalkylthio, $C_{3-8}$ cycloalkyl $C_{1-6}$ alkylsulfonyl, $C_{3-8}$ cycloalkyl $C_{1-6}$ alkylsulfinyl, $C_{3-8}$ cycloalkyl $C_{1-6}$ alkylthio, $C_{1-6}$ alkoxy $C_{1-6}$ alkylsulfonyl, $C_{1-6}$ alkoxy $C_{1-6}$ alkylsulfinyl, $C_{1-6}$ alkoxy $C_{1-6}$ alkylthio, $C_{2-6}$ alkenyloxy, $C_{2-6}$ haloalkenyloxy, $C_{2-6}$ alkynyloxy, $C_{2-6}$ haloalkynyloxy, $C_{1-6}$ alkylsulfonyloxy, $C_{1-6}$ haloalkylsulfonyloxy, $C_{1-6}$ alkylsulfinyloxy, $C_{1-6}$ haloalkylsulfinyloxy, carboxyl, OCN, SCN, $SF_5$, substituted or unsubstituted amino, aryl, aryl $C_{1-6}$ alkyl, aryloxy, aryl $C_{1-6}$ alkoxy, arylsulfonyl, arylsulfinyl, arylthio, aryl $C_{1-6}$ alkylsulfonyl, aryl $C_{1-6}$ alkylsulfinyl, aryl $C_{1-6}$ alkylthio, heterocyclic, heterocyclic $C_{1-6}$ alkyl, or heterocyclic oxy, all of which may optionally be further substituted;
X represents oxygen or sulfur; and
$X^1$, $X^2$, and $X^3$ are identical or different and each represent halogen.

Item 25:

The benzylamide compound or the salt thereof according to any one of the preceding items, wherein $R^3$ is fluorine, chlorine, or bromine.

Item 26:

The benzylamide compound or the salt thereof according to any one of the preceding items, wherein $X^1$, $X^2$, and $X^3$ are identical or different and each represent fluorine, chlorine, or bromine.

Item 27:

The benzylamide compound or the salt thereof according to any one of the preceding items, wherein $R^3$ is fluorine or chlorine.

Item 28:

The benzylamide compound or the salt thereof according to any one of the preceding items, wherein $X^1$, $X^2$, and $X^3$ are identical or different and each represent fluorine or chlorine.

Item 29:

The benzylamide compound or the salt thereof according to any one of the preceding items, wherein $R^3$ is fluorine.

Item 30:

The benzylamide compound or the salt thereof according to any one of the preceding items, wherein $X^1$, $X^2$, and $X^3$ are fluorine.

Item 31:

The benzylamide compound or the salt thereof according to any one of the preceding items, wherein $R^4$ represents hydrogen or methyl.

Item 32:

The benzylamide compound or the salt thereof according to any one of the preceding items, wherein $R^4$ represents hydrogen.

Item 33:

The benzylamide compound or the salt thereof according to any one of the preceding items, wherein $R^5$ and $R^6$ are identical or different and each represent hydrogen or halogen.

Item 34:

The benzylamide compound or the salt thereof according to any one of the preceding items, wherein $R^5$ and $R^6$ each represent hydrogen.

Item 35:

The benzylamide compound or the salt thereof according to any one of the preceding items, wherein $R^{12}$, $R^{13}$, $R^{14}$, $R^{15}$, and $R^{16}$ are identical or different and each represent hydrogen, halogen, cyano, $C_{1-6}$ haloalkyl, $C_{1-6}$ haloalkoxy, or $C_{1-6}$ alkylthio.

Item 36:

A benzylamide compound selected from the group consisting of compounds 1A-27, 1A-28, 1A-29, 1A-63, 1A-65, 1A-66, 1A-67, 1A-68, 1A-93, 1A-94, 1A-95, 1A-96, 1A-102, 1A-103, 1A-104, 1A-105, 1A-106, 1A-107, 1A-108, 1A-109, 1A-110, 1A-111, 1A-113, 1A-114, 1A-118, 1A-119, 1A-120, 1A-121, 1A-122, 1A-123, 1A-124, 1A-125, 1A-127, 1A-128, 1A-140, 1A-141, 1A-142, 1A-143, 1A-144, 1A-145, 1A-146, 1A-147, 1A-148, 1A-149, 1B-4, 1B-5, 1B-6, 1B-11, 1B-12, 1B-13, 1B-14, 1B-15, 1B-16, 1B-17, 1B-18, 1B-19, 1B-20, 1B-21, 1B-26, 1B-27, 1B-29, 1B-30, 1B-31, 1B-32, 1B-33, 1B-34, 1B-35, 1B-37, 1B-38, 1B-40, 1B-41, and 1B-43, or a salt thereof.

Item 37:

A method for producing the benzylamide compound or the salt thereof according to any one of the preceding items, comprising at least one step selected from the group consisting of following steps (d) and (e):

step (d): obtaining a sulfide compound represented by Formula (1-1) by reacting a thiol compound represented by Formula (6) with an alkylating reagent represented by Formula (7):

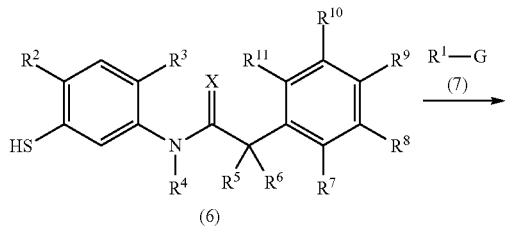

(7)

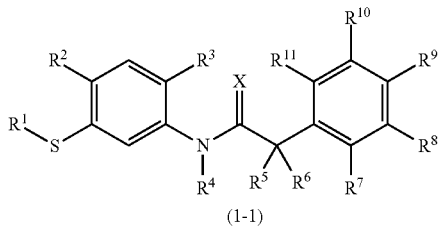

(1-1)

wherein, $R^1$, $R^2$, $R^3$, $R^4$, $R^5$, $R^6$, $R^7$, $R^8$, $R^9$, $R^{10}$, $R^{11}$, and X are as defined above and G represents a leaving group; and step (e): obtaining a benzylamide compound represented by Formula (1-2) by reacting the sulfide compound represented by Formula (1-1) with an oxidizing agent:

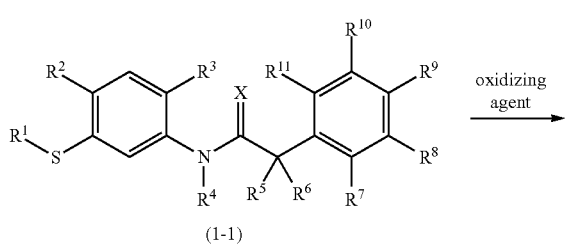

(1-1)

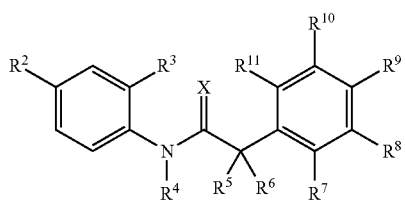

(1-2)

wherein, $R^1$, $R^2$, $R^3$, $R^4$, $R^5$, $R^6$, $R^7$, $R^8$, $R^9$, $R^{10}$, $R^{11}$, and X are as defined above. n' represents 1 or 2.

Item 38:

The method for producing the benzylamide compound and the salt thereof according to any one of the preceding items, further comprising the following step (c):

step (c): obtaining a thiol compound represented by Formula (6) by reacting a sulfonylchloride compound represented by Formula (5) with a reducing agent:

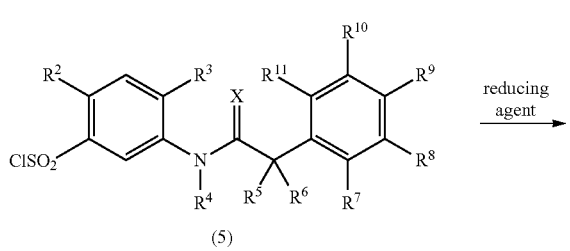

(5)

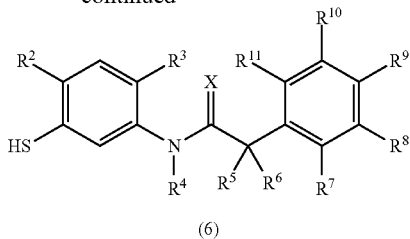

(6)

wherein, $R^2$, $R^3$, $R^4$, $R^5$, $R^6$, $R^7$, $R^8$, $R^9$, $R^{10}$, $R^{11}$, and X are as defined above.

Item 39:

The method for producing the benzylamide compound and the salt thereof according to any one of the preceding items, further comprising the following step (b):

step (b): obtaining the sulfonylchloride compound represented by Formula (5) by chlorosulfonylating an amide compound represented by Formula (4):

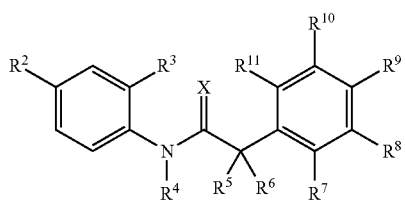

(4)

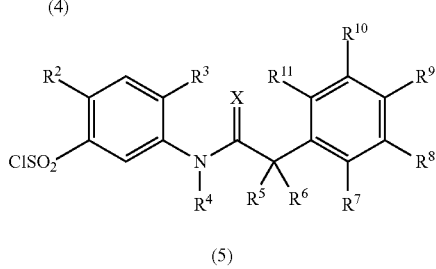

(5)

wherein, $R^2$, $R^3$, $R^4$, $R^5$, $R^6$, $R^7$, $R^8$, $R^9$, $R^{10}$, $R^{11}$, and X are as defined above.

Item 40:

The method for producing the benzylamide compound and the salt thereof according to any one of the preceding items, further comprising the following step (a):

step (a): obtaining the amide compound represented by Formula (4) by reacting an aniline compound represented by Formula (2) with a benzylcarbonyl compound represented by Formula (3):

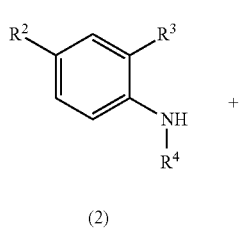

(2)

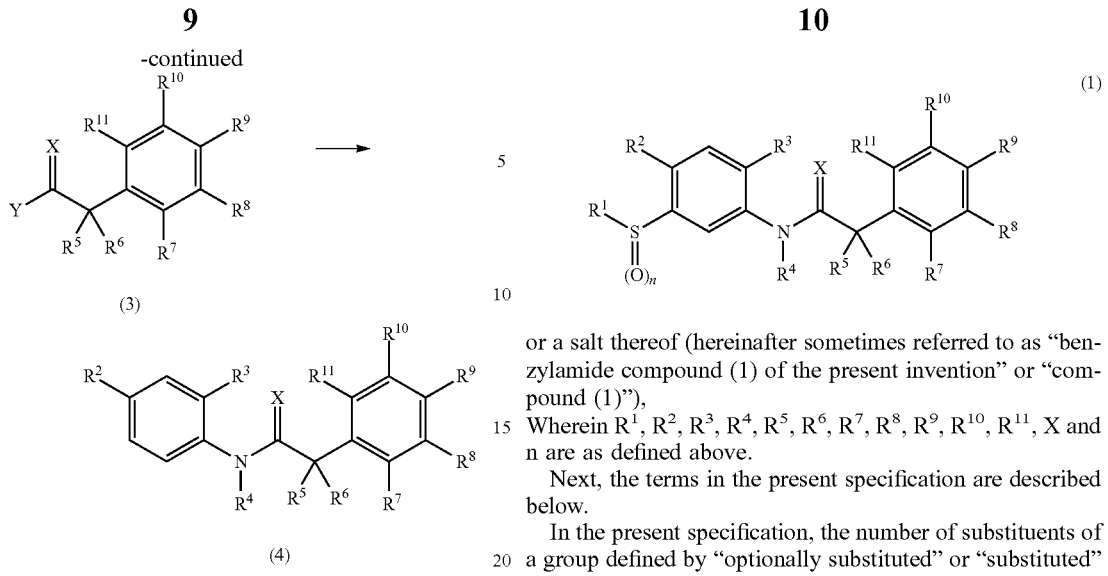

wherein, $R^2$, $R^3$, $R^4$, $R^5$, $R^6$, $R^7$, $R^8$, $R^9$, $R^{10}$, $R^{11}$, and X are as defined above, and Y represents a leaving group or hydroxyl group.

Item 41:

A pesticide containing the benzylamide compound or the salt thereof of according to any one of the preceding items.

Item 42:

A miticide containing the benzylamide compound or the salt thereof of according to any one of the preceding items.

Advantageous Effects of Invention

The benzylamide compound or the salt thereof according to the present invention achieves an excellent miticidal effect with a small amount thereof.

With the present invention, the benzylamide compound and the salt thereof can simply be produced with an excellent yield.

Additionally, with the present invention, a new type of miticide containing the benzylamide compound or the salt thereof according to the present invention can be provided.

DESCRIPTION OF EMBODIMENTS

The present invention is described hereinafter. Throughout the entire specification, a singular expression should be understood as encompassing the concept thereof in the plural form unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

1. Benzylamide Compound or a Salt Thereof

The present invention is directed to a compound represented by Formula (1):

or a salt thereof (hereinafter sometimes referred to as "benzylamide compound (1) of the present invention" or "compound (1)"), Wherein $R^1$, $R^2$, $R^3$, $R^4$, $R^5$, $R^6$, $R^7$, $R^8$, $R^9$, $R^{10}$, $R^{11}$, X and n are as defined above.

Next, the terms in the present specification are described below.

In the present specification, the number of substituents of a group defined by "optionally substituted" or "substituted" is not particularly limited if it is substitutable, and is one or plural. In addition, unless otherwise indicated, the description for each group is also applied when the group is one part of or a substituent on other groups.

"$C_{1-6}$ alkyl" means a linear or branched, saturated hydrocarbon group having one to six carbon atoms.

"$C_{2-6}$ alkenyl" means a linear or branched, unsaturated hydrocarbon group having two to six carbon atoms and containing one to three double bonds.

"$C_{2-6}$ alkynyl" means a linear or branched, unsaturated hydrocarbon group having two to six carbon atoms and containing one triple bond.

"$C_{3-8}$ cycloalkyl" means a cyclic alkyl having three to eight carbon atoms, and includes those cyclic alkyl having a partially bridged structure.

"$C_{1-6}$ alkoxy" refers to a "$C_{1-6}$ alkyloxy group", and the "$C_{1-6}$ alkyl" moiety is defined the same as the above-described "$C_{1-6}$ alkyl".

"Aryl" means a monocyclic or polycyclic aromatic hydrocarbon.

"Heterocyclic" means a saturated, unsaturated, or aromatic heterocyclic group which has at least one of nitrogen, oxygen, phosphorus and/or sulfur atoms in the ring and may be bonded at any substitutable position.

The following shows specific examples of each group as used in this specification.

Examples of halogen include, but are not particularly limited to, fluorine, chlorine, bromine, iodine, and the like.

Examples of $C_{1-6}$ alkyl include, but are not particularly limited to, methyl, ethyl, n-propyl, isopropyl, n-butyl, isobutyl, sec-butyl, tert-butyl, n-pentyl, n-hexyl, and like $C_{1-6}$ straight-chain or branched-chain alkyl.

Examples of $C_{1-6}$ haloalkyl include, but are not particularly limited to, fluoromethyl, chloromethyl, bromomethyl, iodomethyl, difluoromethyl, trifluoromethyl, 2,2,2-trifluoroethyl, pentafluoroethyl, 3,3,3-trifluoropropyl, 4,4,4-trifluorobutyl, heptafluoroisobutyl, and like $C_{1-6}$ straight-chain or branched-chain alkyl substituted with 1 to 9, and preferably 1 to 5, halogen atoms.

Examples of $C_{1-6}$ alkoxy include, but are not particularly limited to, methoxy, ethoxy, n-propoxy, isopropoxy, n-butoxy, isobutoxy, sec-butoxy, tert-butoxy, and like $C_{1-6}$ straight-chain or branched-chain alkoxy.

Examples of $C_{1-6}$ haloalkoxy include, but are not particularly limited to, fluoromethoxy, chloromethoxy, bromomethoxy, iodomethoxy, difluoromethoxy, trifluoromethoxy, 2,2,2-trifluoroethoxy, pentafluoroethoxy, 3,3,3- trifluoropropoxy, 4,4,4-trifluorobutoxy, heptafluoroisobutoxy, and like $C_{1-6}$ straight-chain or branched-chain alkoxy substituted with 1 to 9, preferably 1 to 5, halogen atoms.

Examples of $C_{1-6}$ alkoxy $C_{1-6}$ alkyl include, but are not particularly limited to, methoxymethyl, ethoxymethyl, n-propoxymethyl, isopropoxymethyl, n-butoxymethyl, isobutoxymethyl, sec-butoxymethyl, tert-butoxymethyl, methoxyethyl, ethoxyethyl, methoxy-n-propyl, methoxy-n-butyl, and like alkoxyalkyl in which $C_{1-6}$ straight-chain or branched-chain alkyl is substituted with $C_{1-6}$ straight-chain or branched-chain alkoxy.

Examples of $C_{1-6}$ haloalkoxy $C_{1-6}$ alkyl include, but are not particularly limited to, fluoromethoxymethyl, chloromethoxymethyl, bromomethoxymethyl, iodomethoxymethyl, difluoromethoxymethyl, trifluoromethoxymethyl, 2,2,2-trifluoroethoxymethyl, and like straight-chain or branched-chain alkoxyalkyl substituted with 1 to 9, preferably 1 to 5, halogen atoms.

Examples of $C_{3-8}$ cycloalkyl include, but are not particularly limited to, cyclopropyl, cyclobutyl, cyclopentyl, cyclohexyl, cycloheptyl, cyclooctyl, and the like.

Examples of $C_{3-8}$ cycloalkyl $C_{1-6}$ alkyl include, but are not particularly limited to, cyclopropylmethyl, cyclobutylethyl, cyclopentylmethyl, cyclohexylmethyl, and the like.

Examples of $C_{1-6}$ alkylcarbonyl include, but are not particularly limited to, methylcarbonyl (acetyl), ethylcarbonyl (propionyl), n-propylcarbonyl (butyryl), isopropylcarbonyl (isobutyryl), n-butylcarbonyl (valeryl), isobutylcarbonyl (isovaleryl), sec-butylcarbonyl, tert-butylcarbonyl, and like $C_{1-6}$ straight-chain or branched-chain alkylcarbonyl groups.

Examples of $C_{1-6}$ haloalkylcarbonyl include, but are not particularly limited to, fluoromethylcarbonyl, chloromethylcarbonyl, bromomethylcarbonyl, iodomethylcarbonyl, dichloromethylcarbonyl, trichloromethylcarbonyl, difluoromethylcarbonyl, trifluoromethylcarbonyl, chlorodifluoromethylcarbonyl, bromodifluoromethylcarbonyl, dichlorofluoromethylcarbonyl, 2,2,2-trichloroethylcarbonyl, 2,2,2-trifluoroethylcarbonyl, pentafluoroethylcarbonyl, and like $C_{1-6}$ straight-chain or branched-chain alkylcarbonyl substituted with 1 to 9, and preferably 1 to 5, halogen atoms.

Examples of arylcarbonyl include, but are not particularly limited to, benzoyl, tert-butylbenzoyl, and like substituted or unsubstituted benzoyl group; 1-naphthoyl, 2-naphthoyl, and the like substituted or unsubstituted naphthoyl group.

Examples of aryloxycarbonyl include, but are not particularly limited to, phenoxycarbonyl, 4-diaminophenoxycarbonyl, 4-fluorophenoxycarbonyl, 4-tert-butylphenoxycarbonyl, and like substituted or unsubstituted phenoxycarbonyl group; 1-naphthoxycarbonyl, 2-naphthoxycarbonyl, and the like substituted or unsubstituted naphthoxycarbonyl group.

Examples of $C_{1-6}$ alkoxycarbonyl include, but are not particularly limited to, methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, and like $C_{1-6}$ straight-chain or branched-chain alkoxycarbonyl groups.

Examples of $C_{1-6}$ haloalkoxycarbonyl include, but are not particularly limited to, fluoromethoxycarbonyl, chloromethoxycarbonyl, bromomethoxycarbonyl, iodomethoxycarbonyl, dichloromethoxycarbonyl, trichloromethoxycarbonyl, difluoromethoxycarbonyl, trifluoromethoxycarbonyl, 2,2,2-trifluoroethoxymethyl, pentafluoroethoxycarbonyl, 3,3,3-trifluoropropoxycarbonyl, 4,4,4-trifluorobutoxycarbonyl, heptafluoroisopropoxycarbonyl, and like $C_{1-6}$ straight-chain or branched-chain alkoxycarbonyl substituted with 1 to 9, preferably 1 to 5, halogen atoms.

Examples of cyano $C_{1-6}$ alkyl include, but are not particularly limited to, cyanomethyl, cyanoethyl, cyano-n-propyl, cyano-isopropyl, cyano-n-butyl, cyano-isobutyl, cyano-sec-butyl, cyano-tert-butyl, cyano-n-hexyl, and like $C_{1-6}$ straight-chain or branched-chain alkyl substituted with a cyano group.

Examples of cyano $C_{1-6}$ alkoxy include cyanomethoxy, cyanoethoxy, cyano-n-propoxy, cyano-isopropoxy, cyano-n-butoxy, cyano-iso-butoxy, cyano-sec-butoxy, cyano-tert-butoxy, cyano-hexyloxy, and like $C_{1-6}$ straight-chain or branched-chain alkoxy substituted with a cyano group.

Examples of $C_{2-6}$ alkenyl include, but are not particularly limited to, vinyl, allyl, 2-butenyl, 3-butenyl, 1-methylallyl, and the like.

Examples of $C_{2-6}$ haloalkenyl include, but are not particularly limited to, 2,2-dichlorovinyl, 2,2-dibromovinyl, 2,2-difluorovinyl, 2,2-dibromovinyl, 3,3-difluoro-2-allyl, 4,4-difluoro-3-butenyl, 4,4,4-trifluoro-2-butenyl, and the like.

Examples of $C_{2-6}$ alkynyl include, but are not particularly limited to, ethynyl, 2-propynyl (propargyl), 1-methyl-2-propynyl, 1-butynyl, 2-butynyl, 3-butynyl, and the like.

Examples of $C_{2-6}$ haloalkynyl include, but are not particularly limited to, fluoroethynyl, bromoethynyl, chloroethynyl, iodoethynyl, 3,3,3-trifluoro-1-propynyl, and the like.

Examples of $C_{1-6}$ alkylsulfonyl include, but are not particularly limited to, methylsulfonyl, ethylsulfonyl, n-propylsulfonyl, isopropylsulfonyl, n-butylsulfonyl, isobutylsulfonyl, sec-butylsulfonyl, tert-butylsulfonyl, and like $C_{1-6}$ straight-chain or branched-chain alkylsulfonyl groups.

Examples of $C_{1-6}$ haloalkylsulfonyl include, but are not particularly limited to, fluoromethylsulfonyl, chloromethylsulfonyl, bromomethylsulfonyl, iodomethylsulfonyl, dichloromethylsulfonyl, trichloromethylsulfonyl, difluoromethylsulfonyl, trifluoromethylsulfonyl, chlorodifluoromethylsulfonyl, bromodifluoromethylsulfonyl, dichlorofluoromethylsulfonyl, 2,2,2-trichloroethylsulfonyl, 2,2,2-trifluoroethylsulfonyl, pentafluoroethylsulfonyl, and like $C_{1-6}$ straight-chain or branched-chain alkylsulfonyl substituted with 1 to 9, and preferably 1 to 5, halogen atoms.

Examples of $C_{1-6}$ alkylsulfinyl include, but are not particularly limited to, methylsulfinyl, ethylsulfinyl, n-propylsulfinyl, isopropylsulfinyl, n-butylsulfinyl, isobutylsulfinyl, sec-butylsulfinyl, tert-butylsulfinyl, and like $C_{1-6}$ straight-chain or branched-chain alkylsulfinyl groups.

Examples of $C_{1-6}$ haloalkylsulfinyl include, but are not particularly limited to, fluoromethylsulfinyl, chloromethylsulfinyl, bromomethylsulfinyl, iodomethylsulfinyl, dichloromethylsulfinyl, trichloromethylsulfinyl, difluoromethylsulfinyl, trifluoromethylsulfinyl, chlorodifluoromethylsulfinyl, bromodifluoromethylsulfinyl, dichlorofluoromethylsulfinyl, 2,2,2-trichloroethylsulfinyl, 2,2,2-trifluoroethylsulfinyl, pentafluoroethylsulfinyl, and like $C_{1-6}$ straight-chain or branched-chain alkylsulfinyl substituted with 1 to 9, and preferably 1 to 5, halogen atoms.

Examples of $C_{1-6}$ alkylthio include, but are not particularly limited to, methylthio, ethylthio, n-propylthio, isopropylthio, n-butylthio, isobutylthio, sec-butylthio, tert-butylthio, and like $C_{1-6}$ straight-chain or branched-chain alkylthio.

Examples of $C_{1-6}$ haloalkylthio include, but are not particularly limited to, fluoromethylthio, chloromethylthio, bromomethylthio, iodomethylthio, dichloromethylthio, trichloromethylthio, difluoromethylthio, trifluoromethylthio, chlorodifluoromethylthio, bromodifluoromethylthio, dichlorofluoromethylthio, 2,2,2-trichloroethylthio, 2,2,2-trifluoroethylthio, pentafluoroethylthio, and like $C_{1-6}$ straight-chain or branched-chain alkylthio substituted with 1 to 9, and preferably 1 to 5, halogen atoms.

Examples of $C_{3-8}$ cycloalkylsulfonyl include, but are not particularly limited to, cyclopropylsulfonyl, cyclobutylsulfonyl, cyclopentylsulfonyl, cyclohexylsulfonyl, and the like.

Examples of $C_{3-8}$ cycloalkylsulfinyl include, but are not particularly limited to, cyclopropylsulfinyl, cyclobutylsulfinyl, cyclopentylsulfinyl, cyclohexylsulfinyl, and the like.

Examples of $C_{3-8}$ cycloalkylthio include, but are not particularly limited to, cyclopropylthio, cyclobutylthio, cyclopentylthio, cyclohexylthio, and the like.

Examples of $C_{3-8}$ cycloalkyl $C_{1-6}$ alkylsulfonyl include, but are not particularly limited to, cyclopropylmethylsulfonyl, 2-cyclopropylethylsulfonyl, 3-cyclopropylpropylsulfonyl, cyclohexylmethylsulfonyl, and the like.

Examples of $C_{3-8}$ cycloalkyl $C_{1-6}$ alkylsulfinyl include, but are not particularly limited to, cyclopropylmethylsulfinyl, 2-cyclopropylethylsulfinyl, 3-cyclopropylpropylsulfinyl, cyclohexylmethylsulfinyl, and the like.

Examples of $C_{3-8}$ cycloalkyl $C_{1-6}$ alkylthio include, but are not particularly limited to, cyclopropylmethylthio, 2-cyclopropylethylthio, 3-cyclopropylpropylthio, cyclohexylmethylthio, and the like.

Examples of $C_{1-6}$ alkoxy $C_{1-6}$ alkylsulfonyl include, but are not particularly limited to, methoxymethylsulfonyl, ethoxymethylsulfonyl, n-propoxymethylsulfonyl, isopropoxymethylsulfonyl, n-butoxymethylsulfonyl, sec-butoxymethylsulfonyl, tert-butoxymethylsulfonyl, methoxyethylsulfonyl, and like alkoxyalkylsulfonyl in which $C_{1-6}$ straight-chain or branched-chain alkylsulfonyl is substituted with $C_{1-6}$ straight-chain or branched-chain alkoxy.

Examples of $C_{1-6}$ alkoxy $C_{1-6}$ alkyl sulfinyl include, but are not particularly limited to, methoxymethylsulfinyl, ethoxymethylsulfinyl, n-propoxymethylsulfinyl, isopropoxymethylsulfinyl, n-butoxymethylsulfinyl, sec-butoxymethylsulfinyl, tert-butoxymethylsulfinyl, 2-methoxyethylsulfinyl, and like alkoxyalkylsulfinyl in which $C_{1-6}$ straight-chain or branched-chain alkylsulfinyl is substituted with $C_{1-6}$ straight-chain or branched-chain alkoxy.

Examples of $C_{1-6}$ alkoxy $C_{1-6}$ alkylthio include, but are not particularly limited to, methoxymethylthio, ethoxymethylthio, n-propoxymethylthio, isopropoxymethylthio, n-butoxymethylthio, sec-butoxymethylthio, tert-butoxymethylthio, 2-methoxyethylthio, and like alkoxyalkylthio in which $C_{1-6}$ straight-chain or branched-chain alkylthio is substituted with $C_{1-6}$ straight-chain or branched-chain alkoxy.

Examples of $C_{2-6}$ alkenyloxy include, but are not particularly limited to, vinyloxy, 1-propenyloxy, isopropenyloxy, allyloxy, 2-butenyloxy, 3-butenyloxy, 1-methylallyloxy, and the like.

Examples of $C_{2-6}$ haloalkenyloxy include, but are not particularly limited to, 2,2-dichlorovinyloxy, 2,2-dibromovinyloxy, 2,2-difluorovinyloxy, 2,2-dibromovinyloxy, 3,3-difluoro-2-allyloxy, 4,4-difluoro-3-butenyloxy, 4,4,4-trifluoro-2-butenyloxy, and the like.

Examples of $C_{2-6}$ alkynyloxy include, but are not particularly limited to, ethynyloxy, 2-propynyloxy, 1-methyl-2-propynyloxy, 1,1-dimethyl-2-propynyloxy, 1-butynyloxy, 2-butynyloxy, 3-butynyloxy, and the like.

Examples of $C_{2-6}$ haloalkynyloxy include, but are not particularly limited to, fluoroethynyloxy, bromoethynyloxy, chloroethynyloxy, iodoethynyloxy, 3,3,3-trifluoro-1-propynyloxy, and the like.

Examples of $C_{1-6}$ alkylsulfonyloxy include, but are not particularly limited to, methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, and like $C_{1-6}$ straight-chain or branched-chain alkylsulfonyl groups.

Examples of $C_{1-6}$ haloalkylsulfonyloxy include, but are not particularly limited to, fluoromethylsulfonyloxy, chloromethylsulfonyloxy, bromomethylsulfonyloxy, iodomethylsulfonyloxy, dichloromethylsulfonyloxy, trichloromethylsulfonyloxy, difluoromethylsulfonyloxy, trifluoromethylsulfonyloxy, chlorodifluoromethylsulfonyloxy, bromodifluoromethylsulfonyloxy, dichlorofluoromethylsulfonyloxy, 2,2,2-trichloroethylsulfonyloxy, 2,2,2-trifluoroethylsulfonyloxy, pentafluoroethylsulfonyloxy, and like $C_{1-6}$ straight-chain or branched-chain alkylsulfonyloxy substituted with 1 to 9, and preferably 1 to 5, halogen atoms.

Examples of $C_{1-6}$ alkylsulfinyloxy include, but are not particularly limited to, methylsulfinyloxy, ethylsulfinyloxy, n-propylsulfinyloxy, isopropylsulfinyloxy, n-butylsulfinyloxy, isobutylsulfinyloxy, sec-butylsulfinyloxy, tert-butylsulfinyloxy, and like $C_{1-6}$ straight-chain or branched-chain alkylsulfinyloxy groups.

Examples of $C_{1-6}$ haloalkylsulfinyloxy include, but are not particularly limited to, fluoromethylsulfinyloxy, chloromethylsulfinyloxy, bromomethylsulfinyloxy, iodomethylsulfinyloxy, dichloromethylsulfinyoxy, trichloromethylsulfinyloxy, difluoromethylsulfinyloxy, trifluoromethylsulfinyloxy, chlorodifluoromethylsulfinyloxy, bromodifluoromethylsulfinyloxy, dichlorofluoromethylsulfinyloxy, 2,2,2-trichloroethylsulfinyloxy, 2,2,2-trifluoroethylsulfinyloxy, pentafluoroethylsulfinyloxy, and like $C_{1-6}$ straight-chain or branched-chain alkylsulfinyloxy substituted with 1 to 9, and preferably 1 to 5, halogen atoms.

Examples of substituted or unsubstituted amino include, but are not particularly limited to, amino, monoalkylamino, dialkylamino, monoacylamino, and the like. Examples of the alkyl include $C_{1-6}$ alkyl mentioned above, and the like. Examples of the acyl include $C_{1-6}$ alkoxycarbonyl, haloalkoxycarbonyl, arylcarbonyl mentioned above, and the like.

Examples of aryl include, but are not particularly limited to, phenyl, 1-naphthyl, 2-naphthyl, and the like.

Examples of aryl $C_{1-6}$ alkyl include, but are not particularly limited to, benzyl, phenylethyl, phenyl-n-propyl, and the like.

Examples of aryloxy include, but are not particularly limited to, phenoxy, 1-naphthyloxy, 2-naphthyloxy, and the like.

Examples of aryl $C_{1-6}$ alkoxy include, but are not particularly limited to, benzyloxy, phenoxyethoxy, phenoxy-n-propoxy, phenyl-n-butoxy, 1-naphthylmethoxy, 2-naphthylmethoxy, and like.

Examples of arylsulfonyl include, but are not particularly limited to, phenylsulfonyl, 1-naphthylsulfonyl, 2-naphthylsulfonyl, and the like.

Examples of arylsulfinyl include, but are not particularly limited to, phenylsulfinyl, 1-naphthylsulfinyl, 2-naphthylsulfinyl, and the like.

Examples of arylthio include, but are not particularly limited to, phenylthio, 1-naphthylthio, 2-naphthylthio, and the like.

Examples of aryl $C_{1-6}$ alkylsulfonyl include, but are not particularly limited to, benzylsulfonyl, phenylethylsulfonyl, phenyl-n-propylsulfonyl, phenyl-n-butylsulfonyl, 1-naphthylmethylsulfonyl, 2-naphthylmethylsulfonyl, and the like.

Examples of aryl $C_{1-6}$ alkylsulfinyl include, but are not particularly limited to, benzylsulfinyl, phenylethylsulfinyl, phenyl-n-propylsulfinyl, phenyl-n-butylsulfinyl, 1-naphthylmethylsulfinyl, 2-naphthylmethylsulfinyl, and the like.

Examples of aryl $C_{1-6}$ alkylthio include, but are not particularly limited to, benzylthio, phenylethylthio, phenyl-n-propylthio, phenyl-n-butylthio, 1-naphthylmethylthio, 2-naphthylmethylthio, and the like.

All the Aryls mentioned above may optionally be further substituted. Examples of the number of substituents include, but are not particularly limited to, 1 to 20 (preferably 1 to 10, and more preferably 1 to 5).

Examples of a heterocyclic group include, but are not particularly limited to, thienyl, furyl, tetrahydrofuryl, dioxolanyl, dioxanyl, pyrrolyl, pyrrolinyl, pyrrolidinyl, oxazolyl, isoxazolyl, oxazolinyl, oxazolidinyl, isoxazolinyl, thiazolyl, isothiazolyl, thiazolinyl, thiazolidinyl, isothiazolinyl, pyrazolyl, pyrazolidinyl, imidazolyl, imidazolinyl, imidazolidinyl, oxadiazolyl, oxadiazolinyl, thiadiazolinyl, triazolyl, triazolinyl, triazolidinyl, tetrazolyl, tetrazolinyl, pyridyl, dihydropyridyl, tetrahydropyridyl, piperidyl, oxazinyl, dihydroxazinyl, morpholino, thiazinyl, dihydrothiazinyl, thiamorpholino, pyridazinyl, dihydropyridazinyl, tetrahydropyridazinyl, hexahydropyridazinyl, oxadiazinyl, dihydrooxadiazinyl, tetrahydrooxadiazinyl, thiadiazolyl, thiadiazinyl, dihydrothiadiazinyl, tetrahydrothiadiazinyl, pyrimidinyl, dihydropyrimidinyl, tetrahydropyrimidinyl, hexahydropyrimidinyl, pyrazinyl, dihydropyrazinyl, tetrahydropyrazinyl, piperazinyl, triazinyl, dihydrotriazinyl, tetrahydrotriazinyl, hexahydrotriazinyl, tetrazinyl, dihydrotetrazinyl, indolyl, indolinyl, isoindolyl, indazolyl, quinazolinyl, dihydroquinazolyl, tetrahydroquinazolyl, carbazolyl, benzoxazolyl, benzoxazolinyl, benzisoxazolyl, benzisoxazolinyl, benzothiazolyl, benzisothiazolyl, benzisothiazolinyl, benzimidazolyl, indazolinyl, quinolinyl, dihydroquinolinyl, tetrahydroquinolinyl, isoquinolinyl, dihydroisoquinolinyl, tetrahydroisoquinolinyl, pyridoindolyl, dihydrobenzoxazinyl, cinnolinyl, dihydrocinnolinyl, tetrahydrocinnolinyl, phthalazinyl, dihydrophthalazinyl, tetrahydrophthalazinyl, quinoxalinyl, dihydroquinoxalinyl, tetrahydroquinoxalinyl, purinyl, dihydrobenzotriazinyl, dihydrobenzotetrazinyl, phenothiazinylfuranyl, benzofuranyl, chromanyl, benzothienyl, and the like.

These heterocyclic groups include those substituted at any substitutable position with an oxo or thioketone group.

Examples of heterocyclic $C_{1-6}$ alkyl include, but are not particularly limited to, 2-pyridylmethyl, 3-pyridylmethyl, 2-pyrazinylmethyl, pyrimidinylmethyl, 2-quinolinylmethyl, and the like.

Examples of heterocyclicoxy include, but are not particularly limited to, 2-pyridyloxy, 3-pyridyloxy, 2-pyrazinyloxy, pyrimidinyloxy, 2-quinolinylmethyloxy, and the like.

All the heterocyclics mentioned above may optionally be further substituted. Examples of the number of substituents include, but are not particularly limited to, 1 to 20 (preferably 1 to 10, and more preferably 1 to 5).

$R^5$ and $R^6$, taken together with the carbon atom to which they bond, may bond to each other to form a 3- to 8-membered ring via or not via at least one heteroatom.

Examples of hetero atom in the specification include, but are not particularly limited to, an oxygen atom, a sulfur atom, a nitrogen atom, and the like. Examples of 3- to 8-membered ring include: but are not particularly limited to, cyclopropane, cycloheptane, and the like $C_{3-8}$ cycloalkyl; tetrahydropyran, piperidine, and the like heterocyclic.

$R^7$ and $R^8$, $R^8$ and $R^9$, $R^9$ and $R^{10}$, or $R^{10}$ and $R^{11}$, taken together with the benzene ring to which they bond, may bond to each other to form a 3- to 8-membered ring via or not via at least one heteroatom. Examples of the 3- to 8-membered ring include: $C_{3-8}$ cycloalkyl, aryl, heterocyclic, and the like. The $C_{3-8}$ cycloalkyl, the aryl, and the heterocyclic are as defined above.

Examples of "substituents" for the above substituted groups include: but are not particularly limited to, the halogen, nitro, cyano, hydroxyl, formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkylcarbonyl, $C_{1-6}$ haloalkylcarbonyl, arylcarbonyl, aryloxycarbonyl, $C_{1-6}$ alkoxycarbonyl, $C_{1-6}$ haloalkoxycarbonyl, $C_{1-6}$ cyanoalkyl, $C_{1-6}$ cyanoalkoxy, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, $C_{3-8}$ cycloalkylsulfonyl, $C_{3-8}$ cycloalkylsulfinyl, $C_{3-8}$ cycloalkylthio, $C_{3-8}$ cycloalkyl $C_{1-6}$ alkylsulfonyl, $C_{3-8}$ cycloalkyl $C_{1-6}$ alkylsulfinyl, $C_{3-8}$ cycloalkyl $C_{1-6}$ alkylthio, $C_{1-6}$ alkoxy $C_{1-6}$ alkylsulfonyl, $C_{1-6}$ alkoxy $C_{1-6}$ alkylsulfinyl, $C_{1-6}$ alkoxy $C_{1-6}$ alkylthio, $C_{2-6}$ alkenyloxy, $C_{2-6}$ haloalkenyloxy, $C_{2-6}$ alkynyloxy, $C_{2-6}$ haloalkynyloxy, $C_{1-6}$ alkylsulfonyloxy, $C_{1-6}$ haloalkylsulfonyloxy, $C_{1-6}$ alkylsulfinyloxy, $C_{1-6}$ haloalkylsulfinyloxy, carboxyl, OCN, SCN, $SF_5$, substituted or unsubstituted amino, aryl, aryl $C_{1-6}$ alkyl, aryloxy, aryl $C_{1-6}$ alkoxy, arylsulfonyl, arylsulfinyl, arylthio, aryl $C_{1-6}$ alkylsulfonyl, aryl $C_{1-6}$ alkylsulfinyl, aryl $C_{1-6}$ alkylthio, heterocyclic, heterocyclic $C_{1-6}$ alkyl, heterocyclic oxy, and the like. Of these, preferable substituents are halogen, nitro, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, substituted or unsubstituted amino, aryl, and heterocyclic, and more preferable substituents are fluorine, chlorine, nitro, methyl, ethyl, trifluoromethyl, methoxy, and trifluoromethoxy.

Preferable substituted aryl groups are halogen-substituted aryl, $C_{1-6}$ alkyl-substituted aryl, $C_{1-6}$ haloalkyl-substituted aryl, halogen and $C_{1-6}$ haloalkyl-substituted aryl, $C_{1-6}$ alkoxy-substituted aryl, $C_{1-6}$ haloalkoxy-substituted aryl, and $C_{1-6}$ alkylthio-substituted aryl. More preferable substituted aryl groups are chlorine-substituted aryl, fluorine-substituted aryl, trifluoromethyl-substituted aryl, chlorine- and trifluoromethyl-substituted aryl, trifluoromethoxy-substituted aryl, and methoxy-substituted aryl, and methylthio-substituted aryl.

Preferable substituted heterocyclic groups are halogen-substituted heterocyclic, $C_{1-6}$ alkyl-substituted heterocyclic, $C_{1-6}$ haloalkyl-substituted heterocyclic, $C_{1-6}$ alkoxy-substituted heterocyclic, $C_{1-6}$ haloalkoxy-substituted heterocyclic, and $C_{1-6}$ alkylthio-substituted heterocyclic. More preferable substituted heterocyclic groups are chlorine-substituted heterocyclic, fluorine-substituted heterocyclic, trifluoromethyl-substituted heterocyclic, trifluoromethoxy-substituted heterocyclic, methoxy-substituted heterocyclic, and methylthio-substituted heterocyclic.

The salts of the compounds represented by Formula (1) may be any type of salts as long as they are agriculturally acceptable. Examples of the salts include a hydrochloride salt, a sulfate salt, a nitrate salt, and like inorganic acid salts; an acetate salt, a methanesulfonic acid salt, and like organic acid salts; a sodium salt, a potassium salt, and like alkali metal salts; a magnesium salt, a calcium salt, and like alkaline earth metal salts; dimethylammonium, triethylammonium, and like quaternary ammonium salts; and the like.

X represents oxygen or sulfur.

Symbol n represents an integer of 0 to 2.

Among compounds (1) of the present invention, a preferable compound is a compound in which $R^1$ is $C_{1-6}$ haloalkyl, and a more preferable compound (1) is a compound in which $R^1$ is trifluoromethyl or trifluoroethyl.

Among compounds (1) of the present invention, a preferable compound is a compound in which $R^2$ is hydrogen, halogen, or $C_{1-6}$ alkyl, and a more preferable compound (1) is a compound in which $R^2$ is fluorine, chlorine, bromine, or methyl.

Among compounds (1) of the present invention, a preferable compound is a compound in which $R^3$ is hydrogen, halogen, or $C_{1-6}$ alkyl, and a more preferable compound (1) is a compound in which $R^3$ is fluorine, chlorine, bromine, methyl or trifluoromethyl.

Among compounds (1) of the present invention, a preferable compound is a compound in which $R^4$ is hydrogen, $C_{1-6}$ alkyl, $C_{2-6}$ alkenyl, $C_{2-6}$ alkynyl, or $C_{1-6}$ haloalkyl, and a more preferable compound (1) is a compound in which $R^4$ is hydrogen, methyl, ethyl, n-propyl, n-butyl, 3,3,3-trifluoro-n-propyl, heptafluoroisopropyl, or propargyl.

Among compounds (1) of the present invention, a preferable compound is a compound in which $R^5$ and $R^6$ are identical or different and each represent hydrogen, halogen, or $C_{1-6}$ alkyl, and a more preferable compound (1) is a compound in which $R^5$ and $R^6$ are hydrogen, fluorine, methyl, isopropyl, or tert-butyl.

Among compounds (1) of the present invention, a preferable compound is a compound in which $R^7$, $R^8$, $R^9$, $R^{10}$, and $R^{11}$ are hydrogen, halogen, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, substituted or unsubstituted amino, substituted or unsubstituted aryl, substituted or unsubstituted heterocyclic, or substituted or unsubstituted heterocyclic oxy; a more preferable compound is a compound in which $R^7$, $R^8$, $R^9$, $R^{10}$, and $R^{11}$ are hydrogen, halogen, nitro, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, substituted or unsubstituted amino, substituted or unsubstituted aryl, or substituted or unsubstituted heterocyclic; and a further more preferable compound (1) is a compound in which $R^7$, $R^8$, $R^9$, $R^{10}$, and $R^{11}$ are hydrogen, fluorine, chlorine, bromine, nitro, methyl, ethyl, n-propyl, isopropyl, tert-butyl, n-pentyl, trifluoromethyl, methoxy, ethoxy, n-propoxy, trifluoromethoxy, trifluoromethylsulfonyl, trifluoromethylthio, methylsulfonyl, methylthio, $NH_2$, phenyl, 2-chlorophenyl, 4-chlorophenyl, 3,4-dichlorophenyl, 2-fluorophenyl, 3-fluorophenyl, 4-fluorophenyl, 3,5-difluorophenyl, 2-chloro-4-fluorophenyl, 2-trifluoromethylphenyl, 3-trifluoromethylphenyl, 4-trifluoromethylphenyl, 3-chloro-5-trifluoromethylphenyl, 4-chloro-3-trifluoromethylphenyl, 2-trifluoromethoxyphenyl, 3-trifluoromethoxyphenyl, 4-trifluoromethoxyphenyl, 4-methoxyphenyl, 2-methylthiophenyl, 5-trifluoromethyl-2-pyridyl, or 5-pyrimidyl, ethylthio, n-propylthio, isopropylthio, difluoromethylthio, 4-phenylphenyl, 4-cyanophenyl, 3-chlorophenyl, 2,3,4-trichlorophenyl, 3-trifluoromethoxyphenyl, 2,2,2-trifluoroethylthio, 2-(methylthio)-phenyl, 2,3-dichlorophenyl, 2,3,4-trifluorophenyl, 2,4-dichlorophenyl, 2,5-dichlorophenyl, 3, 4-difluorophenyl, 3-(benzo[d][1,3]dioxol-5-yl)phenyl, 3,5-dichlorophenyl, 4-(ethylthio)-phenyl, 4-acetylphenyl, or 4-(dimethylamino)-phenyl.

Alternatively, among compounds (1) of the present invention, a preferable compound is a compound in which $R^1$ is $—CH_2C(X^1)(X^2)(X^3)$ wherein $X^1$, $X^2$, and $X^3$ are identical or different and each represent halogen; a more preferable compound (1) is a compound in which $X^1$, $X^2$, and $X^3$ are identical or different and each represent fluorine, chlorine, or bromine; a further more preferable compound (1) is a compound in which $X^1$, $X^2$, and $X^3$ are identical or different and each represent fluorine or chlorine; and a most preferable compound (1) is a compound in which $X^1$, $X^2$, and $X^3$ are fluorine.

Among compounds (1) of the present invention, a preferable compound is a compound in which $R^2$ is methyl.

Among compounds (1) of the present invention, a preferable compound is a compound in which $R^3$ is halogen; a more preferable compound is a compound in which $R^3$ is fluorine, chlorine, or bromine; a further more preferable compound is a compound in which $R^3$ is fluorine or chlorine; and a most preferable compound is a compound in which $R^3$ is fluorine.

Among compounds (1) of the present invention, a preferable compound is a compound in which $R^4$ is hydrogen, $C_{1-6}$ alkyl, or $C_{1-6}$ haloalkyl; a more preferable compound (1) is a compound in which $R^4$ is hydrogen, methyl, or ethyl; a more preferable compound (1) is a compound in which $R^4$ is hydrogen or methyl; and a most preferable compound (1) is a compound in which $R^4$ is hydrogen.

Among compounds (1) of the present invention, a preferable compound is a compound in which $R^5$ and $R^6$ are hydrogen or halogen; a more preferable compound is a compound in which $R^5$ and $R^6$ are identical or different and each represent hydrogen, fluorine, chlorine, or bromine; a further more preferable compound is a compound in which $R^5$ and $R^6$ are identical or different and each represent hydrogen, fluorine, or chlorine; a still further more preferable compound is a compound in which $R^5$ and $R^6$ are identical or different and each represent hydrogen or fluorine; and a most preferable compound (1) is a compound in which $R^5$ and $R^6$ are hydrogen.

Among compounds (1) of the present invention, a preferable compound is a compound in which $R^7$, $R^8$, $R^{10}$, and $R^{11}$ are hydrogen.

Among compounds (1) of the present invention, a preferable compound is a compound in which $R^9$ is $-L-CH_2—C(X^4)(X^5)(X^6)$ wherein L is a single bond, oxygen, or sulfur and $X^4$, $X^5$, and $X^6$ are identical or different and each represent hydrogen or halogen; a more preferable compound (1) is a compound in which L is oxygen or sulfur and $X^4$, $X^5$, and $X^6$ are identical or different and each represent halogen; a further more preferable compound (1) is a compound in which L is oxygen or sulfur and $X^4$, $X^5$, and $X^6$ are identical or different and each represent fluorine, chlorine, or bromine; and a still further more preferable compound (1) is a compound in which L is oxygen or sulfur and $X^4$, $X^5$, and $X^6$ are identical or different and each represent fluorine or chlorine.

Among compounds (1) of the present invention, a preferable compound is a compound in which X is oxygen or sulfur, and a more preferable compound (1) is a compound in which X is oxygen.

Among compounds (1) of the present invention, a preferable compound is a compound in which n is 0.

Among compounds (1) of the present invention, a preferable compound is a compound in which $R^7$, $R^8$, $R^{10}$, and $R^{11}$ are hydrogen and $R^9$ is a group of the formula:

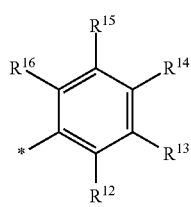

wherein * is the point of attachment to the carbon adjacent to $R^9$; $R^{12}$, $R^{13}$, $R^{14}$, $R^{15}$, and $R^{16}$ are hydrogen, halogen, nitro, cyano, hydroxyl, formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkylcarbonyl, $C_{1-6}$ haloalkylcarbonyl, arylcarbonyl, aryloxycarbonyl, $C_{1-6}$ alkoxycarbonyl, $C_{1-6}$ haloalkoxycarbonyl, $C_{1-6}$ cyanoalkyl, $C_{1-6}$ cyanoalkoxy, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, $C_{3-8}$ cycloalkylsulfonyl, $C_{3-8}$ cycloalkylsulfinyl, $C_{3-8}$ cycloalkylthio, $C_{3-8}$ cycloalkyl $C_{1-6}$ alkylsulfonyl, $C_{3-8}$ cycloalkyl $C_{1-6}$ alkylsulfinyl, $C_{3-8}$ cycloalkyl $C_{1-6}$ alkylthio, $C_{1-6}$ alkoxy $C_{1-6}$ alkylsulfonyl, $C_{1-6}$ alkoxy $C_{1-6}$ alkylsulfinyl, $C_{1-6}$ alkoxy $C_{1-6}$ alkylthio, $C_{2-6}$ alkenyloxy, $C_{2-6}$ haloalkenyloxy, $C_{2-6}$ alkynyloxy, $C_{2-6}$ haloalkynyloxy, $C_{1-6}$ alkylsulfonyloxy, $C_{1-6}$ haloalkylsulfonyloxy, $C_{1-6}$ alkylsulfinyloxy, $C_{1-6}$ haloalkylsulfinyloxy, carboxyl, OCN, SCN, $SF_5$, substituted or unsubstituted amino, aryl, aryl $C_{1-6}$ alkyl, aryloxy, aryl $C_{1-6}$ alkoxy, arylsulfonyl, arylsulfinyl, arylthio, aryl $C_{1-6}$ alkylsulfonyl, aryl $C_{1-6}$ alkylsulfinyl, aryl $C_{1-6}$ alkylthio, heterocyclic, heterocyclic $C_{1-6}$ alkyl, or heterocyclic oxy, all of which may optionally be further substituted; a more preferable compound is a compound in which $R^{12}$, $R^{13}$, $R^{14}$, $R^{15}$, and $R^{16}$ are identical or different and each represent hydrogen, halogen, cyano, $C_{1-6}$ haloalkyl, $C_{1-6}$ haloalkoxy, or $C_{1-6}$ alkylthio; and a further more preferable compound is a compound in which $R^9$ is phenyl, 2-fluorophenyl, 2-chlorophenyl, 2-trifluoromethoxyphenyl, 2-(methylthio)phenyl, 2,3-dichlorophenyl, 2,4-dichlorophenyl, 2-chloro-4-fluoro-phenyl, 2,3,4-trifluorophenyl, 2,3,4-trichlorophenyl, 3-fluorophenyl, 3-chlorophenyl, 3-trifluoromethylphenyl, 3-trifluoromethoxyphenyl, 3,4-difluorophenyl, 3,4-dichlorophenyl, 3,5-difluorophenyl, 3,5-dichlorophenyl, 3-trifluoromethyl-4-chloro-phenyl, 3-chloro-5-trifluoromethyl-phenyl, 3,4,5-trifluorophenyl, 4-fluorophenyl, 4-chlorophenyl, 4-bromophenyl, 4-methylphenyl, 4-methoxyphenyl, 4-trifluoromethylphenyl, 4-trifluoromethoxyphenyl, 4-cyanophenyl, 4-phenylphenyl, 4-acetylphenyl, 4-(dimethylamino)phenyl, 4-(methylthio)phenyl, or 4-(ethylthio)phenyl.

When the compound (1) has isomers such as optical isomers, stereoisomers, regioisomers, and the like, any of the isomers and mixtures thereof are included within the scope of the compound (1). For example, when the compound (1) has optical isomers, the optical isomer separated from a racemic body is also included within the scope of the compound (1). Each of such isomers may be obtained as a single compound by known synthesis and separation means (e.g., concentration, solvent extraction, column chromatography, recrystallization, etc.).

2. Method for Producing a Benzylamide Compound and a Salt Thereof

No limitations are placed on the method for producing a benzylamide compound (1) (compound (1-1) and compound (1-2)) according to the present invention, and the benzylamide compound (1) can be produced by Steps 1 to 5 represented by Reaction Scheme 1 below:

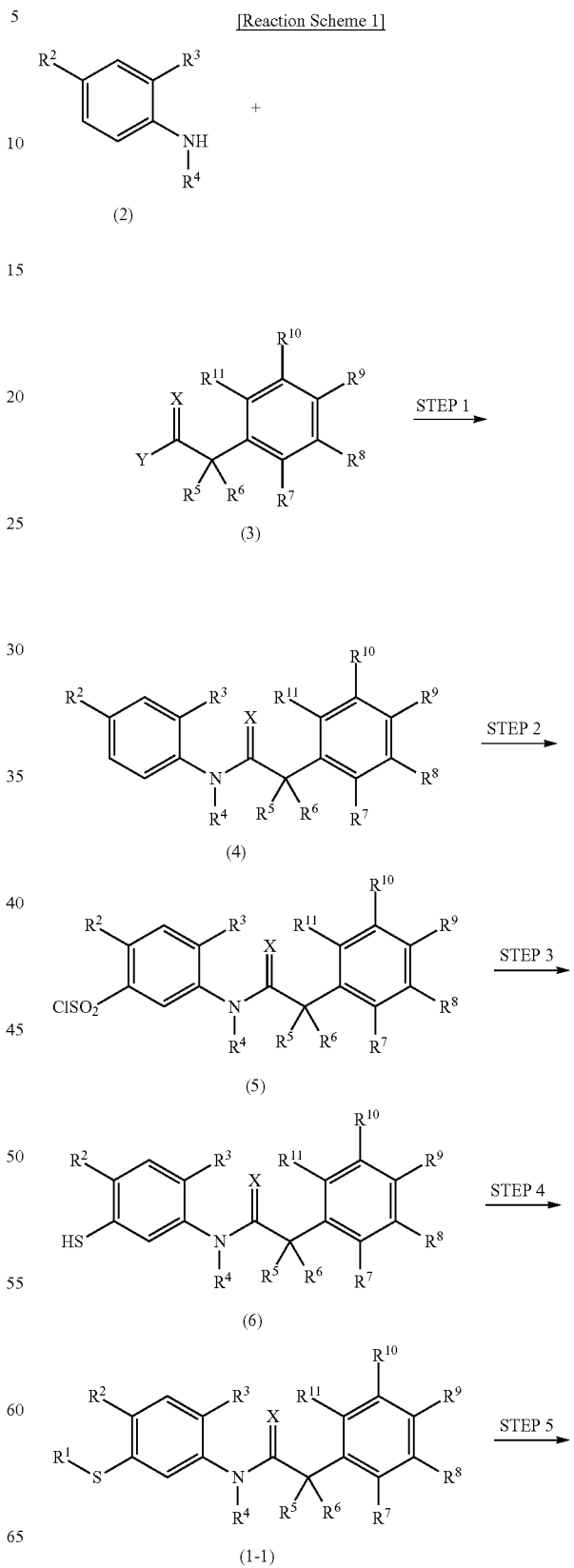

-continued

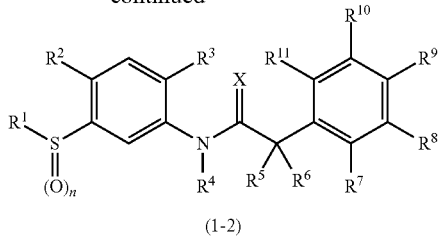

(1-2)

wherein $R^1$, $R^2$, $R^3$, $R^4$, $R^5$, $R^6$, $R^7$, $R^8$, $R^9$, $R^{10}$, $R^{11}$, X, and n are as defined above.

Step 1

An amide compound (hereinafter may be referred to as "compound (4)") represented by Formula (4) can be produced by reacting an aniline compound (hereinafter may be referred to as "compound (2)") represented by Formula (2)) with a benzylcarbonyl compound (hereinafter may be referred to as "compound (3)") represented by Formula (3) (Reaction Scheme 2):

[Reaction Scheme 2]

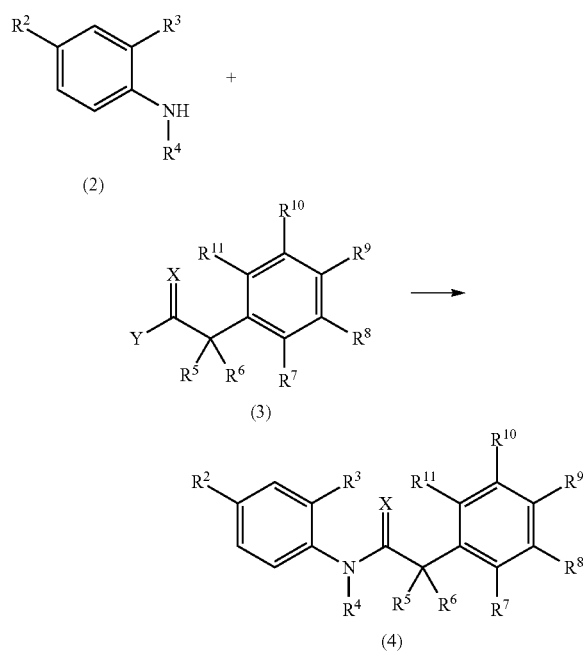

wherein $R^2$, $R^3$, $R^4$, $R^5$, $R^6$, $R^7$, $R^8$, $R^9$, $R^{10}$, $R^{11}$, X are as defined above.

Y represents a leaving group or a hydroxyl group, and examples of the leaving group include: halogen such as chlorine, bromine, and iodine; substituted or unsubstituted $C_{1-6}$ alkyl sulfonate; and substituted or unsubstituted aryl sulfonate. Examples of the substituent include the aforementioned substituents such as the halogen and the $C_{1-6}$ haloalkyl.

Step 1A (when Y is a Leaving Group)

A phenylacetamide compound (hereinafter may be referred to as "compound (4)") represented by Formula (4) can be produced by reacting the aniline compound (hereinafter may be referred to as "compound (2)") represented by Formula (2)) with a benzylcarbonyl compound (hereinafter may be referred to as "compound (3A) represented by Formula (3A) (Reaction Scheme 3):

[Reaction Scheme 3]

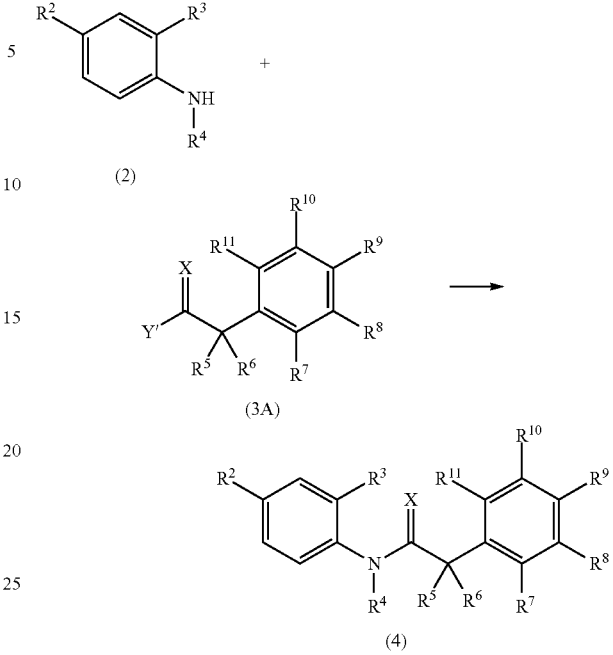

wherein $R^2$, $R^3$, $R^4$, $R^5$, $R^6$, $R^7$, $R^8$, $R^9$, $R^{10}$, $R^{11}$, and X are as defined above. Y' represents a leaving group.

Examples of the benzylcarbonyl compound (3A) include, but are not particularly limited to, phenylacetyl chloride, phenylacetyl bromide, and the like substituted or unsubstituted phenylacetyl halide; and ethyl phenylacetate, methyl phenylacetate, and the like substituted or unsubstituted phenylacetic acid esters.

A used ratio of the aniline compound (2) and the benzylcarbonyl compound (3A) in the reaction therebetween is not particularly limited and thus can appropriately be selected from a wide range. Relative to 1 mole of the aniline compound (2), typically approximately 1 to 5 moles of the benzylcarbonyl compound (3A) and preferably approximately equimolar to 1.2 moles thereof is used.

The aforementioned reaction can be performed under absence or presence of a base. Among the above, the reaction is performed preferably under the presence of the base. As the base, a conventionally known base can widely be used, and examples of the base include: sodium carbonate, potassium carbonate, cesium carbonate, potassium bicarbonate, sodium bicarbonate, and the like alkali metal carbonates; sodium hydroxide, potassium hydroxide, and the like alkali metal hydroxides; alkali metal hydrides such as sodium hydride and potassium hydride, and the like inorganic bases; sodium methoxide, sodium ethoxide, potassium tert-butoxide, and the like alkali metal alkoxides; pyridine, triethylamine, diethylamine, dimethylamine, methylamine, imidazole, benzimidazole, diisopropylethylamine, 4-dimethylamine pyridine, piperidine, and the like organic bases; and the like. Any separate one of these bases or a combination of two or more types thereof is used.

Relative to 1 mole of the aniline compound (2), typically approximately 1 to 10 moles of the base and preferably approximately 1 to 5 moles thereof may excessively be used. When triethylamine, pyridine, or like an organic base is used, it can be used in large excess to serve also as a reaction solvent.

The aforementioned reaction is performed in an appropriate solvent or without any solvent. When the aforementioned reaction is carried out in the solvent, no limitations are placed on the solvent as long as the solvent is inactive with respect to the aforementioned reaction. Examples of such a solvent include: n-hexane, cyclohexane, n-heptane, and the like fatty acid or alicyclic hydrocarbon-based solvents; benzene, chlorobenzene, toluene, xylene, and the like aromatic hydrocarbon-based solvents; methylene chloride, 1,2-dichloroethane, chloroform, and carbon tetrachloride, and the like halogenated hydrocarbon-based solvents; diethyl ether, tetrahydrofuran (THF), 1,4-dioxane, and the like ether-based solvents; methyl acetate, ethyl acetate, and the like esters solvents; acetonitrile; N,N-dimethylformamide (DMF) and the like amide-based solvents; and dimethyl sulfoxide and the like sulfoxide-based solvents. Any one of these solvents can be used alone or a combination of two or more types thereof can be used when necessary.

Reaction temperature for the aforementioned reaction is not particularly limited, and is typically within a range between −10° C. and a boiling point of the solvent used and preferably 0 to 25° C. Reaction time varies depending on, for example, the reaction temperature, and the reaction typically ends in approximately 0.5 to 24 hours.

Step 1B (when Y is a Hydroxyl Group)

As another method for obtaining the phenylacetamide compound (4), the compound (4) can be produced by reacting the aniline compound (2) with a phenylacetic acid compound (hereinafter may be referred to as "compound (3B)") represented by Formula (3B) (Reaction Scheme 4):

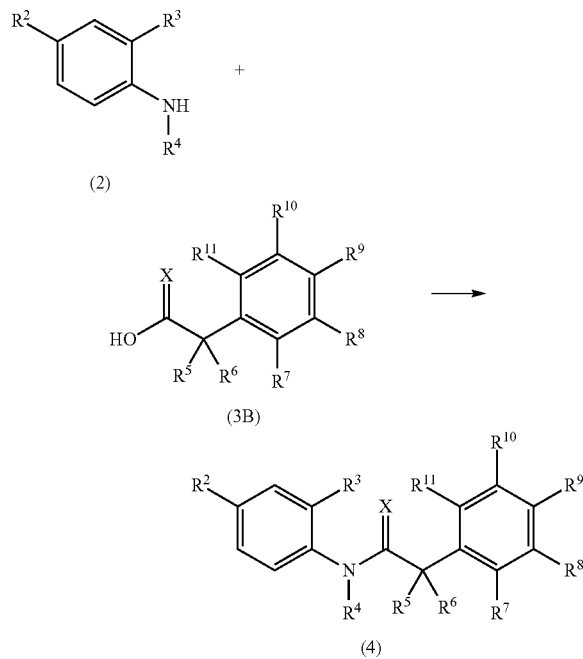

[Reaction Scheme 4]

wherein $R^2$, $R^3$, $R^4$, $R^5$, $R^6$, $R^7$, $R^8$, $R^9$, $R^{10}$, $R^{11}$, and X are as defined above.

A used ratio of the aniline compound (2) and the phenylacetic acid compound (3B) in the reaction therebetween is not particularly limited and thus can appropriately be selected from a wide range. Relative to 1 mole of the aniline compound (2), typically approximately 1 to 5 moles of the phenylacetic acid compound (3B) and preferably approximately equimolar to 1.2 moles thereof is used.

The aforementioned reaction can be performed under absence or presence of a condensing agent. Among the above, the aforementioned reaction is preferably performed under the presence of the condensing agent. As the condensing agent, a conventionally known condensing agent can be used, and examples of the condensing agent include 1-ethyl-3-(3-dimethylaminopropyl) carbodiimide (EDCI HCl), 1-hydroxybenzotriazole (HOBT), 1-[bis(dimethylamino)methylene]-1H-1,2,3-triazolo [4, 5-b] pyridinium-3-oxide hexafluorophosphate (HATU), bis (2-oxo-3-oxazolidinyl) phosphine acid chloride (BOP-Cl), propylphosphonic acid anhydride (T3P), and the like. Any separate one of these condensing agents or a combination of two or more types thereof is used.

Relative to 1 mole of the aniline compound (2), typically 1 to 10 moles of the condensing agent and preferably approximately 1 to 3 moles thereof can excessively be used.

The aforementioned reaction is performed in an appropriate solvent or without any solvent. When the aforementioned reaction is carried out in the solvent, no limitations are placed on the solvent as long as the solvent is inactive with respect to the aforementioned reaction. Examples of such a solvent include: fatty n-hexane, cyclohexane, n-heptane, and the like acid or alicyclic hydrocarbon-based solvents; benzene, chlorobenzene, toluene, xylene, and the like aromatic hydrocarbon-based solvents; methylene chloride, 1,2-dichloroethane, chloroform, carbon tetrachloride, and the like halogenated hydrocarbon-based solvents; diethyl ether, THF, and 1,4-dioxane, and the like ether-based solvents; methyl acetate, ethyl acetate, and the like esters solvents; acetonitrile; DMF and the like amide solvents; and dimethyl sulfoxide and the like sulfoxide-based solvents. Any one of these solvents can be used alone or a combination of two or more types of the solvents can be used when necessary.

Reaction temperature for the aforementioned reaction is not particularly limited and is typically within a range between −10° C. and a boiling point of the solvent used and preferably within a range between −5° C. and the boiling point of the solvent. Reaction time varies depending on, for example, the reaction temperature, and the reaction typically ends in approximately 0.25 to 24 hours.

Step 1C

Note that as a method for producing the phenylacetamide compound (4), a phenylacetic acid halide compound (3C) obtained by reacting the phenylacetic acid compound (3B) with a halogenation reagent can be used as a raw material.

The aforementioned reaction can be performed under presence of a base. As the base, any of the same bases as those described above can be used, and preferable examples of the base include triethylamine, pyridine, di-isopropylamine, 4-diisopropylethylamine, 4-dimethylamine pyridine, lutidine, and the like organic bases, and this base can also much excessively be used to be also used as a reaction solvent.

Examples of the halogenation reagent includes, but are not particularly limited to, $POCl_3$, $POBr_3$, $SOCl_2$, $SO_2Cl_2$, oxalyl chloride.

Relative to 1 mole of the aniline compound (2), typically 1 to 10 moles of the halogenation reagent and preferably approximately 1 to 5 moles thereof can be used.

The aforementioned reaction is performed in an appropriate solvent or without any solvent. When the aforementioned reaction is carried out in the solvent, no limitations are placed on the solvent as long as the solvent is inactive with respect to the aforementioned reaction. As such a solvent, the aforementioned solvents are listed. Any one of these solvents can be used alone or a combination of two or more types thereof can be used when necessary.

Reaction temperature for the aforementioned reaction is not particularly limited and is typically within a range between −10° C. and a boiling point of the solvent used and preferably within a range between −5° C. and the boiling point of the solvent. Reaction time varies depending on, for example, the reaction temperature, and the reaction typically ends in approximately 0.25 to 24 hours.

The aniline compound (2), the benzylcarbonyl compound (3A), the phenylacetic acid compound (3B), and phenylacetic acid halide compound (3C) in Step 1 used as starting materials in Step 1 are known compounds or compounds that can easily be produced by a known method.

The compound (4) obtained by the method shown in Step 1 is easily isolated from a reaction mixture to be purified by use of typical isolation means and purification means, for example, filtration, solvent extraction, distillation, recrystallization, column chromatography, etc.

After end of the reaction, the compound (4) can be provided for next reaction without being isolated from the reaction system.

Step 2

A sulfonyl chloride compound (hereinafter may be referred to as "compound (5)") represented by Formula (5) can be produced by chlorosulfonating the amide compound (4) (Reaction Scheme 5):

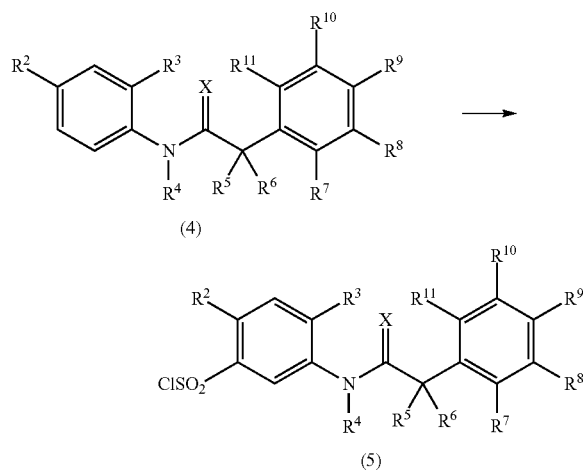

wherein $R^2$, $R^3$, $R^4$, $R^5$, $R^6$, $R^7$, $R^8$, $R^9$, $R^{10}$, $R^{11}$, and X are as defined above.

A reagent used for the chlorosulfonation is not particularly limited, and for example, include chlorosulfonic acid, and the like. When using chlorosulfonic acid, the step can be carried out in one step. For the chlorosulfonation, a two-step method including sulfonation and then chlorination can be used. The sulfonyl chloride compound (5) can be produced by reacting the amide compound with a sulfonation reagent to produce an $HOSO_2$-substituted amide compound and then reacting the $HOSO_2$-containing amide compound with a chlorination agent.

The reagent used for the sulfation is not particularly limited, and for example, chlorosulfonic acid, sulfuric acid are provided. Examples of the chlorinating agent used for the chlorination include, but are not particularly limited to, chlorine, $POCl_3$, $SOCl_2$, $SO_2Cl_2$, and oxalyl chloride.

When the chlorosulfonic acid is used, a used ratio between the amide compound (4) and the chlorosulfonic acid in the reaction therebetween is not particularly limited and can appropriately be selected from a wide range. Relative to 1 mole of the amide compound (4), typically approximately 1 to 50 moles of chlorosulfonic acid and preferably approximately 1 to 20 moles thereof is used.

When the sulfonation reagent and the chlorinating agent are used, a used ratio between the sulfonation reagent and the chlorinating agent in the reaction between the amide compound (4) and the sulfonation reagent is not particularly limited and can appropriately be selected from a wide range. Relative to 1 mole of the amide compound (4), typically approximately 1 to 50 moles of the sulfonation reagent and preferably approximately 1 to 20 moles thereof is used. A used ratio between the two in the reaction between the amide compound (4) and the chlorinating agent is not particularly limited, and can appropriately be selected from a wide range. Relative to 1 mol of the amide compound (1), typically approximately 1 to 50 moles of the sulfuric acid and preferably 1 to 20 moles thereof is used.

The aforementioned reaction is performed in an appropriate solvent or without any solvent. When the aforementioned reaction is carried out in the solvent, no limitations are placed on the solvent as long as the solvent is inactive with respect to the aforementioned reaction. As examples of such a solvent, the same solvents as those described above are listed. Any one of these solvents can be used alone or a combination of two or more types thereof can be used when necessary.

Reaction temperature for the aforementioned reaction is not particularly limited, and is typically within a range between −20° C. and a boiling point of the solvent used, preferably −10° C. to 150° C., and more preferably 0 to 100° C. Reaction time varies depending on, for example, the reaction temperature and the reaction typically ends in approximately 0.25 to 24 hours.

The sulfonyl chloride compound (5) obtained by the method shown in Step 2 is easily isolated from a reaction mixture to be purified by use of typical isolation means and purification means, for example, filtration, solvent extraction, distillation, recrystallization, column chromatography, etc.

After end of the reaction, the sulfonyl chloride compound (5) can be provided for next reaction without being isolated from the reaction system.

Step 3

A thiol compound (hereinafter may be referred to as "compound (6)") represented by Formula (6) can be produced by reacting the sulfonyl chloride compound (5) with a reducing agent (Reaction Scheme 6):

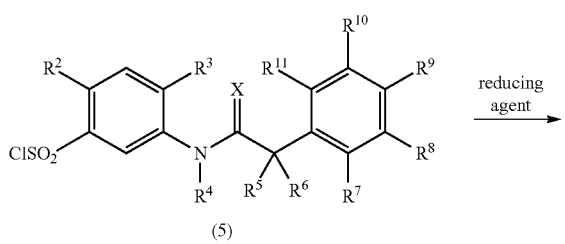

-continued

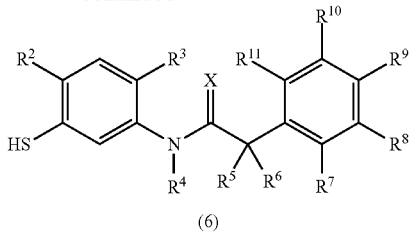

(6)

wherein $R^2$, $R^3$, $R^4$, $R^5$, $R^6$, $R^7$, $R^8$, $R^9$, $R^{10}$, $R^{11}$, and X are as defined above.

A used ratio between the sulfonyl chloride compound (5) and the reducing agent in the reaction therebetween is not particularly limited and can appropriately be selected from a wide range. Relative to 1 mole of the sulfonyl chloride compound (5), typically approximately 1 to 50 moles of the reducing agent and more preferably approximately 1 to 20 moles thereof is used.

As the reducing agent, any of conventionally known reducing agents can widely be used, and examples of the reducing agent include: triphenylphosphine and the like phosphorous compounds; reducing agents containing metal and acid such as zinc and acid, tin (II) and acid, and iron and acid; and reducing agentred phosphorus, iodine, dichlorodimethylsilane-zinc-dimethylacetamide, lithium aluminum hydride, and the like specific reducing agents. Examples of the acid include acetic acid and the like organic acids; and hydrochloric acid, sulfuric acid, and the like inorganic acids.

The aforementioned reaction is performed in an appropriate solvent. No limitations are placed on the solvent as long as the solvent is inactive with respect to the reaction. As examples of such a solvent, the same solvents as those described above are listed. Any one of these solvents can be used alone or a combination of two or more types thereof can be used when necessary.

Reaction temperature for the aforementioned reaction is not particularly limited and is typically within a range between −20° C. and a boiling point of the solvent used, preferably −10° C. to 150° C., and more preferably 20 to 120° C. Reaction time varies depending on, for example, the reaction temperature and the reaction typically ends in approximately 0.25 to 24 hours.

The thiol compound (6) obtained by the method shown in Step 3 is easily isolated from a reaction mixture to be purified by use of typical isolation means and purification means, for example, filtration, solvent extraction, distillation, recrystallization, column chromatography, etc.

After end of the reaction, the thiol compound (6) can be provided for next reaction without being isolated from the reaction system.

Method for Producing a Sulfide Compound Represented by Formula (1-1) or a Salt Thereof Examples of the method for producing the sulfide compound represented by Formula (1-1) include, but are not limited to, a production route 1, a production route 2, a production route 3, a production route 4, described below, and the like.

Production Route 1 (Step 4)

A sulfide compound (1-1) can be produced by reacting the thiol compound (6) with an alkyl reagent (hereinafter may be referred to as "alkyl reagent (7)) represented by Formula (7) (Reaction Scheme 7):

[Reaction Scheme 7]

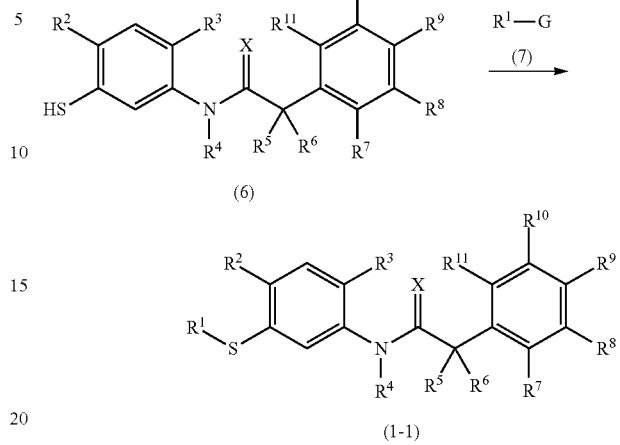

wherein $R^1$, $R^2$, $R^3$, $R^4$, $R^5$, $R^6$, $R^7$, $R^8$, $R^9$, $R^{10}$, $R^{11}$, and X are as defined above, and G represents a leaving group.

As examples of the leaving group, the same leaving groups as those described above are listed.

A used ratio between the thiol compound (6) and the alkyl reagent (7) in the reaction therebetween is not particularly limited and can appropriately be selected from a wide range. Relative to 1 mole of the thiol compound (6), typically approximately 1 to 10 moles of the alkyl reagent (7) and preferably approximately 1 to 5 moles thereof is used.

Examples of the alkyl reagent (7) include, but are not particularly limited to, methyl iodide, ethyl bromide, and the like $C_{1-6}$ alkyl halides; trifluoromethyl iodide, trifluoromethyl bromide, trifluoroethyl iodide, trifluoroethyl bromide, and the like $C_{1-6}$ haloalkyl halides; and the like.

The aforementioned reaction can be performed under presence of a base. Among the above, the aforementioned reaction is preferably performed under the presence of the base. As examples of the base, conventionally known bases can widely be used, and any of the same bases as those described above can be used.

Relative to 1 mole of the thiol compound (6), typically 1 to 10 moles of the base and preferably approximately 1 to 3 moles thereof can be used. When triethylamine, pyridine, or like an organic base is used, it can be used in large excess to serve also as a reaction solvent.

The aforementioned reaction can be performed by further adding a radical starting agent. Examples of the radical starting agent include, but are not particularly limited to, sulfurous acid, a sulfurous acid salt, Rongalit (product name, sodium-formaldehyde-sulfoxylate), and the like sulfurous acid adducts. The base and the radical starting agent can be used in combination.

When the radical starting agent is used, as an additive amount thereof, relative to 1 mole of the thiol compound (6), typically 0.1 to 10 moles of the radical starting agent and preferably approximately 0.1 to 5 moles thereof can be used.

The aforementioned reaction is performed in an appropriate solvent. Examples of the solvent include: n-hexane, cyclohexane n-heptane, and the like fatty acid or alicyclic hydrocarbon-based solvents; benzene, chlorobenzene, toluene, xylene, and the like aromatic hydrocarbon-based solvents; methylene chloride, 1,2-dichloroethane, chloroform, carbon tetrachloride, and the like halogenated hydrocarbon-based solvents; diethyl ether, THF, 1,4-dioxane, and the like ether-based solvents; methyl acetate, ethyl acetate, and the like ester-based solvents; acetonitrile; DMF, N,N-dimethylacetamide, N-methyl-2-pyrolidone, and the like amide-based solvents; dimethyl sulfoxide and the like sulfoxide-based solvents; alcohol-based solvents such as sulfolane, methanol, ethanol, isopropyl alcohol, and the like aprotic polar solvents; water; and the like. Any one of these solvents can be used alone or a combination of two or more types thereof can be used when necessary.

Reaction temperature for the aforementioned reaction is not particularly limited, and is typically within a range between −20° C. and a boiling point of the solvent used, preferably −10° C. to 60° C., and more preferably 0 to 50° C. Reaction time varies depending on, for example, the reaction temperature and the reaction typically ends in approximately 0.25 to 24 hours.

The sulfide compound (1-1) obtained by the method shown in Step 4 is easily isolated from a reaction mixture to be purified by use of typical isolation means and purification means, for example, filtration, solvent extraction, distillation, recrystallization, column chromatography, etc.

After end of the reaction, the sulfide compound (1-1) can be provided for next reaction without being isolated from the reaction system.

Production Route 2

A sulfide compound (hereinafter may be referred to as "compound (1-1b)") represented by Formula (1-1b) can be produced by reacting a sulfide compound (hereinafter may be referred to as "compound (1-1a)") represented by Formula (1-1a) with a compound (hereinafter may be referred to as "compound (7')" represented by Formula (7'): R4'-G (Reaction Scheme 8):

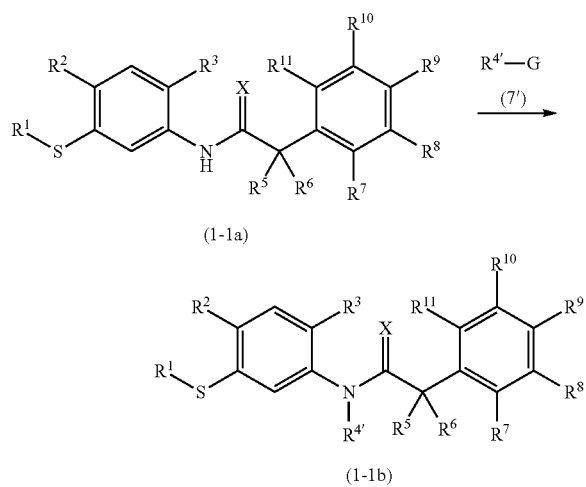

wherein $R^1$, $R^2$, $R^3$, $R^5$, $R^6$, $R^7$, $R^8$, $R^9$, $R^{10}$, $R^{11}$ and X are as defined above, and $R^{4'}$ represents formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkyl carbonyl, $C_{1-6}$ haloalkyl carbonyl, $C_{1-6}$ alkoxycarbonyl, $C_{1-6}$ haloalkoxycarbonyl, arylcarbonyl, aryloxy carbonyl, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, aryl, aryl $C_{1-6}$ alkyl, arylsulfonyl, arylsulfinyl, arylthio, and heterocyclic, and these groups may optionally be further substituted. G represents a leaving group.

As examples of the leaving group, the leaving groups as those described above are listed.

A used ratio between the sulfide compound (1-1a) and the compound (7') in the reaction therebetween is not particularly limited and can appropriately be selected from a wide range. Relative to 1 mole of the former, typically approximately 1 to 10 moles of the latter and preferably approximately equimolar to 5 moles thereof is used.

The aforementioned reaction can be performed under presence of a base. Among the above, the aforementioned reaction is preferably performed under the presence of the base. As the base, conventionally known bases can be used and any of the same bases as those described above can be used.

Relative to 1 mole of the sulfide compound (1-1a), a stoichiometric amount of the base or an excessive amount thereof over the aforementioned amount can be used. Preferably one to ten times of the base and more preferably one to five times thereof may excessively be used. When triethylamine, pyridine, or like an organic base is used, it can be used in large excess to serve also as a reaction solvent.

The aforementioned reaction is performed in an appropriate solvent. Examples of the solvent include: n-hexane, cyclohexane, n-heptane, and the like fatty acid or alicyclic hydrocarbon-based solvents; benzene, chlorobenzene, toluene, xylene, and the like aromatic hydrocarbon-based solvents; methylene chloride, 1,2-dichloroethane, chloroform, carbon tetrachloride, and the like halogenated hydrocarbon-based solvents; diethyl ether, THF, 1,4-dioxane, and the like ether-based solvents; methyl acetate, ethyl acetate, and the like esters solvents; acetonitrile; DMF, N,N-dimethylacetamide, N-methyl-2-pyrolidone, and the like amide-based solvents; dimethyl sulfoxide and the like sulfoxide-based solvents; alcohol-based solvents such as sulfolane, methanol, ethanol, and isopropyl alcohol and the like aprotic polar solvents; and water. Any one of these solvents can be used alone or a combination of two or more types thereof can be used when necessary.

Reaction temperature for the aforementioned reaction is not particularly limited and is typically within a range between −20° C. and a boiling point of the solvent used, preferably −10° C. to 60° C., and more preferably 20 to 50° C. Reaction time varies depending on, for example, the reaction temperature and the reaction typically ends in approximately 0.25 to 24 hours.

The sulfide compound (1-1b) obtained by the method shown in Step 4 is easily isolated from a reaction mixture to be purified by use of typical isolation means and purification means, for example, filtration, solvent extraction, distillation, recrystallization, column chromatography, etc.

After end of the reaction, the sulfide compound (1-1b) can be provided for next reaction without being isolated from the reaction system.

The sulfide compound (1-1) can be produced in accordance with not only what have been mentioned above but also production routes 3, 4, and 5.

Production Route 3

The sulfide compound (1-1a) can be produced by reacting an aniline compound (hereinafter may be referred to as "compound (8)") with a phenylacetic acid compound (3) (Reaction Scheme 9):

[Reaction Scheme 9]

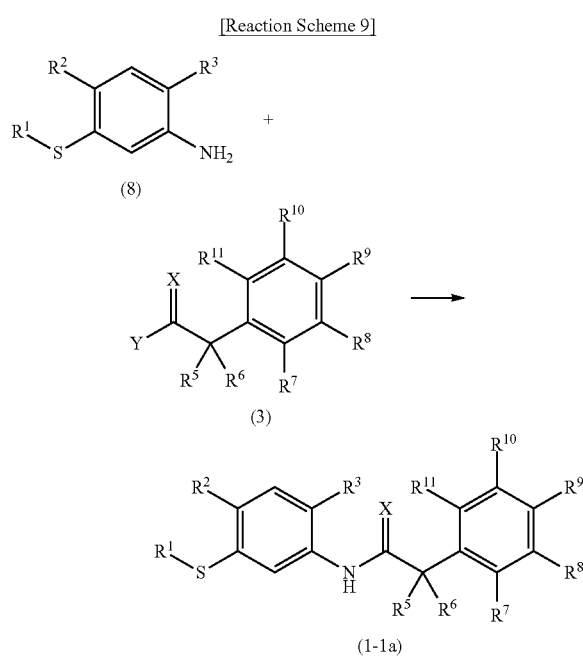

wherein $R^1$, $R^2$, $R^3$, $R^5$, $R^6$, $R^7$, $R^8$, $R^9$, $R^{10}$, $R^{11}$, X, and Y are as defined above.

Production Route 3A (when Y is a Leaving Group)

The sulfide compound (1-1a) can be produced by reacting the aniline compound (8) with a benzylcarbonyl compound (3A) (Reaction Scheme 10):

[Reaction Scheme 10]

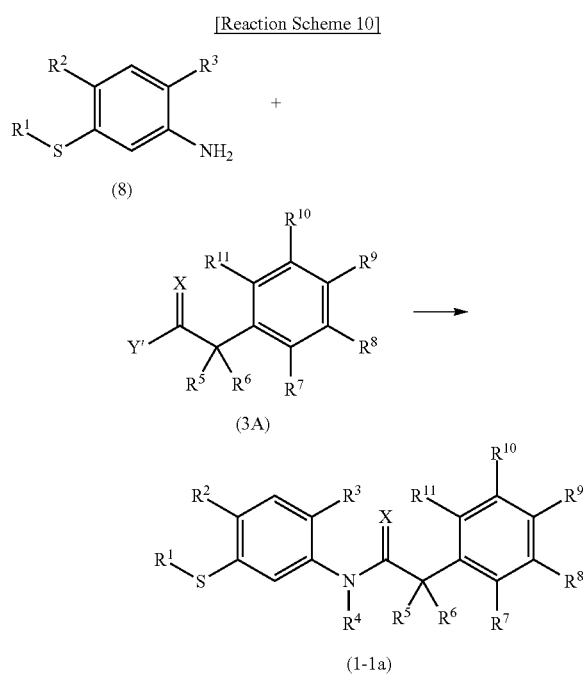

wherein $R^2$, $R^3$, $R^4$, $R^5$, $R^6$, $R^7$, $R^8$, $R^9$, $R^{10}$, $R^{11}$, and X are as defined above, and Y' represents a leaving group.

Examples of the benzylcarbonyl compound (3A) include, but are not particularly limited to, the same compounds as those of Step 1A.

The aniline compound (8) used as a starting material can be produced according to methods described in WO2007/131680.

A used ratio between the aniline compound (8) and the benzylcarbonyl compound (3A) in the reaction therebetween is not particularly limited and thus can appropriately be selected from a wide range. Relative to 1 mole of the former, typically approximately 1 to 5 moles of the latter and preferably approximately equimolar to 1.2 moles thereof is used.

The aforementioned reaction can be performed under absence or presence of a base. Among the above, the aforementioned reaction is preferably performed under the presence of the base. As examples of the base, any of the same bases as those shown in Step 1 above can be used. Any separate one of these bases or a combination of two or more types thereof is used.

Relative to 1 mole of the aniline compound (8), a stoichiometric amount of the base or an excessive amount thereof over the aforementioned amount can excessively be used.

Preferably one to five times of the base may excessively be used. When triethylamine, pyridine, or like an organic base is used, it can be used in large excess to serve also as a reaction solvent.

The aforementioned reaction is performed in an appropriate solvent or without any solvent. When the aforementioned reaction is carried out in the solvent, any of the same solvents as those shown in Step 1 above can be used. Any one of these solvents can be used alone or a combination of two or more types thereof can be used when necessary.

Reaction temperature for the aforementioned reaction is not particularly limited and is typically within a range between −20° C. and a boiling point of the solvent used and preferably 0 to 50° C. Reaction time varies depending on, for example, the reaction temperature and the reaction typically ends in approximately 0.5 to 24 hours.

The aniline compound (8) used as a starting material is a known compound or a compound that can easily be produced by a known method.

The sulfide compound (1-1a) is easily isolated from a reaction mixture to be purified by use of typical isolation means and purification means, for example, filtration, solvent extraction, distillation, recrystallization, column chromatography, etc.

After end of the reaction, the sulfide compound (1-1a) can be provided for next reaction without being isolated from the reaction system.

Step 3B (when Y is a Hydroxyl Group)

As another method for obtaining the phenylacetamide compound (1-1a), the compound (1-1a) can be produced by reacting the aniline compound (8) with a phenylacetic acid compound (3B) (Reaction Scheme 11):

[Reaction Scheme 11]

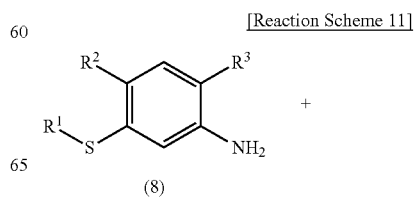

-continued

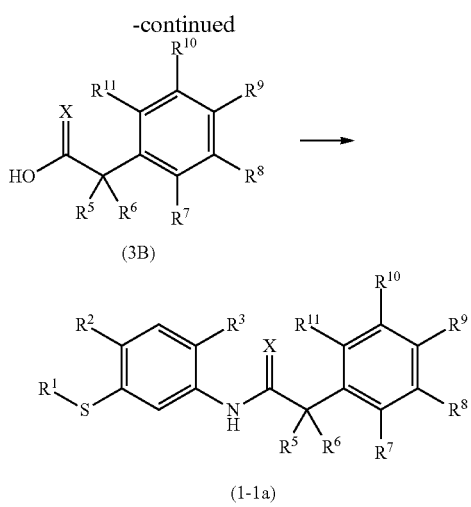

wherein $R^1$, $R^2$, $R^3$, $R^5$, $R^6$, $R^7$, $R^8$, $R^9$, $R^{10}$, $R^{11}$, and X are as defined above.

A used ratio between the aniline compound (8) and the phenylacetic acid compound (3B) in the reaction therebetween is not particularly limited and thus can appropriately be selected from a wide range. Relative to 1 mole of the former, typically approximately 1 to 5 moles of the latter and preferably equimolar to 1.2 moles thereof is used.

The aforementioned reaction can be performed under absence or presence of a condensing agent. Among the above, the aforementioned reaction is preferably performed under the presence of the condensing agent. As examples of the condensing agent, the same condensing agents as those shown in Step 1B are listed. Any separate one of these condensing agents or a combination of two or more types thereof is used.

Relative to 1 mole of the aniline compound (8), a stoichiometric amount of the condensing agent or an excessive amount thereof over the aforementioned amount can be used. Preferably approximately one to five times of the condensing agent may excessively be used.

The aforementioned reaction can be performed under absence or presence of a base. Among the above, the aforementioned reaction is preferably performed under the presence of the base. As the base, any of the same bases as those shown in Step 1 above can be used. Any separate one of these bases or a combination of two or more types thereof is used.

Relative to 1 mole of the aniline compound (8), a stoichiometric amount of the base or an excessive amount thereof over the aforementioned amount can be used. Preferably approximately 1 to 5 times of the base can excessively be used. When triethylamine, pyridine, or like an organic base is used, it can be used in large excess to serve also as a reaction solvent.

The aforementioned reaction is performed in an appropriate solvent or without any solvent. When the aforementioned reaction is carried out in the solvent, any of the same solvents as those shown in Step 1 above can be used. Any one of these solvents can be used alone or a combination of two or more types thereof can be used when necessary.

Reaction temperature for the aforementioned reaction is not particularly limited and is typically within a range between −20° C. and a boiling point of the solvent used and preferably 0 to 25° C. Reaction time varies depending on, for example, the reaction temperature and the reaction typically ends in approximately 0.5 to 24 hours.

Production Route 3C

Note that as a method for producing the phenylacetamide compound (1-1a), a phenylacetic acid halide compound (3C) obtained by reacting the phenylacetic acid compound (3B) with a halogenation reagent can be used as a material.

The aforementioned reaction can be performed under presence of a base. As the base, any of the same bases as those described above can be used, and preferable examples of the base include triethylamine, pyridine, di-isopropylamine, 4-diisopropylethylamine, 4-dimethylamine pyridine, lutidine, and the like organic bases. The bases can much excessively be used to be also used as reaction solvents.

Examples of the halogen reagent include, but are not particularly limited to, $POCl_3$, $POBr_3$, $SOCl_2$, $SO_2Cl_2$, and oxalyl chloride.

Relative to 1 mole of the aniline compound (2), typically 1 to 10 moles of the halogenation reagent and preferably approximately 1 to 5 moles thereof can be used.

The aforementioned reaction is performed in an appropriate solvent or without any solvent. When the aforementioned reaction is carried out in the solvent, no limitations are placed on the solvent as long as the solvent is inactive with respect to the aforementioned reaction. As examples of such a solvent, the aforementioned solvents are listed. Any one of these solvents can be used alone or a combination of two or more types thereof can be used when necessary.

Reaction temperature for the aforementioned reaction is not particularly limited and is typically within a range between 10° C. and a boiling point of the solvent used and preferably within a range between −5° C. and the boiling point of the solvent. Reaction time varies depending on, for example, the reaction temperature, and the reaction typically ends in approximately 0.25 to 24 hours.

The sulfide compound (1-1a) is easily isolated from a reaction mixture to be purified by use of typical isolation means and purification means, for example, filtration, solvent extraction, distillation, recrystallization, column chromatography, etc.

After end of the reaction, the sulfide compound (1-1a) can be provided for next reaction without being isolated from the reaction system.

Production Route 4

The sulfide compound (1-1) can be produced by reacting a sulfide compound (hereinafter may be referred to as "compound (9)") with an amide compound (hereinafter may be referred to as "compound (10)") represented by Formula (10) (Reaction Scheme 12):

[Reaction Scheme 12]

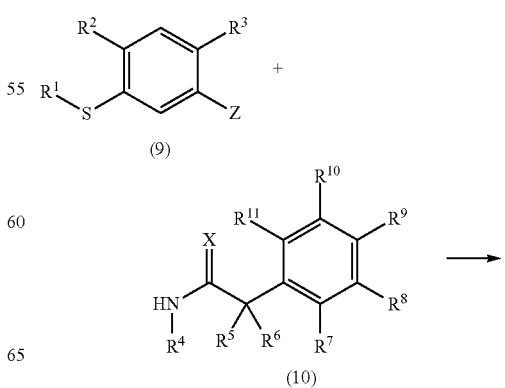

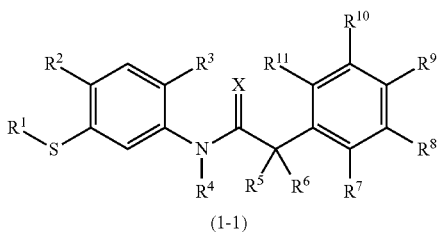

(1-1)

wherein $R^1$, $R^2$, $R^3$, $R^4$, $R^5$, $R^6$, $R^7$, $R^8$, $R^9$, $R^{10}$, $R^{11}$, and X are as defined above, and Z represents a leaving group.

A used ratio between the sulfide compound (9) and the amide compound (10) in the reaction therebetween is not particularly limited and can appropriately be selected from a wide range. Relative to 1 mole of the former, typically approximately 1 to 10 moles of the latter and preferably approximately equimolar to 5 moles thereof is used.

The aforementioned reaction can be performed under absence or presence of a base. Among the above, the aforementioned reaction is preferably performed under the presence of the base. As the base, any of the same bases as those shown in Step 1 above can be used. Any separate one of these bases or a combination of two or more types thereof is used.

Relative to 1 mole of the aniline compound (9), typically 1 to 10 moles of the base and preferably approximately 1 to 5 moles thereof is used.

The aforementioned reaction is performed in an appropriate solvent or without any solvent. When the aforementioned reaction is carried out in the solvent, any of the same solvents as those shown in the Step 1 above can be used. Any one of these solvents can be used alone or a combination of two or more types thereof can be used when necessary.

Reaction temperature for the aforementioned reaction is not particularly limited and is typically within a range between −10° C. and a boiling point of the solvent used and preferably between −0° C. and the boiling point of the solvent. Reaction time varies depending on, for example, the reaction temperature and the reaction typically ends in approximately 0.5 to 24 hours.

The sulfide compound (9) used as a starting material can be produced according to methods described in EP3002279 and WO2012/176856.

The sulfide compound (1-1) is easily isolated from a reaction mixture to be purified by use of typical isolation means and purification means, for example, filtration, solvent extraction, distillation, recrystallization, column chromatography, etc.

After end of the reaction, the sulfide compound (1-1) can be provided for next reaction without being isolated from the reaction system.

Step 5

A benzylamide compound (hereinafter may be referred to as "compound (1-2)") represented by Formula (1-2) can be produced by reacting a sulfide compound represented by Formula (1-1) with an oxidizing agent (Reaction Scheme 13):

[Reaction Scheme 13]

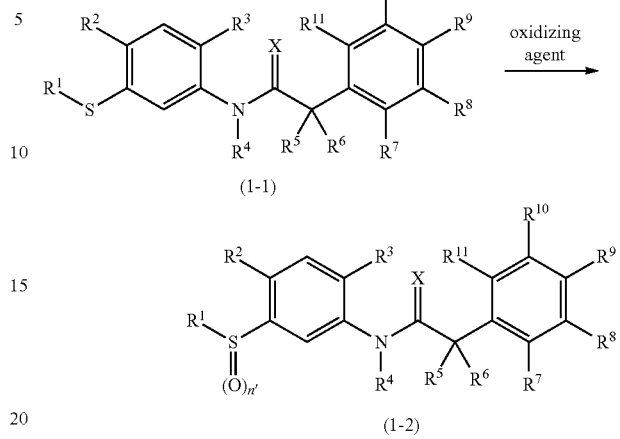

wherein $R^1$, $R^2$, $R^3$, $R^4$, $R^5$, $R^6$, $R^7$, $R^8$, $R^9$, $R^{10}$, $R^{11}$, X, and n' are as described above.

A used ratio between the benzylamide compound (1-1) and the oxidizing agent in the reaction therebetween is not particularly limited and can appropriately be selected from a wide range. Relative to 1 mole of the former, typically approximately 1 to 10 moles of the latter and preferably approximately equimolar to 5 moles thereof is used.

The aforementioned reaction can be performed under presence of the oxidizing agent. As the oxidizing agent, any of known oxidizing agents can be used as long as the oxidizing agent can achieve oxidization of sulfide into sulfoxide, and examples of the oxidizing agent include a combination of: performic acid, peracetic acid, pertrifluoroacetic acid, perbenzoic acid, m-chloroperbenzoic acid (mCPBA), o-carbonylperbenzoic acid, and the like peracids; hydrogen peroxide, t-butylhydroperoxide, cumene hydroperoxide, and the like alkyl hydroperoxides; and titanium tetraisopropoxide and the like titanium tetraalkoxides; dichromate, sodium bichromate, potassium bichromate, and the like dichromate salts; and permanganic acid, sodium permanganate, potassium permanganate, and the like permanganates; and the like. Any separate one of these oxidizing agents or a combination of two or more types thereof is used.

Relative to 1 mole of the benzylamide compound (1-1), a stoichiometric amount of the oxidizing agent or an excessive amount thereof over the aforementioned amount can excessively be used. Preferably one to ten times of the oxidizing agent and more preferably approximately one to five times thereof may be used.

The aforementioned reaction can further be performed by adding a catalyst.

The aforementioned reaction is performed in an appropriate solvent. Examples of the solvent include: n-hexane, cyclohexane, n-heptane, and the like fatty acid or alicyclic hydrocarbon-based solvents; benzene, chlorobenzene, toluene, xylene, and the like aromatic hydrocarbon-based solvents; methylene chloride, 1,2-dichloroethane, chloroform, carbon tetrachloride, and the like halogenated hydrocarbon-based solvents; diethyl ether, THF, 1,4-dioxane, and the like ether-based solvents; methyl acetate, ethyl acetate, and the like esters solvents; acetonitrile; DMF, N,N-dimethylacetamide, N-methyl-2-pyrolidone, and the like amide-based solvents; dimethyl sulfoxide and the like sulfoxide-based solvents; alcohol-based solvents such as sulfolane, methanol, ethanol, isopropyl alcohol, and the like aprotic polar solvents. Any one of these solvents can be used alone or a combination of two or more types thereof can be used when necessary.

Reaction temperature for the aforementioned reaction is not particularly limited, and is typically within a range between −20° C. and a boiling point of the solvent used, preferably −10° C. to 60° C., and more preferably 20 to 50° C. Reaction time varies depending on, for example, the reaction temperature, and the reaction typically ends in approximately 0.25 to 24 hours.

The sulfide compound (1-2) obtained by the method shown in Step 5 is easily isolated from a reaction mixture to be purified by use of typical isolation means and purification means, for example, filtration, solvent extraction, distillation, recrystallization, chromatography, etc.

Each compound (1) obtained after the completion of the reactions shown in Reaction Scheme 1 to Reaction Scheme 13 may be easily isolated from the reaction mixture and purified by known isolation and purification techniques, such as filtration, solvent extraction, distillation, recrystallization, and column chromatography.

When compound (1) has regioisomers, each regioisomer may be separated by a usual separation step, such as silica gel chromatography.

Pest-Controlling Agent

Compound (1) of the present invention may be used as an active ingredient of a pest-controlling agent. Examples of pest-controlling agents include agents (agricultural and horticultural insecticide, miticides, nematicides, or soil insecticides) for controlling pests, mites, nematode, or soil pests that all cause problems in the agricultural and horticultural fields; animal-ectoparasite-controlling agents (e.g., pulicide, ixodicide, and pedivulicideon), and the like.

For use as an active ingredient of a pest-controlling agent, it is possible to use compound (1) of the present invention as is with no additional components. However, it is usually preferable to use the compound by combining with a solid carrier, liquid carrier, or gaseous carrier (propellant), and optionally with a surfactant and other adjuvants for pharmaceutical preparation, and formulating the resulting mixture into various forms such as oil solutions, emulsions, wettable powders, flowable preparations, granules, dusts, aerosols, fumigants, or the like, according to known preparation methods.

Compound (1) of the present invention is usually contained in these formulations in a proportion of 0.01 to 95 wt %, and preferably 0.1 to 50 wt %.

Examples of solid carriers usable in the formulations include solid carriers in a fine powder or granular form, such as clay (e.g., kaolin clay, diatomaceous earth, synthetic hydrated silicon dioxide, bentonite, Fubasami clay, and acid clay), talc, ceramic, other inorganic minerals (e.g., celite, quartz, sulfur, active carbon, calcium carbonate, and hydrated silica), and chemical fertilizers (e.g., ammonium sulfate, ammonium phosphate, ammonium nitrate, urea, and ammonium chloride); and the like.

Examples of liquid carriers include water, alcohols (e.g., methanol and ethanol), ketones (e.g., acetone and methylethylketone), aromatic hydrocarbons (e.g., benzene, toluene, xylene, ethylbenzene, and methylnaphthalene), aliphatic hydrocarbons (e.g., hexane, cyclohexane, kerosene, and light oil), esters (e.g., ethyl acetate and butyl acetate), nitriles (e.g., acetonitrile and isobutyronitrile), ethers (e.g., diisopropyl ether and dioxane), acid amides (e.g., N,N-dimethylformamide and N,N-dimethylacetamide), halogenated hydrocarbons (e.g., dichloromethane, trichloroethane, and carbon tetrachloride), dimethylsulfoxide, soybean oil, cottonseed oil, and like vegetable oils, and the like.

Examples of gaseous carriers include butane gas, LPG (liquefied petroleum gas), dimethyl ether, carbon dioxide gas, and the like.

Examples of surfactants include alkyl sulfates, alkyl sulfonates, alkylaryl sulfonates, alkyl aryl ethers, polyoxyethylene adducts thereof, polyethylene glycol ethers, polyhydric alcohol esters, sugar alcohol derivatives, and the like.

Examples of adjuvants for pharmaceutical preparation include fixing agents, dispersants, stabilizers, and the like.

Examples of the fixing agents and dispersants include casein, gelatin, polysaccharides (e.g., starch, gum arabic, cellulose derivatives, and alginic acid), lignin derivatives, bentonite, sugars, and water-soluble synthetic polymers (e.g., polyvinyl alcohol, polyvinyl pyrrolidone, and polyacrylic acids).

Examples of stabilizers include PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, fatty acids, and fatty acid esters, and the like.

For the pest-controlling agent of the present invention, it is preferable to use compound (1) as is, or by diluting it with water or the like. The pest-controlling agent of the present invention may be used by mixing with, for example, other pest-controlling agents, such as known insecticides, nematicides, acaricides, fungicides, herbicides, plant-growth-controlling agents, synergists, soil conditioners, animal feeds, and the like, or it may be used simultaneously with these agents without mixing.

The amount of the pest-controlling agent of the invention is not limited, and may be suitably selected from a wide range according to various conditions such as the concentration of active ingredient, the form of preparation, type of disease or pest to be treated, type of plant, severity of disease, time for application, method for application, chemicals to be used in combination (insecticide, nematicide, miticide, fungicide, herbicide, plant growth control agent, synergist, soil conditioner, etc.), and amount and type of fertilizer.

When used as a pesticide, compound (1) of the present invention is usually used in an amount of 0.01 to 500 g/100 m$^2$, and preferably 1 to 200 g/100 m$^2$.

When used as a miticide, compound (1) of the present invention is usually used in an amount of 0.1 to 500 g/100 m$^2$, and preferably 1 to 200 g/100 m$^2$.

When the emulsion, wettable powder, flowable preparation, or the like is used by diluting with water, the concentration is 0.1 to 1,000 ppm, and preferably 1 to 500 ppm. The granules, dusts, or the like can be used as is without dilution.

Compound (1) of the present invention is characterized by having a particularly excellent miticidal activity and a broad spectrum of activity.

Compound (1) of the present invention is effectively used as an agricultural and horticultural insecticide, miticide, nematicide, or a soil insecticide. Specifically, compound (1) of the present invention is effective for controlling pests, such as green peach aphids, cotton aphids, and like aphids; diamondback moths, cabbage armyworms, common cutworms, codling moths, bollworms, tobacco budworms, gypsy moths, rice leafrollers, smaller tea tortrix moths, Colorado potato beetles, cucurbit leaf beetles, boll weevils, plant hoppers, leafhoppers, scales, bugs, whiteflies, thrips, grasshoppers, anthomyiid flies, scarabs, black cutworms, cutworms, ants, and agricultural pest insects; slugs, snails, and like gastropods; rat mite, cockroaches, houseflies, house mosquitoes, and like hygiene-harming insects; angoumois grain moths, adzuki bean weevils, red flour beetles, mealworms, and like stored-grain insects; casemaking clothes moths, black carpet beetles, subterranean termites, and like clothes-harming insects and house- and household-harming insects; and the like, mites, such as two-spotted spider mites, carmine spider mites, citrus red mites, Kanzawa spider mites, European red mites (fruit tree spider mites), broad mites, pink citrus rust mites, bulb mites, and like plant-parasitic mites; *Tyrophagus putrescentiae, Dermatophagoides farinae, Chelacaropsis moorei*, and like house dust mites; and the like, and soil pests, such as root-knot nematodes, cyst nematodes, root-lesion nematodes, white-tip nematode, strawberry bud nematode, pine wood nematode, and like plant parasitic nematodes; pill bugs, sow bugs, and like isopods; and the like.

The pest-controlling agent of the present invention is also effective for controlling various pests resistant to chemicals such as organophosphorus agents, carbamate agents, synthetic pyrethroid agents, and neonicotinoid agent.

Reference literatures such as scientific literatures, patents, and patent applications cited herein are incorporated herein by reference to the same extent that the entirety of each document is specifically described. As used herein, "or" is used when "at least one or more" matters listed in the sentence can be used.

EXAMPLES

As described above, the present invention has been explained while showing preferred embodiments to facilitate understanding. Hereinafter, the present invention is described in more detail with reference to the following Production Examples and Examples; however, the aforementioned explanation and the following Production Examples and Examples are not provided to limit the present invention, but for the sole purpose of exemplification. Thus, the scope of the present invention is not limited to embodiments and these Examples specifically described herein and is limited only by the scope of claims.

Production Example 1

Preparation of N-(2-fluoro-4-methylphenyl)-2-(4-(trifluoromethoxy) phenyl) acetamide (4-14)

To a solution of 2-fluoro-4-methylaniline (2-14; 1.1 g, 8.79 mmol, 1 equiv.) and 2-(4-(trifluoromethoxy) phenyl) acetic acid (3b-14; 2.12 g, 9.67 mmol, 1.1 equiv.) in pyridine (10 ml) slowly added $POCl_3$ (1.6 ml, 17.58 mmol, 2 equiv.) at 0° C. The reaction was further maintained at the same temperature for 15 minutes. The reaction mixture was then quenched into ice and the product was then extracted with ethyl acetate. The combined organic layer was washed by 1N HCl solution followed by brine solution, dried over sodium sulfate, filtered and concentrated under reduced pressure to get 2.20 g of the crude product 4-14 as yellow solid. The crude product thus obtained was further used as such without any purification.

$^1$H NMR (CDCl$_3$): 8.10 (t, J=8.6 Hz, 1H), 7.39-7.37 (m, 2H), 7.25-7.23 (m, 3H), 6.92-6.85 (m, 2H), 3.75 (s, 2H), 2.29 (s, 3H).

Production Example 2

Preparation of 5-(2-(4-(trifluoromethoxy) phenyl) acetamide)-4-fluoro-2-methylbenzene-1-sulfonyl Chloride (5-14)

Chlorosulfonic acid (14.0 g, 120 mmol, 18 equiv.) was added to N-(2-fluoro-4-methylphenyl)-2-(4-(trifluoromethoxy) phenyl) acetamide (4-14; 2.20 g, 6.72 mmol, 1 equiv.) at a temperature below 50° C. The reaction mixture was then stirred at room temperature overnight. The reaction mixture was then quenched into ice, the product was then extracted with ethyl acetate. The combined organic layer was washed by distilled water, dried over sodium sulfate, filtered and concentrated under reduced pressure to get 2.60 g of the crude product 5-14 as black viscous oil. The crude product thus obtained was further used as such without any purification.

$^1$H NMR (CDCl$_3$): 9.08 (d, J=7.6 Hz, 1H), 7.39-7.36 (m, 2H), 7.25-7.24 (m, 3H), 7.12 (d, J=10.8 Hz, 1H), 3.79 (s, 2H), 2.71 (s, 3H).

Production Example 3

Preparation of N-(2-fluoro-5-mercapto-4-methylphenyl)-2-(4-(trifluoromethoxy) phenyl) acetamide (6-14)

To a mixture of 5-(2-(4-(trifluoromethoxy) phenyl) acetamide)-4-fluoro-2-methylbenzene-1-sulfonyl chloride (5-14; 2.60 g, 6.11 mmol, 1 equiv.) in toluene (20 ml) was added triphenyl phosphine (4.8 g, 18.35 mmol, 3 equiv.) at room temperature. The reaction was then heated to 100° C. for 3 hours. The reaction mixture was cooled to room temperature and all the volatiles were distilled out by rotary evaporator. The crude product thus obtained was purified by column chromatography on silica gel with a mixture of ethyl acetate and n-hexane as an eluent to obtain 1.0 g of the title compound 6-14 as an off white solid.

$^1$H NMR (CDCl$_3$): 8.26 (d, J=7.6 Hz, 1H), 7.38-7.36 (m, 2H), 7.25-7.21 (m, 3H), 6.87 (d, J=10.8 Hz, 1H), 3.74 (s, 2H), 3.30 (s, 1H), 2.25 (s, 3H).

Example 1

Preparation of N-(5-(2,2,2-trifluoroethylthio)-2-fluoro-4-methylphenyl)-2-(4-(trifluoromethoxy) phenyl) acetamide (1A-14)

To a cooled mixture of N-(2-fluoro-5-mercapto-4-methylphenyl)-2-(4-(trifluoromethoxy) phenyl) acetamide (6-14; 1.00 g, 2.78 mmol, 1 equiv.) in DMF (10 ml) was added cesium carbonate (0.90 g, 2.78 mmol, 1 equiv.) followed by sodium formaldehyde sulfoxylate (0.33 g, 2.78 mmol, 1 equiv.). To this mixture was then added slowly trifluoroethyl iodide (0.639 g, 3.06 mmol, 1.1 equiv.) at 0° C. and the resulting mixture was then stirred at room temperature for 6 hours. The reaction mixture was then poured into distilled water and extracted with dichloromethane. The combined organic layer was washed with distilled water, dried over sodium sulfate, filtered and concentrated under reduced pressure to obtain a crude product. The crude product thus obtained was purified by column chromatography on silica gel with a mixture of ethyl acetate and n-hexane as an eluent to obtain 0.95 g of the title compound 1A-14 as a pale yellow solid.

Production Example 4

Preparation of N-(2-fluoro-4-methylphenyl) acetamide

To a mixture of 2-fluoro-4-methylaniline (5.50 g, 43.95 mmol, 1 equiv.) in chloroform (30 ml), a solution of acetic anhydride (4.49 g, 43.95 mmol, 1 equiv.) in chloroform (20 ml) was slowly added at 0° C. The reaction mixture was then stirred at room temperature for 3 hours. The reaction mixture was then quenched into sodium bicarbonate solution and the product was extracted with dichloromethane. The combined organic layer was washed by sodium bicarbonate solution followed by distilled water, dried over sodium sulfate, filtered and concentrated under reduced pressure to get 5.92 g of the crude product as white solid. The crude product thus obtained was further used as such without any purification.

$^1$H NMR (CDCl$_3$): δ 8.14-8.10 (m, 1H), 7.25 (bs, 1H), 6.93-6.88 (m, 2H), 2.31 (s, 3H), 2.20 (s, 3H).

Production Example 5

Preparation of 5-acetamido-4-fluoro-2-methylbenzene-1-sulfonyl Chloride

Chlorosulfonic acid (20.56 g, 176.46 mmol, 5 equiv.) was slowly added to N-(2-fluoro-4-methylphenyl) acetamide (5.90 g, 35.29 mmol, 1 equiv.) keeping the temperature of the reaction mixture below 50° C. The resulting mixture was then heated to 70° C. for 4 hours. After cooling to room temperature, the reaction mixture was then poured carefully into ice, the precipitate was filtered, washed well with distilled water and dried to get 7.3 g of crude product as light brown solid. The crude product thus obtained was further used as such without any purification.

$^1$H NMR (CDCl$_3$): δ 9.09 (d, J=7.6 Hz, 1H), 7.48 (bs, 1H), 7.14 (d, J=10.8 Hz, 1H), 2.72 (s, 3H), 2.25 (s, 3H).

Production Example 6

Preparation of N-(2-fluoro-5-mercapto-4-methylphenyl) acetamide

To a mixture of 5-acetamido-4-fluoro-2-methylbenzene-1-sulfonyl chloride (7.00 g, 26.34 mmol, 1 equiv.) in glacial acetic acid (60 ml) was portion-wise added zinc dust (34.44 g, 526.80 mmol, 20 equiv.) at room temperature. The resulting mixture was then refluxed for 4 hours. After cooling to room temperature, the reaction mixture was diluted with distilled water and ethyl acetate and filtered through celite bed. The organic layer was washed well by distilled water, dried over sodium sulfate, filtered and concentrated under reduced pressure to get 3.64 g of the crude product as pale yellow solid. The crude product thus obtained was further used as such without any purification.

$^1$H NMR (CDCl$_3$): δ 8.25 (d, J=7.6 Hz, 1H), 7.29 (bs, 1H), 6.89 (d, J=11.6 Hz, 1H), 3.34 (bs, 1H), 2.26 (s, 3H), 2.20 (s, 3H).

Production Example 7

Preparation of N-(5-(2,2,2-trifluoroethylthio)-2-fluoro-4-methylphenyl) acetamide To a cooled mixture of N-(2-fluoro-5-mercapto-4-methylphenyl) acetamide (3.10 g, 15.56 mmol, 1 equiv.) in DMF (30 ml) was added cesium carbonate (5.07 g, 15.56 mmol, 1 equiv.) followed by sodium formaldehyde sulfoxylate (1.84 g, 15.56 mmol, 1 equiv.). To this mixture was then added slowly trifluoroethyl iodide (3.27 g, 15.56 mmol, 1 equiv.) and the resulting mixture was then stirred at room temperature for 6 hours. The reaction mixture was then poured into distilled water and extracted with dichloromethane. The combined organic layer was washed with distilled water, dried over sodium sulfate, filtered and concentrated under reduced pressure to get crude product. The crude product thus obtained was purified by column chromatography on silica gel with a mixture of ethyl acetate and n-hexane as an eluent to obtain 2.90 g of the title compound as an off white solid.

$^1$H NMR (CDCl$_3$): δ 8.49 (d, J=8.0 Hz, 1H), 7.29 (bs, 1H), 6.96 (d, J=11.6 Hz, 1H), 3.42-3.35 (q, J=9.6 Hz, 2H), 2.41 (s, 3H), 2.21 (s, 3H).

Production Example 8

Preparation of 5-(2,2,2-trifluoroethylthio)-2-fluoro-4-methylaniline

To a mixture of N-(5-(2,2,2-trifluoroethylthio)-2-fluoro-4-methylphenyl) acetamide (2.20 g, 7.82 mmol, 1 equiv.) in ethanol/water (30 ml/4 ml) was added concentrated HCl (30 ml). The resulting mixture was then refluxed for 6 hours. After cooling to room temperature, all volatiles were removed by vacuum distillation and pH of the residue was then made basic by slow addition of 1N NaOH solution. The product was then extracted with ethyl acetate. The combined organic layer was then washed with distilled water followed by brine solution, dried over sodium sulfate, filtered and concentrated under reduced pressure to get crude product as a brown oil. The crude product thus obtained was further used as such without any purification.

$^1$H NMR (CDCl$_3$): δ 6.98 (d, J=9.2 Hz, 1H), 6.86 (d, J=11.6 Hz, 1H), 3.64 (bs, 2H), 3.32-3.25 (q, J=9.6 Hz, 2H), 2.36 (s, 3H).

Example 2

Preparation of N-(5-(2,2,2-trifluoroethylthio)-2-fluoro-4-methylphenyl)-2-phenylacetamide (1A-1)

To a cooled solution of 5-(2,2,2-trifluoroethylthio)-2-fluoro-4-methylaniline (0.10 g, 0.42 mmol, 1 equiv.) in chloroform (10 ml), triethylamine (0.046 g, 0.46 mmol, 1.1 equiv.) was added followed by slow addition of 2-phenylacetyl chloride (0.068 g, 0.44 mmol, 1.05 equiv.). The resulting mixture was then stirred at room temperature for 14 hours. The reaction mixture was then poured into NaHCO$_3$ solution and the product was extracted by dichloromethane. The combined organic layer was then washed with distilled water followed by brine solution, dried over sodium sulfate, filtered and concentrated under reduced pressure to get 0.125 g of title product as an off white solid.

Example 3

Preparation of N-(5-(2,2,2-trifluoroethylthio)-2-fluoro-4-methylphenyl)-2-(2-chlorophenyl) acetamide (1A-3)

To a cooled solution of 5-(2,2,2-trifluoroethylthio)-2-fluoro-4-methylaniline (0.05 g, 0.21 mmol, 1 equiv.) in dichloromethane (10 ml), triethylamine (0.042 g, 0.42 mmol, 2.0 equiv.) was added followed by slow addition of 2-(2-chlorophenyl) acetyl chloride (0.04 g, 0.21 mmol, 1 equiv.). The resulting mixture was then stirred at room temperature for 14 hours. The reaction mixture was then poured into NaHCO$_3$ solution and the product was extracted by dichloromethane. The combined organic layer was then washed with distilled water followed by brine solution, dried over sodium sulfate, filtered and concentrated under reduced pressure to get crude product. The crude product thus obtained was purified by column chromatography on silica gel with a mixture of ethyl acetate and n-hexane as an eluent to obtain 0.07 g of the title compound as a brown solid.

Example 4

Preparation of N-(5-(2,2,2-trifluoroethylthio)-2-fluoro-4-methylphenyl)-2-(2,5-dichlorophenyl) acetamide (1A-4)

To a cooled mixture of 5-(2,2,2-trifluoroethylthio)-2-fluoro-4-methylaniline (0.05 g, 0.21 mmol, 1 equiv.) and 2-(2,5-dichlorophenyl)acetic acid (0.05 g, 0.25 mmol, 1.2 equiv.) in pyridine (3 ml), POCl$_3$ (0.08 g, 0.52 mmol, 2.5 equiv.) was added very slowly. After few minutes, the reaction mixture was poured into ice and the product was extracted with ethyl acetate. The combined organic layer was then washed with 1N HCl followed with distilled water, dried over sodium sulfate, filtered and concentrated under reduced pressure to get crude product. The crude product thus obtained was purified by column chromatography on silica gel with a mixture of ethyl acetate and n-hexane as an eluent to obtain 0.023 g of the title compound as a light yellow solid.

Example 5

Preparation of 2-(4-(ethylthio)phenyl)-N-(2-fluoro-4-methyl-5-((2,2,2-trifluoroethyl)thio)phenyl)acetamide (1B-1)

To a cooled mixture of 5-(2,2,2-trifluoroethylthio)-2-fluoro-4-methylaniline (0.20 g, 0.835 mmol, 1 equiv.) and 2-(4-(ethylthio)phenyl)acetic acid (0.186 g, 1.021 mmol, 1.2 equiv.) in pyridine (3 ml), POCl$_3$ (0.08 g, 5.348 mmol, 6.4 equiv.) was added very slowly. After few minutes, the reaction mixture was poured into ice and the product was extracted with ethyl acetate. The combined organic layer was then washed with 1N HCl followed with distilled water, dried over sodium sulfate, filtered and concentrated under reduced pressure to get crude product. The crude product thus obtained was purified by column chromatography on silica gel with a mixture of ethyl acetate and n-hexane as an eluent to obtain 0.18 g of the title compound as a yellow solid.

Example 6

Preparation of N-(2-fluoro-4-methyl-5-((2,2,2-trifluoroethyl)thio)phenyl)-2-(4-(propylthio)phenyl) acetamide (1B-2)

To a cooled mixture of 5-(2,2,2-trifluoroethylthio)-2-fluoro-4-methylaniline (0.20 g, 0.835 mmol, 1 equiv.) and 2-(4-(propylthio)phenyl)acetic acid (0.327 g, 1.556 mmol, 1.8 equiv.) in pyridine (3 ml), POCl$_3$ (0.08 g, 5.348 mmol, 6.4 equiv.) was added very slowly. After few minutes, the reaction mixture was poured into ice and the product was extracted with ethyl acetate. The combined organic layer was then washed with 1N HCl followed with distilled water, dried over sodium sulfate, filtered and concentrated under reduced pressure to get crude product. The crude product thus obtained was purified by column chromatography on silica gel with a mixture of ethyl acetate and n-hexane as an eluent to obtain 0.13 g of the title compound as a yellow solid.

Example 7

Preparation of N-(2-fluoro-4-methyl-5-((2,2,2-trifluoroethyl)thio)phenyl)-2-(4-(isopropylthio)phenyl) acetamide (1B-3)

To a cooled mixture of 5-(2,2,2-trifluoroethylthio)-2-fluoro-4-methylaniline (0.20 g, 0.835 mmol, 1 equiv.) and 2-(4-(isopropylthio)phenyl)acetic acid (0.155 g, 0.737 mmol, 0.8 equiv.) in pyridine (3 ml), POCl$_3$ (0.08 g, 5.348 mmol, 6.4 equiv.) was added very slowly. After few minutes, the reaction mixture was poured into ice and the product was extracted with ethyl acetate. The combined organic layer was then washed with 1N HCl followed with distilled water, dried over sodium sulfate, filtered and concentrated under reduced pressure to get crude product. The crude product thus obtained was purified by column chromatography on silica gel with a mixture of ethyl acetate and n-hexane as an eluent to obtain 0.12 g of the title compound as a yellow solid.

Example 8

The compounds shown in Tables 1 to 4, other than the compounds obtained in Examples 1 to 7, were produced by methods similar to the methods described in Examples 1 to 7 or methods described in the description.

Tables 2 and 4 show $^1$H-NMR data of the thus obtained compounds of the present invention.

The abbreviations in Tables 1 to 4 are as indicated below.

F: fluoro, Cl: chloro, Br: bromo, Me: methyl, Et: ethyl, n-Pr: normal-propyl, i-Pr: isopropyl, n-Bu: normal-butyl, t-Bu: tert-butyl, n-Pent: normal-pentyl, CF$_3$: trifluoromethyl, OMe: methoxy, OEt: ethoxy, OCF$_3$: trifluoromethoxy, SCF$_3$: trifluoromethylthio, SMe: methylthio, NH$_2$: amino, NO$_2$: nitro, Ph: phenyl, S: sulfur atom, O: oxygen atom, Ac: acetyl, CHF$_2$: difluoromethyl.

TABLE 1

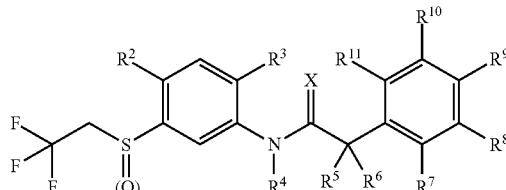

(1A)

| S. No. | R² | R³ | R⁴ | R⁵ | R⁶ | R⁷ | R⁸ | R⁹ | R¹⁰ | R¹¹ | X | n |
|---|---|---|---|---|---|---|---|---|---|---|---|---|
| 1A-1 | Me | F | H | H | H | H | H | H | H | H | O | 0 |
| 1A-2 | Me | F | H | H | H | H | H | Cl | H | H | O | 0 |
| 1A-3 | Me | F | H | H | H | Cl | H | H | H | H | O | 0 |
| 1A-4 | Me | F | H | H | H | Cl | H | H | Cl | H | O | 0 |
| 1A-5 | Me | F | H | H | H | H | Cl | Cl | H | H | O | 0 |
| 1A-6 | Me | F | H | H | H | H | Cl | H | Cl | H | O | 0 |
| 1A-7 | Me | F | H | H | H | Cl | Cl | H | H | H | O | 0 |
| 1A-8 | Me | F | H | H | H | Cl | H | Cl | H | H | O | 0 |
| 1A-9 | Me | F | H | H | H | H | Cl | H | H | H | O | 0 |
| 1A-10 | Me | F | H | H | H | H | H | t-Bu | H | H | O | 0 |
| 1A-11 | Me | F | H | H | H | Cl | H | H | H | Cl | O | 0 |
| 1A-12 | Me | F | H | H | H | H | H | CF₃ | H | H | O | 0 |
| 1A-13 | Me | F | H | H | H | H | H | F | H | H | O | 0 |
| 1A-14 | Me | F | H | H | H | H | H | OCF₃ | H | H | O | 0 |
| 1A-15 | Me | F | H | H | H | F | H | F | H | F | O | 0 |
| 1A-16 | Me | F | H | H | H | Br | H | OMe | H | H | O | 0 |
| 1A-17 | Me | F | H | H | H | H | F | H | H | H | O | 0 |
| 1A-18 | Me | F | H | H | H | F | H | H | H | H | O | 0 |
| 1A-19 | Me | F | H | H | H | H | OCF₃ | H | H | H | O | 0 |
| 1A-20 | Me | F | H | H | H | F | H | H | H | F | O | 0 |
| 1A-21 | Me | F | H | H | H | Me | H | H | H | H | O | 0 |
| 1A-22 | Me | F | H | H | H | Me | H | Me | H | Me | O | 0 |
| 1A-23 | Me | F | H | H | H | H | H | Br | H | H | O | 0 |
| 1A-24 | Me | F | H | H | H | H | H | OMe | H | H | O | 0 |
| 1A-25 | Me | F | H | H | H | H | H | OEt | H | H | O | 0 |
| 1A-26 | Me | F | H | H | H | H | H | O—n-Pr | H | H | O | 0 |
| 1A-27 | Me | F | H | H | H | H | H | 3,4-Cl₂—Ph | H | H | O | 0 |
| 1A-28 | Me | F | H | H | H | H | H | 4-OCF₃—Ph | H | H | O | 0 |
| 1A-29 | Me | F | H | H | H | H | H | 4-CF₃—Ph | H | H | O | 0 |
| 1A-30 | Me | F | H | H | H | H | H | i-Pr | H | H | O | 0 |
| 1A-31 | Me | F | H | H | H | H | H | NH₂ | H | H | O | 0 |
| 1A-32 | Me | F | H | H | H | H | H | NO₂ | H | H | O | 0 |
| 1A-33 | Me | F | H | H | i-Pr | H | H | Cl | H | H | O | 0 |
| 1A-34 | Me | F | H | Me | Me | H | H | Cl | H | H | O | 0 |
| 1A-35 | Me | F | H | H | H | H | H | Cl | H | H | O | 1 |
| 1A-36 | Me | F | H | H | H | H | H | Cl | H | H | O | 2 |
| 1A-37 | Me | F | H | H | H | H | H | OCF₃ | H | H | O | 1 |
| 1A-38 | Me | F | H | H | H | H | H | OCF₃ | H | H | O | 2 |
| 1A-39 | Me | F | H | H | H | H | H | CF₃ | H | H | O | 1 |
| 1A-40 | Me | F | H | H | H | H | H | CF₃ | H | H | O | 2 |
| 1A-41 | Me | F | Me | H | H | H | H | Cl | H | H | O | 0 |
| 1A-42 | Me | F | Me | H | H | H | H | OCF₃ | H | H | O | 0 |
| 1A-43 | Me | F | Me | H | H | H | H | CF₃ | H | H | O | 0 |
| 1A-44 | Me | Br | H | H | H | H | H | Cl | H | H | O | 0 |
| 1A-45 | Me | F | Et | H | H | H | H | Cl | H | H | O | 0 |
| 1A-46 | Me | F | H | H | H | H | H | n-Pr | H | H | O | 0 |
| 1A-47 | Me | F | H | H | H | H | H | SCF₃ | H | H | O | 0 |
| 1A-48 | Me | F | Et | H | H | H | H | OCF₃ | H | H | O | 0 |
| 1A-49 | Me | F | Me | H | H | H | H | SCF₃ | H | H | O | 0 |
| 1A-50 | Me | Br | Me | H | H | H | H | Cl | H | H | O | 0 |
| 1A-51 | Me | Br | Me | H | H | H | H | OCF₃ | H | H | O | 0 |
| 1A-52 | Me | Br | Me | H | H | H | H | CF₃ | H | H | O | 0 |
| 1A-53 | Me | Br | H | H | H | H | H | CF₃ | H | H | O | 0 |
| 1A-54 | Me | Br | H | H | H | H | H | OCF₃ | H | H | O | 0 |
| 1A-55 | Me | Cl | Et | H | H | H | H | Cl | H | H | O | 0 |
| 1A-56 | Me | Cl | Me | H | H | H | H | OCF₃ | H | H | O | 0 |
| 1A-57 | Me | Cl | Me | H | H | H | H | Cl | H | H | O | 0 |
| 1A-58 | Me | Cl | Et | H | H | H | H | OCF₃ | H | H | O | 0 |
| 1A-59 | Me | Cl | H | H | H | H | H | OCF₃ | H | H | O | 0 |
| 1A-60 | Me | Cl | H | H | H | H | H | CF₃ | H | H | O | 0 |
| 1A-61 | Me | Cl | H | H | H | H | H | Cl | H | H | O | 0 |
| 1A-62 | Me | Cl | H | H | H | H | H | SCF₃ | H | H | O | 0 |
| 1A-63 | Me | F | H | H | H | H | H | 4-Cl—Ph | H | H | O | 0 |
| 1A-64 | Me | F | H | H | H | H | H | 5-CF₃-2-Py | H | H | O | 0 |
| 1A-65 | Me | F | H | H | H | H | H | Ph | H | H | O | 0 |
| 1A-66 | Me | F | H | H | H | H | H | 3,5-F₂—Ph | H | H | O | 0 |

TABLE 1-continued (1A)

| S. No. | $R^2$ | $R^3$ | $R^4$ | $R^5$ | $R^6$ | $R^7$ | $R^8$ | $R^9$ | $R^{10}$ | $R^{11}$ | X | n |
|---|---|---|---|---|---|---|---|---|---|---|---|---|
| 1A-67 | Me | F | H | H | H | H | H | 2-SMe—Ph | H | H | O | 0 |
| 1A-68 | Me | F | H | H | H | H | H | 2-Cl—Ph | H | H | O | 0 |
| 1A-69 | Me | F | H | H | H | H | H | Me | H | H | O | 0 |
| 1A-70 | Me | F | H | H | H | H | H | Et | H | H | O | 0 |
| 1A-71 | Me | F | H | H | H | H | H | n-pent | H | H | O | 0 |
| 1A-72 | Me | F | Me | H | H | H | H | SMe | H | H | O | 0 |
| 1A-73 | Me | Br | Me | H | H | H | H | $SCF_3$ | H | H | O | 0 |
| 1A-74 | Me | Br | Me | H | H | H | H | SMe | H | H | O | 0 |
| 1A-75 | Me | Br | H | H | H | H | H | $SCF_3$ | H | H | O | 0 |
| 1A-76 | Me | F | H | H | H | H | H | SMe | H | H | O | 0 |
| 1A-77 | Me | Br | H | H | H | H | H | SMe | H | H | O | 0 |
| 1A-78 | Me | F | Et | H | H | H | H | SMe | H | H | O | 0 |
| 1A-79 | F | Me | H | H | H | H | H | Cl | H | H | O | 0 |
| 1A-80 | F | Me | H | H | H | H | H | $OCF_3$ | H | H | O | 0 |
| 1A-81 | F | Me | H | H | H | H | H | $CF_3$ | H | H | O | 0 |
| 1A-82 | Me | Cl | Me | H | H | H | H | $CF_3$ | H | H | O | 0 |
| 1A-83 | Me | Cl | Et | H | H | H | H | $CF_3$ | H | H | O | 0 |
| 1A-84 | F | Me | H | H | H | H | H | $SCF_3$ | H | H | O | 0 |
| 1A-85 | Me | Br | Et | Me | H | H | H | Cl | H | H | O | 0 |
| 1A-86 | Me | F | Me | Me | H | H | H | Cl | H | H | O | 0 |
| 1A-87 | Me | F | Et | Me | H | H | H | Cl | H | H | O | 0 |
| 1A-88 | Me | Br | Me | Me | H | H | H | Cl | H | H | O | 0 |
| 1A-89 | Me | Br | H | Me | H | H | H | Cl | H | H | O | 0 |
| 1A-90 | Me | F | H | Me | H | H | H | Cl | H | H | O | 0 |
| 1A-91 | Me | F | n-Pr | H | H | H | H | $CF_3$ | H | H | O | 0 |
| 1A-92 | Me | F | n-Bu | H | H | H | H | $CF_3$ | H | H | O | 0 |
| 1A-93 | Me | F | Me | H | H | H | H | 3,4-$Cl_2$—Ph | H | H | O | 0 |
| 1A-94 | Me | F | Et | H | H | H | H | 3,4-$Cl_2$—Ph | H | H | O | 0 |
| 1A-95 | Me | F | Me | H | H | H | H | Ph | H | H | O | 0 |
| 1A-96 | Me | F | Et | H | H | H | H | Ph | H | H | O | 0 |
| 1A-97 | Me | F | Propargyl | H | H | H | H | $CF_3$ | H | H | O | 0 |
| 1A-98 | Me | F | i-Pr | H | H | H | H | $CF_3$ | H | H | O | 0 |
| 1A-99 | F | Me | H | H | H | H | H | 4-$OCF_3$—Ph | H | H | O | 0 |
| 1A-100 | F | Me | H | H | H | H | H | 4-$CF_3$—Ph | H | H | O | 0 |
| 1A-101 | Me | F | Heptafluoro-i-Pr | H | H | H | H | $CF_3$ | H | H | O | 0 |
| 1A-102 | Me | F | H | H | H | H | H | 4-F—Ph | H | H | O | 0 |
| 1A-103 | Me | F | H | H | H | H | H | 4-OMe—Ph | H | H | O | 0 |
| 1A-104 | Me | F | H | H | H | H | H | 3-$OCF_3$—Ph | H | H | O | 0 |
| 1A-105 | Me | F | H | H | H | H | H | 3-Cl, 5-$CF_3$—Ph | H | H | O | 0 |
| 1A-106 | Me | F | H | H | H | H | H | 2-$OCF_3$—Ph | H | H | O | 0 |
| 1A-107 | Me | F | H | H | H | H | H | 3-$CF_3$—Ph | H | H | O | 0 |
| 1A-108 | Me | F | H | H | H | H | H | 3-F—Ph | H | H | O | 0 |
| 1A-109 | Me | F | H | H | H | H | H | 2-F—Ph | H | H | O | 0 |
| 1A-110 | Me | F | Me | H | H | H | H | 4-Cl, 3-$CF_3$—Ph | H | H | O | 0 |
| 1A-111 | Me | F | Me | H | H | H | H | 2-Cl, 4-F—Ph | H | H | O | 0 |
| 1A-112 | Me | F | 4,4,4-trifluoro-n-Bu | H | H | H | H | $CF_3$ | H | H | O | 0 |
| 1A-113 | Me | F | H | H | H | H | H | 2-Cl, 4-F—Ph | H | H | O | 0 |
| 1A-114 | Me | F | H | H | H | H | H | 4-Cl, 3-$CF_3$—Ph | H | H | O | 0 |
| 1A-115 | Me | F | H | H | H | H | H | 5-Pyrimidyl | H | H | O | 0 |
| 1A-116 | Me | F | H | H | H | H | H | $CF_3$ | H | H | S | 0 |
| 1A-117 | Me | F | Me | H | H | H | H | $CF_3$ | H | H | S | 0 |
| 1A-118 | Me | F | Me | H | H | H | H | 3-F—Ph | H | H | O | 0 |
| 1A-119 | Me | F | Me | H | H | H | H | 3-$CF_3$—Ph | H | H | O | 0 |
| 1A-120 | Me | F | Me | H | H | H | H | 3-Cl, 5-$CF_3$—Ph | H | H | O | 0 |
| 1A-121 | Me | F | Me | H | H | H | H | 3-$CF_3$—Ph | H | H | O | 0 |
| 1A-122 | Me | F | Me | H | H | H | H | 4-OMe—Ph | H | H | O | 0 |
| 1A-123 | Me | F | Me | H | H | H | H | 4-F—Ph | H | H | O | 0 |
| 1A-124 | Me | F | Me | H | H | H | H | 2-F—Ph | H | H | O | 0 |
| 1A-125 | Me | F | Me | H | H | H | H | 2-$OCF_3$—Ph | H | H | O | 0 |
| 1A-126 | Me | F | H | F | F | H | H | Cl | H | H | O | 0 |
| 1A-127 | Me | F | Me | H | H | H | H | 4-Cl—Ph | H | H | O | 0 |
| 1A-128 | Me | F | Me | H | H | H | H | 2-Cl—Ph | H | H | O | 0 |
| 1A-129 | Me | F | Me | F | F | H | H | Cl | H | H | O | 0 |
| 1A-130 | Me | F | Me | H | H | H | H | n-Pr | H | H | O | 0 |
| 1A-131 | Me | F | Me | H | H | H | Cl | Cl | H | H | O | 0 |

TABLE 1-continued

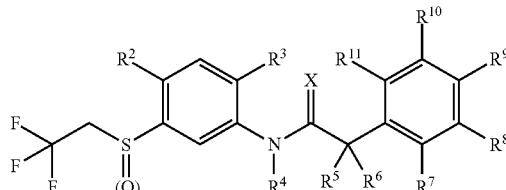

(1A)

| S. No. | R² | R³ | R⁴ | R⁵ | R⁶ | R⁷ | R⁸ | R⁹ | R¹⁰ | R¹¹ | X | n |
|---|---|---|---|---|---|---|---|---|---|---|---|---|
| 1A-132 | Me | F | Me | H | H | F | H | H | H | F | O | 0 |
| 1A-133 | Me | F | Me | H | H | H | H | Et | H | H | O | 0 |
| 1A-134 | Me | F | Et | H | H | H | H | SO₂Me | H | H | O | 0 |
| 1A-135 | Me | F | Me | H | H | H | H | SO₂Me | H | H | O | 0 |
| 1A-136 | Me | F | H | H | H | H | H | SO₂Me | H | H | O | 0 |
| 1A-137 | Me | F | H | F | F | H | H | CF₃ | H | H | O | 0 |
| 1A-138 | Me | F | Me | F | F | H | H | CF₃ | H | H | O | 0 |
| 1A-139 | Me | F | Me | H | H | H | H | CN | H | H | O | 0 |
| 1A-140 | Me | F | H | H | H | H | H | 2,4-Cl₂—Ph | H | H | O | 0 |
| 1A-141 | Me | F | H | H | H | H | H | 3,4,5-F3-Ph | H | H | O | 0 |
| 1A-142 | Me | F | H | H | H | H | H | 4-Br—Ph | H | H | O | 0 |
| 1A-143 | Me | F | H | H | H | H | H | 3,5-Cl₂—Ph | H | H | O | 0 |
| 1A-144 | Me | F | H | H | H | H | H | 4-SMe—Ph | H | H | O | 0 |
| 1A-145 | Me | F | H | H | H | H | H | 4-Me—Ph | H | H | O | 0 |
| 1A-146 | Me | F | Me | H | H | H | H | 4-SMe—Ph | H | H | O | 0 |
| 1A-147 | Me | F | Me | H | H | H | H | 3,5-Cl₂—Ph | H | H | O | 0 |
| 1A-148 | Me | F | Me | H | H | H | H | 4-Br—Ph | H | H | O | 0 |
| 1A-149 | Me | F | Me | H | H | H | H | 4-Me—Ph | H | H | O | 0 |

TABLE 2

| S. No. | ¹H NMR |
|---|---|
| 1A-1 | CDCl₃: δ 8.50 (d, J = 7.6 Hz, 1H), 7.43-7.40 (m, 2H), 7.37-7.33 (m, 3H), 7.27-7.24 (bs, 1H), 6.90 (d, J = 11.2 Hz, 1H), 3.77 (s, 2H), 3.37 (q, J = 9.6 Hz, 2H), 2.39 (s, 3H). |
| 1A-2 | CDCl₃: δ 8.47 (d, J = 8.0 Hz, 1H), 7.39-7.37 (m, 2H), 7.29-7.27 (m, 2H), 7.24 (bs, 1H), 6.93 (d, J = 11.6 Hz, 1H), 3.73 (s, 2H), 3.37 (q, J = 9.6 Hz, 2H), 2.40 (s, 3H). |
| 1A-3 | CDCl₃: δ 8.59 (d, J = 8.0 Hz, 1H), 7.47-7.41 (m, 3H), 7.33-7.28 (m, 2H), 6.92 (d, J = 11.6 Hz, 1H), 3.89 (s, 2H), 3.37 (q, J = 9.7 Hz, 2H), 2.40 (s, 3H). |
| 1A-4 | CDCl₃: δ 8.47 (d, J = 8.0 Hz, 1H), 7.42-6.42 (m, 2H), 7.28-7.26 (m, 2H), 6.95 (d, J = 11.6 Hz, 1H), 3.84 (s, 2H), 3.37 (q, J = 9.6 Hz, 2H), 2.41 (s, 3H). |
| 1A-5 | DMSO-d₆: δ 10.02 (s, 1H), 8.06 (d, J = 7.6 Hz, 1H), 7.60 (d, J = 4.0 Hz, 2H), 7.32 (d, J = 8.0 Hz, 1H), 7.25 (d, J = 11.6 Hz, 1H), 3.82-3.76 (m, 4H), 2.37 (s, 3H). |
| 1A-6 | CDCl₃: δ 8.47 (d, J = 8.0 Hz, 1H), 7.34 (s, 1H), 7.26-7.25 (m, 3H), 7.96 (d, J = 11.6 Hz, 1H), 3.70 (s, 2H), 3.37 (q, J = 9.6 Hz, 2H), 2.42 (s, 3H). |
| 1A-7 | CDCl₃: δ 8.47 (d, J = 7.6 Hz, 1H), 7.46 (d, J = 9.2 Hz, 1H), 7.39 (bs, 1H), 7.33 (d, J = 6.8 Hz, 1H), 7.27-7.23 (m, 1H), 6.95 (d, J = 11.2 Hz, 1H), 3.93 (s, 2H), 3.37 (q, J = 9.6 Hz, 2H), 2.41 (s, 3H). |
| 1A-8 | CDCl₃: δ 8.47 (d, J = 8.0 Hz, 1H), 7.47 (d, J = 2.0 Hz, 1H), 7.38 (bs, 1H), 7.36 (d, J = 8.6 Hz, 1H), 7.29 (d, J = 8.4 Hz, 1H), 6.95 (d, J = 11.6 Hz, 1H), 3.85 (s, 2H), 3.37 (q, J = 9.6 Hz, 2H), 2.41 (s, 3H). |
| 1A-9 | CDCl₃: δ 8.48 (d, J = 8.0 Hz, 1H), 7.32 (m, 3H), 7.26-7.23 (m, 2H), 6.93 (d, J = 11.6 Hz, 1H), 3.73 (s, 2H), 3.37 (q, J = 9.7 Hz, 2H), 2.41 (s, 3H). |
| 1A-10 | CDCl₃: δ 8.50 (d, J = 8.0 Hz, 1H), 7.42 (d, J = 8.4 Hz, 2H), 7.28-7.25 (m, 3H), 6.90 (d, J = 11.2 Hz, 1H), 3.73 (s, 2H), 3.37 (q, J = 9.7 Hz, 2H), 2.39 (s, 3H), 1.33 (s, 9H). |
| 1A-11 | CDCl₃: δ 8.50 (d, J = 8.0 Hz, 1H), 7.40 (d, J = 8.0 Hz, 2H), 7.37 (bs, 1H), 7.22 (d, J = 8.4 Hz, 1H), 6.94 (d, J = 11.6 Hz, 1H), 4.14 (s, 2H), 3.37 (q, J = 9.7 Hz, 2H), 2.41 (s, 3H). |
| 1A-12 | CDCl₃: δ 8.47 (d, J = 8.0 Hz, 1H), 7.66 (d, J = 8.0 Hz, 2H), 7.48 (d, J = 8.0 Hz, 2H), 7.27 (bs, 1H), 6.94 (d, J = 11.2 Hz, 1H), 3.82 (s, 2H), 3.37 (q, J = 9.6 Hz, 2H), 2.41 (s, 3H). |
| 1A-13 | CDCl₃: δ 8.49 (d, J = 7.6 Hz, 1H), 7.33-7.29 (m, 2H), 7.23 (bs, 1H), 7.10 (t, J = 8.6 Hz, 2H), 6.92 (d, J = 11.6 Hz, 1H), 3.74 (s, 2H), 3.37 (q, J = 9.6 Hz, 2H), 2.40 (s, 3H). |
| 1A-14 | CDCl₃: δ 8.48 (d, J = 8.0 Hz, 1H), 7.38 (d, J = 8.4 Hz, 2H), 7.27-7.24 (m, 3H), 6.94 (d, J = 11.6 Hz, 1H), 3.76 (s, 2H), 3.37 (q, J = 9.6 Hz, 2H), 2.41 (s, 3H). |
| 1A-15 | CDCl₃: δ 8.49 (d, J = 7.6 Hz, 1H), 7.40 (bs, 1H), 6.97 (d, J = 11.6 Hz, 1H), 6.75 (t, J = 7.8 Hz, 2H), 3.77 (s, 2H), 3.36 (q, J = 9.6 Hz, 2H), 2.42 (s, 3H). |
| 1A-16 | CDCl₃: δ 8.49 (d, J = 7.6 Hz, 1H), 7.38 (bs, 1H), 7.32 (d, J = 8.4 Hz, 1H), 7.18 (d, J = 2.8 Hz, 1H), 6.94-6.89 (m, 2H), 3.83 (s, 2H), 3.81 (s, 3H), 3.38 (q, J = 9.6 Hz, 2H), 2.40 (s, 3H). |
| 1A-17 | CDCl₃: δ 8.48 (d, J = 7.6 Hz, 1H), 7.38 (q, J = 7.0 Hz, 1H), 7.12 (d, J = 7.6 Hz, 2H), 7.07-7.03 (m, 2H), 6.92 (d, J = 11.6 Hz, 1H), 3.76 (s, 2H), 3.37 (q, J = 9.6 Hz, 2H), 2.40 (s, 3H). |
| 1A-18 | CDCl₃: δ 8.49 (d, J = 7.6 Hz, 1H), 7.40-7.31 (m, 3H), 7.20-7.11 (m, 2H), 6.93 (d, J = 11.6 Hz, 1H), 3.78 (s, 2H), 3.37 (q, J = 9.6 Hz, 2H), 2.40 (s, 3H). |
| 1A-19 | CDCl₃: δ 8.50 (d, J = 8.0 Hz, 1H), 7.43 (bs, 1H), 7.32-7.28 (m, 2H), 6.99-6.94 (m, 3H), 3.83 (s, 2H), 3.36 (q, J = 9.6 Hz, 2H), 2.41 (s, 3H). |
| 1A-20 | CDCl₃: δ 8.48 (d, J = 8.0 Hz, 1H), 7.44 (t, J = 8.4 Hz, 1H), 7.29 (d, J = 8.0 Hz, 1H), 7.22-7.20 (m, 2H), 6.93 (d, J = 11.6 Hz, 1H), 3.78 (s, 2H), 3.37 (q, J = 9.7 Hz, 2H), 2.41 (s, 3H). |

TABLE 2-continued

| S. No. | ¹H NMR |
|---|---|
| 1A-21 | CDCl₃: δ 8.47 (d, J = 8.0 Hz, 1H), 7.28-7.26 (m, 4H), 7.18 (bs, 1H), 6.88 (d, J = 11.2 Hz, 1H), 3.78 (s, 2H), 3.38 (q, J = 9.6 Hz, 2H), 2.39 (s, 3H), 2.35 (s, 3H). |
| 1A-22 | CDCl₃: δ 8.43 (d, J = 7.6 Hz, 1H), 7.18 (bs, 1H), 6.95 (s, 2H), 6.87 (d, J = 11.2 Hz, 1H), 3.77 (s, 2H), 3.38 (q, J = 9.6 Hz, 2H), 2.39 (s, 3H), 2.31-2.30 (m, 9H). |
| 1A-23 | CDCl₃: δ 8.47 (d, J = 8.0 Hz, 1H), 7.53 (d, J = 8.0 Hz, 2H), 7.26-7.21 (m, 3H), 6.93 (d, J = 11.6 Hz, 1H), 3.71 (s, 2H), 3.37 (q, J = 9.7 Hz, 2H), 2.40 (s, 3H). |
| 1A-24 | CDCl₃: δ 8.49 (d, J = 7.6 Hz, 1H), 7.27-7.24 (m, 3H), 6.94 (d, J = 8.4 Hz, 2H), 6.90 (d, J = 11.6 Hz, 1H), 3.83 (s, 3H), 3.70 (s, 2H), 3.38 (q, J = 9.6 Hz, 2H), 2.39 (s, 3H). |
| 1A-25 | CDCl₃: δ 8.49 (d, J = 8.0 Hz, 1H), 7.28-7.22 (m, 3H), 6.94-6.88 (m, 3H), 4.07-4.02 (m, 2H), 3.70 (s, 2H), 3.38 (q, J = 9.6 Hz, 2H), 2.39 (s, 3H), 1.43 (t, J = 8.0 Hz, 3H). |
| 1A-26 | CDCl₃: δ 8.49 (d, J = 7.6 Hz, 1H), 7.28-7.22 (m, 3H), 6.94-6.88 (m, 3H), 3.93 (t, J = 6.6 Hz, 2H), 3.70 (s, 2H), 3.38 (q, J = 8.8 Hz, 2H), 2.39 (s, 3H), 1.86-1.17 (m, 2H), 1.04 (s, 3H). |
| 1A-27 | CDCl₃: δ 8.50 (d, J = 8.0 Hz, 1H), 7.68 (d, J = 1.6 Hz, 1H), 7.58 (d, J = 8.4 Hz, 2H), 7.51 (d, J = 8.4 Hz, 1H), 7.44-7.41 (m, 3H), 7.29 (bs, 1H), 6.92 (d, J = 11.2 Hz, 1H), 3.81 (s, 2H), 3.38 (q, J = 9.6 Hz, 2H), 2.40 (s, 3H). |
| 1A-28 | CDCl₃: δ 8.51 (d, J = 7.6 Hz, 1H), 7.62-7.59 (m, 4H), 7.42 (d, J = 8.4 Hz, 2H), 7.30 (d, J = 8.0 Hz, 3H), 6.92 (d, J = 11.6 Hz, 1H), 3.81 (s, 2H), 3.38 (q, J = 9.6 Hz, 2H), 2.40 (s, 3H). |
| 1A-29 | CDCl₃: δ 8.51 (d, J = 7.6 Hz, 1H), 7.70 (bs, 4H), 7.65 (d, J = 8.0 Hz, 2H), 7.45 (d, J = 8.0 Hz, 2H), 7.32 (bs, 1H), 6.92 (d, J = 11.6 Hz, 1H), 3.82 (s, 2H), 3.38 (q, J = 9.6 Hz, 2H), 2.40 (s, 3H). |
| 1A-30 | CDCl₃: δ 8.48 (d, J = 8.0 Hz, 1H), 7.00-6.73 (m, 5H), 6.89 (d, J = 7.6 Hz, 1H), 3.73 (s, 2H), 3.37 (q, J = 9.6 Hz, 2H), 2.96-2.89 (m, 1H), 2.39 (s, 3H), 1.26 (d, J = 6.8 Hz, 6H). |
| 1A-31 | CDCl₃: δ 8.49 (d, J = 8.0 Hz, 1H), 7.31 (bs, 1H), 7.10 (d, J = 8.4 Hz, 2H), 6.89 (d, J = 11.6 Hz, 1H), 6.72 (d, J = 8.4 Hz, 2H), 3.72 (bs, 2H), 3.65 (s, 2H), 3.38 (q, J = 9.6 Hz, 2H), 2.39 (s, 3H). |
| 1A-32 | CDCl₃: δ 8.46 (d, J = 8.0 Hz, 1H), 8.26 (d, J = 8.0 Hz, 1H), 7.54 (d, J = 8.4 Hz, 2H), 7.31 (bs, 1H), 6.96 (d, J = 11.6 Hz, 1H), 3.86 (s, 2H), 3.36 (q, J = 9.6 Hz, 2H), 2.42 (s, 3H). |
| 1A-33 | CDCl₃: δ 8.49 (d, J = 8.0 Hz, 1H), 7.35-7.28 (m, 5H), 6.93 (d, J = 11.2 Hz, 1H), 3.37 (q, J = 9.6 Hz, 2H), 2.99 (d, J = 10.0 Hz, 1H), 2.48-2.40 (m, 4H), 1.10 (d, J = 6.8 Hz, 3H), 0.75 (d, J = 6.8 Hz, 3H). |
| 1A-34 | CDCl₃: δ 7.38 (s, 1H), 7.32 (d, J = 3.6 Hz, 2H), 7.22 (d, J = 8.8 Hz, 2H), 7.02 (d, J = 8.8 Hz, 2H), 3.42-2.25 (m, 2H), 2.09 (s, 3H), 1.59 (s, 3H), 1.44 (s, 3H). |
| 1A-35 | CDCl₃: δ 8.77 (d, J = 7.6 Hz, 1H), 7.38 (d, J = 8.0 Hz, 2H), 7.32-7.21 (m, 3H), 6.98 (d, J = 11.2 Hz, 1H), 3.75 (s, 2H), 3.61-3.50 (m, 1H), 3.44-3.33 (m, 1H), 2.37 (s, 3H). |
| 1A-36 | CDCl₃: δ 8.96 (d, J = 7.6 Hz, 1H), 7.39 (d, J = 8.4 Hz, 2H), 7.29-7.26 (m, 3H), 7.07 (d, J = 11.2 Hz, 1H), 3.91 (q, J = 8.8 Hz, 2H), 3.76 (s, 2H), 2.64 (s, 3H). |
| 1A-37 | CDCl₃: δ 8.79 (d, J = 7.6 Hz, 1H), 7.38 (d, J = 8.8 Hz, 2H), 7.32 (bs, 1H), 7.26-7.24 (m, 2H), 6.98 (d, J = 10.8 Hz, 1H), 3.78 (s, 2H), 3.58-3.50 (m, 1H), 3.44-3.33 (m, 1H), 2.38 (s, 3H). |
| 1A-38 | CDCl₃: δ 8.97 (d, J = 7.6 Hz, 1H), 7.38 (d, J = 8.4 Hz, 2H), 7.29-7.25 (m, 3H), 7.07 (d, J = 10.8 Hz, 1H), 3.90 (q, J = 8.9 Hz, 2H), 3.79 (s, 2H), 2.65 (s, 3H). |
| 1A-39 | CDCl₃: δ 8.78 (d, J = 7.6 Hz, 1H), 7.66 (d, J = 8.0 Hz, 2H), 7.48 (d, J = 8.0 Hz, 2H), 7.35 (bs, 1H), 6.99 (d, J = 11.2 Hz, 1H), 3.84 (s, 2H), 3.60-3.49 (m, 1H), 3.44-3.32 (m, 1H), 2.38 (s, 3H). |
| 1A-40 | CDCl₃: δ 8.96 (d, J = 9.5 Hz, 1H), 7.67 (d, J = 8.0 Hz, 2H), 7.48 (d, J = 7.6 Hz, 2H), 7.31 (bs, 1H), 7.08 (d, J = 11.2 Hz, 1H), 3.90 (q, J = 8.9 Hz, 2H), 3.85 (s, 2H), 2.65 (s, 3H). |
| 1A-41 | CDCl₃: δ 7.26 (s, 1H), 7.21 (d, J = 8.4 Hz, 2H), 7.07 (d, J = 10.0 Hz, 1H), 6.96 (d, J = 8.4 Hz, 2H), 3.45-3.34 (m, 2H), 3.28-3.21 (m, 5H), 2.51 (s, 3H). |
| 1A-42 | CDCl₃: δ 7.30 (d, J = 7.6 Hz, 1H), 7.10-7.04 (m, 5H), 3.48-3.38 (m, 2H), 3.29-3.17 (m, 5H), 2.51 (s, 3H). |
| 1A-43 | CDCl₃: δ 7.53 (d, J = 8.0 Hz, 2H), 7.32 (d, J = 7.6 Hz, 2H), 7.19 (d, J = 7.6 Hz, 2H), 7.11 (d, J = 10.4 Hz, 1H), 3.49 (q, J = 13.2 Hz, 2H), 3.30-3.23 (m, 5H), 2.54 (s, 3H). |
| 1A-44 | CDCl₃: δ 8.49 (s, 1H), 7.53 (s, 1H), 7.39 (d, J = 8.4 Hz, 2H), 7.31 (d, J = 11.2 Hz, 2H), 7.26 (s, 1H), 3.76 (s, 2H), 3.44 (q, J = 9.6 Hz, 2H), 2.35 (s, 3H). |
| 1A-45 | CDCl₃: δ 7.22-7.19 (m, 3H), 7.07 (d, J = 10.0 Hz, 1H), 6.95 (d, J = 8.4 Hz, 2H), 3.74-3.66 (m, 2H), 3.42 (s, 2H), 3.26-3.19 (m, 2H), 2.51 (s, 3H), 0.84 (t, J = 8.8 Hz, 3H). |
| 1A-46 | CDCl₃: δ 8.50 (d, J = 8.0 Hz, 1H), 7.20-7.26 (m, 5H), 6.88 (d, J = 11.6 Hz, 1H), 3.73 (s, 2H), 3.41-3.34 (m, 2H), 2.58 (t, J = 7.6 Hz, 2H), 2.39 (s, 3H), 1.68-1.60 (m, 2H), 0.94 (t, J = 7.2 Hz, 3H). |
| 1A-47 | CDCl₃: δ 8.47 (d, J = 8.0 Hz, 1H), 7.68 (d, J = 8.0 Hz, 2H), 7.40 (d, J = 8.0 Hz, 2H), 7.29 (bs, 1H), 6.93 (d, J = 11.2 Hz, 1H), 3.79 (s, 2H), 3.33 (q, J = 9.6 Hz, 2H), 2.41 (s, 3H). |
| 1A-48 | CDCl₃: δ 7.26 (d, J = 6.4 Hz, 1H), 7.09-7.04 (m, 5H), 3.77-3.63 (m, 2H), 3.44-3.34 (m, 2H), 3.29-3.20 (m, 2H), 2.48 (s, 3H), 0.86 (t, J = 9.6 Hz, 3H). |
| 1A-49 | CDCl3: δ 7.51 (d, J = 8.0 Hz, 2H), 7.31 (d, J = 7.6 Hz, 1H), 7.08 (d, J = 8.0 Hz, 2H), 7.04 (d, J = 14.4 Hz, 1H), 3.48 (s, 2H), 3.29-3.22 (s, 5H), 2.51 (s, 3H). |
| 1A-50 | CDCl3: δ 7.58 (s, 1H), 7.51 (d, J = 8.0 Hz, 2H), 7.29 (s, 1H), 7.19-7.18 (m, 2H), 3.46 (d, J = 14.8 Hz, 1H), 3.37 (d, J = 14.8 Hz, 1H), 3.29-3.22 (m, 2H), 3.19 (s, 3H), 2.48 (s, 3H). |
| 1A-51 | CDCl3: δ 7.57 (s, 1H), 7.21 (s, 1H), 7.09 (s, 4H), 3.40 (d, J = 15.2 Hz, 1H), 3.32-3.25 (m, 3H), 3.19 (s, 3H), 2.48 (s, 3H). |
| 1A-52 | CDCl₃: δ 7.57 (s, 1H), 7.21 (d, J = 8.4 Hz, 2H), 7.16 (s, 1H), 6.98 (d, J = 8.4 Hz, 2H), 4.77 (d, J = 15.2 Hz, 1H), 3.30-3.24 (m, 3H), 3.18 (s, 3H), 2.47 (s, 3H). |
| 1A-53 | CDCl₃: δ 8.48 (s, 1H), 7.68 (d, J = 8.0 Hz, 2H), 7.50 (d, J = 8.0 Hz, 3H), 7.33 (s, 1H), 3.84 (d, J = 8.0 Hz, 2H), 3.45 (q, J = 9.6 Hz, 2H), 2.36 (s, 3H). |
| 1A-54 | CDCl₃: δ 8.50 (s, 1H), 7.52 (bs, 1H), 7.40 (d, J = 8.4 Hz, 2H), 7.32-7.26 (m, 3H), 3.80 (s, 2H), 3.45 (q, J = 9.4 Hz, 2H), 2.35 (s, 3H). |
| 1A-55 | CDCl₃: δ 7.40 (s, 1H), 7.21 (d, J = 8.4 Hz, 2H), 7.11 (s, 1H), 6.96 (d, J = 8.0 Hz, 2H), 4.04-3.95 (m, 1H), 3.43-3.35 (m, 2H), 3.28-3.18 (m, 3H), 2.48 (s, 3H), 1.09 (t, J = 7.2 Hz, 3H). |
| 1A-56 | CDCl₃: δ 7.39 (s, 1H), 7.30 (s, 1H), 7.11-7.05 (m, 4H), 3.42-3.25 (m, 4H), 3.19 (s, 3H), 2.48 (s, 3H). |
| 1A-57 | CDCl₃: δ 7.39 (s, 1H), 7.21 (d, J = 8.4 Hz, 2H), 7.17 (s, 1H), 6.97 (d, J = 8.4 Hz, 2H), 3.38 (d, J = 15.2 Hz, 1H), 3.27 (q, J = 9.6 Hz, 3H), 3.18 (s, 3H), 2.48 (s, 3H). |
| 1A-58 | CDCl₃: δ 7.40 (s, 1H), 7.17 (s, 1H), 7.10-7.05 (m, 4H), 4.01-3.99 (m, 1H), 3.42-3.37 (m, 2H), 3.30-3.22 (m, 3H), 2.49 (s, 3H), 1.10 (t, J = 7.2 Hz, 3H). |
| 1A-59 | CDCl3: δ 8.53 (s, 1H), 7.54 (bs, 1H), 7.40 (d, J = 8.4 Hz, 2H), 7.28-7.26 (m, 2H), 7.16 (s, 1H), 3.80 (s, 2H), 3.44 (q, J = 9.6 Hz, 2H), 2.36 (s, 3H). |
| 1A-60 | CDCl₃: δ 8.51 (s, 1H), 7.68 (d, J = 8.0 Hz, 2H), 7.54 (bs, 1H), 7.49 (d, J = 8.4 Hz, 2H), 7.18 (s, 1H), 3.85 (s, 2H), 3.44 (q, J = 9.6 Hz, 2H), 2.36 (s, 3H). |

TABLE 2-continued

| S. No. | ¹H NMR |
|---|---|
| 1A-61 | CDCl₃: δ 8.52 (s, 1H), 7.55 (bs, 1H), 7.39 (d, J = 8.4 Hz, 2H), 7.29 (d, J = 8.4 Hz, 2H), 7.17 (s, 1H), 3.76 (s, 2H), 3.44 (q, J = 9.6 Hz, 2H), 2.36 (s, 3H). |
| 1A-62 | CDCl₃: δ 8.53 (s, 1H), 7.71 (d, J = 8.0 Hz, 2H), 7.52 (bs, 1H), 7.43 (d, J = 8.0 Hz, 2H), 7.16 (s, 1H), 3.82 (s, 2H), 3.44 (q, J = 9.6 Hz, 2H), 2.36 (s, 3H). |
| 1A-63 | CDCl₃: δ 8.47 (d, J = 7.6 Hz, 1H), 7.60-7.52 (m, 3H), 7.41 (d J = 8.4 Hz, 2H), 7.26-7.21 (m, 4H), 6.95-6.90 (m, 1H), 3.71 (s, 2H), 3.37 (q, J = 9.8 Hz, 2H), 2.40 (s, 3H). |
| 1A-64 | CDCl3: δ 8.50 (d, J = 8.0 Hz, 1H), 8.44 (s, 1H), 7.92 (d, J = 8.4 Hz, 1H), 7.41 (d, J = 8.4 Hz, 2H), 7.31 (bs, 1H), 7.20 (d, J = 8.4 Hz, 2H), 7.04 (d, J = 8.8 Hz, 1H), 6.94 (d, J = 11.6 Hz, 1H), 3.79 (s, 2H), 3.38 (q, J = 9.6 Hz, 2H), 2.41 (s, 3H). |
| 1A-65 | CDCl₃: δ 8.51 (d, J = 8.0 Hz, 1H), 7.65-7.60 (m, 3H), 7.48-7.35 (m, 5H), 7.32 (bs, 1H), 6.91 (d, J = 11.6 Hz, 2H), 3.81 (s, 2H), 3.38 (q, J = 9.6 Hz, 2H), 2.40 (s, 3H). |
| 1A-66 | CDCl₃: δ 8.50 (d, J = 8.0 Hz, 1H), 7.59 (d, J = 8.4 Hz, 2H), 7.44 (d, J = 8.0 Hz, 2H), 7.30 (bs, 1H), 7.11 (d, J = 8.8 Hz, 2H), 6.93 (d, J = 11.2 Hz, 1H), 6.82-6.78 (m, 1H), 3.81 (s, 2H), 3.38 (q, J = 9.7 Hz, 2H), 2.40 (s, 3H). |
| 1A-67 | CDCl₃: δ 8.52 (d, J = 8.0 Hz, 1H), 7.47 (d, J = 8.0 Hz, 2H), 7.40 (d, J = 8.0 Hz, 2H), 7.41-7.21 (m, 5H), 6.92 (d, J = 11.2 Hz, 1H), 3.82 (s, 2H), 3.39 (q, J = 9.7 Hz, 2H), 2.41 (s, 3H), 2.37 (s, 3H). |
| 1A-68 | CDCl₃: δ 8.52 (d, J = 8.0 Hz, 1H), 7.50-7.47 (m, 3H), 7.41 (d, J = 8.0 Hz, 2H), 7.35-7.29 (m, 4H), 6.92 (d, J = 11.6 Hz, 1H), 3.82 (s, 2H), 3.38 (q, J = 9.6 Hz, 2H), 2.41 (s, 3H). |
| 1A-69 | CDCl₃: δ 8.49 (d, J = 7.6 Hz, 1H), 7.26 (bs, 1H), 7.22-7.51 (m, 4H), 6.89 (d, J = 11.6 Hz, 1H), 3.72 (s, 2H), 3.38 (q, J = 9.6 Hz, 2H), 2.39 (s, 3H), 2.38 (s, 3H). |
| 1A-70 | CDCl₃: δ 8.49 (d, J = 8.0 Hz, 1H), 7.28-7.12 (m, 5H), 6.99 (d, J = 11.2 Hz, 1H), 3.73 (s, 2H), 3.37 (q, J = 9.6 Hz, 2H), 2.67 (q, J = 7.6 Hz, 2H), 2.39 (s, 3H), 1.25 (m, 3H). |
| 1A-71 | CDCl₃: δ 8.50 (d, J = 8.0 Hz, 1H), 7.28-7.22 (m, 5H), 6.89 (d, J = 11.6 Hz, 1H), 3.73 (s, 2H), 3.38 (q, J = 9.7 Hz, 2H), 2.62 (t, J = 8.0 Hz, 2H), 2.39 (s, 3H), 1.66-1.58 (m, 2H), 1.28-1.36 (m, 4H), 0.91-0.80 (m, 3H). |
| 1A-72 | CDCl₃: δ 7.23 (d, J = 7.6 Hz, 1H), 7.13 (d, J = 8.0 Hz, 2H), 7.07 (d, J = 10.4 Hz, 1H), 6.94 (d, J = 8.4 Hz, 2H), 3.46-3.33 (m, 2H), 3.26-3.19 (m, 5H), 2.50 (s, 3H), 2.45 (s, 3H). |
| 1A-73 | CDCl₃: δ 7.57 (s, 1H), 7.53 (d, J = 8.0 Hz, 2H), 7.22 (s, 1H), 7.12 (d, J = 8.4 Hz, 2H), 3.45-3.26 (m, 4H), 3.19 (s, 3H), 2.48 (s, 3H). |
| 1A-74 | CDCl₃: δ 7.56 (s, 1H), 7.13 (d, J = 8.4 Hz, 2H), 7.08 (s, 1H), 6.95 (d, J = 8.4 Hz, 2H), 3.42-3.38 (m, 1H), 3.27-3.19 (m, 3H), 3.17 (s, 3H), 2.46 (s, 3H), 2.45 (s, 3H). |
| 1A-75 | CDCl₃: δ 8.50 (s, 1H), 7.72 (d, J = 8.0 Hz, 2H), 7.50 (bs, 1H), 7.44 (d, J = 8.0 Hz, 2H), 7.32 (s, 1H), 3.83 (s, 2H), 3.45 (q, J = 9.4 Hz, 2H), 2.35 (s, 3H). |
| 1A-76 | CDCl3: δ 8.478 (d, J = 7.6 Hz, 1H), 7.242-7.298 (m, 5H), 6.911 (d, J = 11.6 Hz, 1H), 3.719 (s, 2H), 3.373 (q, J = 9.6 Hz, 2H), 2.497 (s, 3H), 2.398 (s, 3H). |
| 1A-77 | CDCl₃: δ 8.50 (s, 1H), 7.58 (bs, 1H), 7.32-7.29 (m, 5H), 3.74 (s, 2H), 3.46 (q, J = 9.6 Hz, 2H), 2.50 (s, 3H), 2.35 (s, 3H). |
| 1A-78 | CDCl₃: δ 7.16 (d, J = 7.6 Hz, 1H), 7.13 (d, J = 8.0 Hz, 2H), 7.08 (d, J = 10.0 Hz, 1H), 6.93 (d, J = 8.0 Hz, 2H), 3.76-3.62 (m, 2H), 3.41 (d, J = 14.8 Hz, 1H), 3.30 (d, J = 14.8 Hz, 1H), 3.20 (q, J = 9.6 Hz, 2H), 2.51 (s, 3H), 2.45 (s, 3H), 1.08 (t, J = 7.2 Hz, 3H). |
| 1A-79 | CDCl₃: δ 7.95 (d, J = 7.6 Hz, 1H), 7.40 (d, J = 8.4 Hz, 2H), 7.30 (d, J = 8.4 Hz, 2H), 8.90 (d, J = 9.2 Hz, 1H), 8.75 (bs, 1H), 3.75 (s, 2H), 3.50 (q, J = 9.6 Hz, 2H), 1.93 (s, 3H). |
| 1A-80 | CDCl₃: δ 7.98 (d, J = 7.6 Hz, 1H), 7.40 (d, J = 8.4 Hz, 2H), 7.29-7.27 (m, 2H), 8.90 (d, J = 9.2 Hz, 1H), 8.75 (bs, 1H), 3.78 (s, 2H), 3.39 (q, J = 9.6 Hz, 2H), 1.98 (s, 3H). |
| 1A-81 | CDCl₃: δ 7.92 (d, J = 6.8 Hz, 1H), 7.69 (d, J = 8.4 Hz, 2H), 7.50 (d, J = 8.0 Hz, 2H), 6.91 (d, J = 9.6 Hz, 1H), 6.75 (bs, 1H), 3.83 (s, 2H), 3.39 (q, J = 9.6 Hz, 2H), 2.02 (s, 3H). |
| 1A-82 | CDCl₃: δ 7.51 (d, J = 8.4 Hz, 2H), 7.40 (s, 1H), 7.21 (s, 1H), 7.17 (d, J = 8.4 Hz, 2H), 3.43 (d, J = 16.0 Hz, 1H), 3.36 (d, J = 15.6 Hz, 1H), 3.30-3.20 (m, 2H), 3.17 (s, 3H), 2.48 (s, 3H). |
| 1A-83 | CDCl₃: δ 7.50 (d, J = 8.0 Hz, 2H), 7.42 (s, 1H), 7.16 (d, J = 8.4 Hz, 2H), 7.14 (s, 1H), 4.05-3.96 (m, 1H), 3.47-3.31 (m, 3H), 3.23 (q, J = 9.4 Hz, 2H), 2.49 (s, 3H), 1.24 (t, J = 7.2 Hz, 3H). |
| 1A-84 | CDCl₃: δ 8.00 (d, J = 8.4 Hz, 1H), 7.72 (d, J = 7.6 Hz, 2H), 7.44 (d, J = 8.0 Hz, 2H), 6.88 (d, J = 9.6 Hz, 1H), 6.74 (bs, 1H), 3.81 (s, 2H), 3.39 (q, J = 9.4 Hz, 2H), 1.96 (s, 3H). |
| 1A-85 | CDCl₃: δ 7.56 (s, 1H), 7.20 (d, J = 8.4 Hz, 2H), 6.89 (d, J = 8.4 Hz, 2H), 6.56 (s, 1H), 4.07-3.96 (m, 1H), 3.25-3.37 (m, 3H), 3.08-2.97 (m, 2H), 2.46 (s, 3H), 1.37 (t, J = 6.8 Hz, 3H), 1.06 (t, J = 7.2 Hz, 3H). |
| 1A-86 | CDCl₃: δ 7.83 (d, J = 8.0 Hz, 1H), 7.27-7.24 (m, 3H), 6.98 (d, J = 8.4 Hz, 1H), 6.86 (d, J = 8.0 Hz, 1H), 4.14-3.97 (m, 1H), 3.92-3.49 (m, 2H), 3.05 (s, 3H), 2.38 (s, 3H), 1.25 (d, J = 6.8 Hz, 3H). |
| 1A-87 | CDCl₃: δ 7.20-7.09 (m, 3H), 6.94-6.75 (m, 3H), 3.91-3.30 (m, 4H), 3.08-3.04 (m, 1H), 3.52-3.49 (m, 3H), 1.37-1.35 (m, 3H), 1.05 (t, J = 6.8 Hz, 3H). |
| 1A-88 | CDCl₃: δ 7.56 (s, 1H), 7.20 (d, J = 8.4 Hz, 2H), 6.91 (d, J = 8.4 Hz, 2H), 6.68 (s, 1H), 3.34-3.29 (m, 1H), 3.15 (s, 3H), 3.05 (q, J = 9.4 Hz, 2H), 2.44 (s, 3H), 1.38 (d, J = 6.8 Hz, 3H). |
| 1A-89 | CDCl₃: 8.48 (s, 1H), 7.50 (bs, 1H), 7.38 (d, J = 8.4 Hz, 2H), 7.32 (d, J = 8.8 Hz, 3H), 3.71 (q, J = 7.2 Hz, 1H), 3.46 (q, J = 9.6 Hz, 2H), 2.35 (s, 3H), 1.62 (d, J = 6.8 Hz, 3H). |
| 1A-90 | CDCl₃: δ 8.48 (d, J = 8.0 Hz, 1H), 7.36 (d, J = 8.4 Hz, 2H), 7.31 (d, J = 8.4 Hz, 2H), 7.18 (bs, 1H), 6.91 (d, J = 11.6 Hz, 1H), 3.71 (q, J = 7.2 Hz, 1H), 3.38 (q, J = 9.6 Hz, 2H), 2.40 (s, 3H), 1.59 (d, J = 6.8 Hz, 3H). |
| 1A-91 | CDCl₃: δ 8.50 (d, J = 8.0 Hz, 2H), 7.23 (d, J = 8.4 Hz, 1H), 7.15 (d, J = 8.0 Hz, 2H), 7.08 (d, J = 10.0 Hz, 1H), 3.68-3.40 (m, 4H), 3.25-3.17 (m, 2H), 2.51 (s, 2H), 1.50-1.41 (m, 3H), 0.90-0.84 (m, 3H). |
| 1A-92 | CDCl₃: δ 7.49 (d, J = 8.0 Hz, 2H), 7.20 (d, J = 7.6 Hz, 1H), 7.15 (d, J = 8.0 Hz, 2H), 7.09 (d, J = 10.0 Hz, 1H), 3.73-3.66 (m, 2H), 3.62-3.54 (m, 2H), 3.25-3.18 (m, 2H), 2.52 (s, 3H). 1.46-1.41 (m, 2H) 1.32-1.22 (m, 2H), 0.862 (t, J = 7.6 Hz, 3H) |
| 1A-93 | CDCl₃: δ 7.63 (d, J = 3.0 Hz, 1H), 7.48 (d, J = 8.4 Hz, 1H), 7.42 (d, J = 8.0 Hz, 2H), 7.36 (s, 1H), 7.30 (d, J = 7.2 Hz, 1H), 7.13-7.08 (m, 3H), 3.53-3.42 (m, 2H), 3.26-3.20 (m, 5H), 2.52 (s, 3H). |
| 1A-94 | CDCl₃: δ 7.63 (d, J = 2.4 Hz, 1H), 7.48 (d, J = 8.4 Hz, 1H), 7.40-7.36 (m, 3H), 7.24 (d, J = 8.4 Hz, 1H), 7.12-7.09 (m, 3H), 3.78-3.65 (m, 2H), 3.50-3.37 (m, 2H), 3.25-3.17 (m, 2H), 2.52 (s, 3H). 1.10 (t, J = 7.2 Hz, 3H). |
| 1A-95 | CDCl₃: δ 7.55 (d, J = 7.6 Hz, 2H), 7.47 (d, J = 8.0 Hz, 2H), 7.42 (t, J = 7.6 Hz, 2H), 7.33 (t, J = 7.2 Hz, 1H), 7.28 (s, 1H), 7.14-7.06 (m, 3H), 3.55-3.42 (m, 2H), 3.24 (s, 3H), 3.16 (s, 2H), 2.51 (s, 3H). |
| 1A-96 | CDCl₃: δ 7.56 (d, J = 7.2 Hz, 2H), 7.46 (d, J = 8.0 Hz, 2H), 7.42 (t, J = 7.2 Hz, 2H), 7.33 (d, J = 7.6 Hz, 1H), 7.20 (d, J = 7.6 Hz, 1H), 7.09 (d, J = 8.4 Hz, 3H), 3.80-3.65 (m, 2H), 3.51-3.37 (m, 2H), 3.22-3.14 (m, 2H), 2.51 (s, 3H). 1.10 (t, J = 7.6 Hz, 3H). |

TABLE 2-continued

| S. No. | ¹H NMR |
| --- | --- |
| 1A-97 | CDCl₃: δ 7.45-7.53 (m, 2H), 7.29 (s, 1H), 7.18-7.06 (m, 3H), 6.90-6.72 (m, 1H), 5.06-4.84 (m, 1H), 3.59-3.37 (m, 1H), 3.01-2.87 (m, 2H), 2.49 (s, 3H), 2.18-1.90 (m, 2H). |
| 1A-98 | CDCl₃: δ 7.50 (d, J = 8.0 Hz, 2H), 7.15-7.10 (m, 4H), 4.97 (m, 1H), 3.93-3.44 (m, 2H), 3.21-3.14 (m, 2H), 2.53 (s, 3H), 1.10 (d, J = 6.8 Hz, 3H), 0.98 (d, J = 6.8 Hz, 3H). |
| 1A-99 | CDCl₃: δ 7.99 (d, J = 7.2 Hz, 1H), 7.62 (t, J = 7.2 Hz, 4H), 7.45 (d, J = 8.0 Hz, 2H), 7.31 (d, J = 8.0 Hz, 2H), 6.89 (d, J = 9.2 Hz, 1H), 6.84 (s, 1H), 3.83 (s, 2H), 3.43-3.36 (m, 2H), 1.98 (s, 3H). |
| 1A-100 | CDCl₃: δ 7.99 (d, J = 7.2 Hz, 1H), 7.73 (s, 4H), 7.67 (d, J = 7.6 Hz, 2H), 7.48 (d, J = 8.0 Hz, 2H), 6.90 (d, J = 9.2 Hz, 1H), 6.84 (bs, 1H), 3.84 (s, 2H), 3.43-3.36 (m, 2H), 1.99 (s, 3H). |
| 1A-101 | CDCl₃: δ 8.51 (d, J = 9.2 Hz, 1H), 7.73 (d, J = 8.0 Hz, 1H), 7.53 (d, J = 7.6 Hz, 1H), 7.32 (s, 1H), 6.98 (d, J = 8.8 Hz, 1H), 6.86 (d, J = 12.0 Hz, 1H), 3.64 (s, 2H), 3.36-3.25 (m, 2H), 2.37 (s, 3H). |
| 1A-102 | CDCl₃: δ 8.50 (d, J = 7.6 Hz, 1H), 7.59-7.54 (m, 4H), 7.41 (d, J = 8.0 Hz, 2H), 7.31 (bs, 1H), 7.14 (t, J = 8.8 Hz, 2H), 6.92 (d, J = 11.6 Hz, 1H), 3.80 (s, 2H), 3.42-3.34 (m, 2H), 2.40 (s, 3H). |
| 1A-103 | CDCl₃: δ 8.50 (d, J = 8.0 Hz, 1H), 7.59 (d, J = 8.0 Hz, 2H), 7.54 (d, J = 8.8 Hz, 2H), 7.38 (d, J = 8.0 Hz, 2H), 7.32 (bs, 1H), 7.14 (t, J = 8.8 Hz, 2H), 6.92 (d, J = 11.6 Hz, 1H), 3.86 (s, 3H), 3.79 (s, 2H), 3.15-3.34 (m, 2H) 2.40 (s, 3H). |
| 1A-104 | CDCl₃: δ 7.61 (d, J = 8.0 Hz, 2H), 7.53 (d, J = 8.4 Hz, 1H), 7.48 (d, J = 8.0 Hz, 1H), 7.44 (d, J = 7.6, 4H), 7.31 (bs, 1H), 7.22 (d, J = 8.0 Hz, 1H), 6.92 (d, J = 11.6 Hz, 1H), 3.82 (s, 2H), 3.34-3.34 (m, 2H), 2.40 (s, 3H). |
| 1A-105 | CDCl3: δ 8.50 (d, J = 7.6 Hz, 1H), 7.73 (d, J = 14.4 Hz, 2H), 7.61 (d, J = 8.0 Hz, 3H), 7.46 (d, J = 8.0 Hz, 2H), 7.30 (bs, 1H), 6.93 (d, J = 11.6 Hz, 1H), 3.82 (s, 2H), 3.34-3.41 (m, 2H) 2.41 (s, 3H). |
| 1A-106 | CDCl₃: δ 8.53 (d, J = 8.0 Hz, 1H), 7.51 (d, J = 8.0 Hz, 2H), 7.45-7.36 (m, 6H), 7.19-7.12 (m, 1H), 6.92 (d, J = 11.2 Hz, 1H), 3.82 (s, 2H), 3.38 (q, J = 9.6 Hz, 2H), 2.40 (s, 3H). |
| 1A-107 | CDCl₃: δ 8.50 (d, J = 7.6 Hz, 1H), 7.84 (s, 1H), 7.77 (d, J = 7.6 Hz, 1H), 7.63 (t, J = 7.6 Hz, 3H), 7.57 (t, J = 7.6 Hz, 1H), 7.45 (d, J = 8.4 Hz, 2H), 7.33 (s, 1H), 6.92 (d, J = 12.8 Hz, 1H), 3.82 (s, 2H), 3.38 (q, J = 9.6 Hz, 2H), 2.41 (s, 3H). |
| 1A-108 | CDCl₃: δ 8.51 (d, J = 7.6 Hz, 1H), 7.62 (d, J = 8.0 Hz, 2H), 7.44-7.36 (m, 4H), 7.31-7.26 (m, 2H), 7.07-7.04 (m, 1H), 6.92 (d, J = 11.6 Hz, 1H), 3.81 (s, 2H), 3.38 (q, J = 8.8 Hz, 2H), 2.40 (s, 3H). |
| 1A-109 | CDCl₃: δ 8.50 (d, J = 8.0 Hz, 1H), 7.60 (d, J = 6.8 Hz, 2H), 7.47-7.41 (m, 3H), 7.34-7.31 (m, 2H), 7.26-7.14 (m, 2H), 6.92 (d, J = 11.2 Hz, 1H), 3.81 (s, 2H), 3.38 (q, J = 9.6 Hz, 2H), 2.40 (s, 3H). |
| 1A-110 | CDCl₃: δ 7.85 (s, 1H), 7.64 (d, J = 6.4 Hz, 1H), 7.55 (d, J = 8.4 Hz, 1H), 7.44 (d, J = 8.0 Hz, 2H), 7.31 (d, J = 8.0 Hz, 1H), 7.15 (d, J = 8.0 Hz, 2H), 7.10 (d, J = 10.4 Hz, 1H), 3.54-3.43 (m, 2H), 3.28-3.24 (m, 5H), 2.52 (s, 3H). |
| 1A-111 | CDCl₃: δ 7.69-7.65 (m, 2H), 7.57-7.53 (m, 1H), 7.49-7.44 (m, 1H), 7.32 (s, 1H), 7.29 (s, 2H), 7.09 (d, J = 6.8 Hz, 2H), 3.57-3.48 (m, 2H), 3.29-3.22 (m, 5H), 2.51 (s, 3H). |
| 1A-112 | CDCl₃: δ 7.58 (d, J = 8.0 Hz, 2H), 7.19-7.11 (m, 4H), 3.75-3.83 (m, 1H), 3.70-3.66 (m, 1H), 3.52-3.40 (m, 2H), 3.27-3.20 (m, 2H), 2.53 (s, 3H), 2.15-2.09 (m, 2H), 1.79-1.71 (m, 2H). |
| 1A-113 | CDCl₃: δ 8.52 (d, J = 8.0 Hz, 1H), 7.46-7.40 (m, 4H), 7.34-7.30 (m, 2H), 7.25-7.22 (m, 1H), 7.08-7.03 (m, 1H), 6.93 (d, J = 11.6 Hz, 1H), 3.82 (s, 2H), 3.38 (q, J = 9.6 Hz, 2H), 2.41 (s, 3H). |
| 1A-114 | CDCl₃: δ 8.50 (d, J = 8.0 Hz, 1H), 7.89 (d, J = 1.6 Hz, 1H), 7.79 (d, J = 8.0 Hz, 1H), 7.57-7.61 (m, 3H), 7.45 (d, J = 8.0 Hz, 2H), 7.31 (bs, 1H), 6.93 (d, J = 11.6 Hz, 1H), 3.82 (s, 2H), 3.38 (q, J = 9.6 Hz, 2H), 2.40 (s, 3H). |
| 1A-115 | CDCl₃: δ 9.22 (s, 1H), 8.97 (s, 2H), 8.50 (d, J = 8.0 Hz, 1H), 7.63 (d, J = 8.0 Hz, 2H), 7.51 (d, J = 8.0 Hz, 2H), 7.33 (bs, 1H), 6.94 (d, J = 11.6 Hz, 1H), 3.84 (s, 2H), 3.37 (q, J = 9.6 Hz, 2H), 2.41 (s, 3H). |
| 1A-116 | CDCl₃: δ 8.69 (d, J = 7.6 Hz, 1H), 8.42 (bs, 1H), 7.68 (d, J = 8.0 Hz, 2H), 7.51 (d, J = 8.0 Hz, 2H), 6.98 (d, J = 11.2 Hz, 1H), 4.31 (s, 2H), 3.39 (q, J = 9.6 Hz, 2H), 2.44 (s, 3H). |
| 1A-117 | CDCl₃: δ 7.54 (d, J = 8.4 Hz, 2H), 7.13-7.10 (m, 3H), 7.03 (d, J = 10.0 Hz, 1H), 4.14-3.95 (m, 2H), 3.66 (s, 3H), 3.19-3.05 (m, 2H), 2.49 (s, 3H). |
| 1A-118 | CDCl₃: δ 7.45 (d, J = 8.0 Hz, 2H), 7.41-7.30 (m, 3H), 7.28 (s, 1H), 7.23 (s, 1H), 7.11 (d, J = 8.0 Hz, 2H), 7.04-7.00 (m, 1H), 3.54-3.42 (m, 2H), 3.29-3.18 (m, 5H), 2.49 (s, 3H). |
| 1A-119 | CDCl₃: δ 7.37-7.32 (m, 5H), 7.19-7.12 (m, 2H), 7.09-7.06 (m, 2H), 7.04 (s, 1H), 3.55-3.44 (m, 2H), 3.30-3.19 (m, 5H), 2.51 (s, 3H). |
| 1A-120 | CDCl₃: δ 7.68 (d, J = 14.0 Hz, 2H), 7.57 (s, 1H), 7.45 (d, J = 8.4 Hz, 2H), 7.32 (d, J = 7.6 Hz, 1H), 7.15 (d, J = 8.4 Hz, 2H), 7.10 (d, J = 10.0 Hz, 1H), 3.49 (m, 2H), 3.33-3.19 (m, 5H), 2.52 (s, 3H). |
| 1A-121 | CDCl₃: δ 7.79 (s, 1H), 7.73 (d, J = 7.6 Hz, 1H), 7.60-7.52 (m, 2H), 7.48 (d, J = 8.0 Hz, 2H), 7.31-7.27 (m, 1H), 7.19-7.10 (m, 3H), 3.55-3.43 (m, 2H), 3.27-3.19 (m, 5H), 2.50 (s, 3H). |
| 1A-122 | CDCl₃: δ 7.48 (d, J = 8.8 Hz, 2H), 7.42 (d, J = 8.4 Hz, 2H), 7.29-7.24 (m, 1H), 7.19-7.14 (m, 1H), 7.09-7.06 (m, 2H), 6.96 (d, J = 8.4 Hz, 2H), 3.86 (s, 3H), 3.53-3.40 (m, 2H), 3.23-3.16 (m, 5H), 2.48 (s, 3H). |
| 1A-123 | CDCl₃: δ 7.52-7.48 (m, 2H), 7.42 (d, J = 8.0 Hz, 2H), 7.29-7.27 (m, 1H), 7.14-7.07 (m, 5H), 3.53-3.41 (m, 2H), 3.23-3.20 (m, 5H), 2.51 (s, 3H). |
| 1A-124 | CDCl₃: δ 7.43-7.38 (m, 3H), 7.33-7.27 (m, 2H), 7.14-7.06 (m, 5H), 3.52-3.44 (m, 2H), 3.24-3.17 (m, 5H), 2.48 (s, 3H). |
| 1A-125 | CDCl₃: δ 7.40-7.32 (m, 5H), 7.19-7.12 (m, 2H), 7.09-7.04 (m, 3H), 3.55-3.44 (m, 2H), 3.28-3.21 (m, 5H), 2.51 (s, 3H). |
| 1A-126 | CDCl₃: δ 8.46 (d, J = 8.0 Hz, 1H), 8.26 (bs, 1H), 7.62 (d, J = 8.8 Hz, 2H), 7.47 (d, J = 8.8 Hz, 2H), 7.03 (d, J = 11.2 Hz, 1H), 3.40-3.33 (m, 2H), 2.44 (s, 3H). |
| 1A-127 | CDCl₃: δ 7.49-7.35 (m, 4H), 7.29-7.28 (m, 2H), 7.11-7.06 (m, 2H), 6.91 (d, J = 8.8 Hz, 2H), 3.50-3.33 (m, 2H), 3.28-3.21 (m, 5H), 2.51 (s, 3H). |
| 1A-128 | CDCl₃: δ 7.45 (d, J = 6.8 Hz, 1H), 7.33-7.27 (m, 6H), 7.10-7.06 (m, 3H), 3.56-3.44 (m, 2H), 3.24-3.20 (m, 5H), 2.51 (s, 3H). |
| 1A-129 | CDCl₃: δ 7.30 (d, J = 8.4 Hz, 2H), 7.18-7.14 (m, 3H), 6.89 (d, J = 10.4 Hz, 1H), 3.28-3.21 (m, 5H), 2.47 (s, 3H). |
| 1A-130 | CDCl₃: δ 7.21 (d, J = 7.6 Hz, 1H), 7.06-7.03 (m, 3H), 6.91 (d, J = 8.0 Hz, 2H), 3.48-3.34 (m, 2H), 3.25-3.14 (m, 5H), 3.54-2.49 (m, 5H), 1.62-1.50 (m, 2H), 0.84 (t, J = 7.2 Hz, 3H). |
| 1A-131 | CDCl₃: δ 7.69-7.67 (m, 1H), 7.35 (d, J = 7.6 Hz, 1H), 7.12 (d, J = 11.2 Hz, 1H), 6.94-6.83 (m, 2H), 3.56-3.30 (m, 2H), 3.35-3.12 (m, 5H), 2.54 (s, 3H). |
| 1A-132 | CDCl₃: δ 7.50 (d, J = 7.6 Hz, 1H), 7.22-7.14 (m, 1H), 7.11 (d, J = 10.0 Hz, 1H), 6.83 (t, J = 9.4 Hz, 2H), 3.45 (s, 2H), 3.35 (q, J = 9.4 Hz, 2H), 3.25 (s, 3H), 2.51 (s, 3H). |
| 1A-133 | CDCl₃: δ 7.19 (d, J = 7.6 Hz, 1H), 7.06 (d, J = 7.6 Hz, 3H), 6.92 (d, J = 8.0 Hz, 2H), 3.48-3.34 (m, 2H), 3.21-3.13 (m, 5H), 2.59 (q, J = 7.6 Hz, 2H), 2.50 (s, 3H), 1.24-1.14 (m, 3H). |

TABLE 2-continued

| S. No. | $^1$H NMR |
|---|---|
| 1A-134 | CDCl$_3$: δ 7.86-7.75 (m, 2H), 7.50-7.37 (m, 1H), 7.22 (d, J = 8.0 Hz, 2H), 6.98-6.08 (m, 1H), 3.37-3.25 (m, 2H), 3.21-3.17 (m, 5H), 2.55-2.41 (m, 5H), 1.17-1.13 (m, 3H). |
| 1A-135 | CDCl$_3$: δ 8.05 (s, 1H), 7.82-7.76 (m, 2H), 7.18-7.16 (m, 1H), 7.16-7.12 (m, 1H), 6.94-6.89 (m, 1H), 3.73-3.58 (m, 2H), 3.40-3.36 (m, 2H), 3.22 (s, 3H), 3.10-2.98 (m, 3H), 2.47 (s, 3H). |
| 1A-136 | CDCl$_3$: δ 8.46 (d, J = 8.0 Hz, 1H), 7.96 (d, J = 8.4 Hz, 2H), 7.56 (d, J = 8.0 Hz, 2H), 7.32 (s, 1H), 6.95 (d, J = 11.6 Hz, 1H), 3.85 (s, 2H), 3.40-3.32 (m, 2H), 3.06 (s, 3H), 2.42 (s, 3H). |
| 1A-137 | CDCl$_3$: δ 8.44 (d, J = 7.6 Hz, 1H), 8.31 (s, 1H), 7.82 (d, J = 8.4 Hz, 2H), 7.78 (s, 1H), 7.76 (s, 1H), 7.03 (d, J = 11.2 Hz, 1H), 3.40-3.33 (m, 2H), 2.45 (s, 3H). |
| 1A-138 | CDCl$_3$: δ 7.58 (d, J = 8.0 Hz, 2H), 7.35 (d, J = 8.0 Hz, 2H), 7.20 (d, J = 7.6 Hz, 1H), 6.84 (d, J = 10.0 Hz, 1H), 3.32-3.20 (m, 5H), 2.47 (s, 3H). |
| 1A-139 | CDCl$_3$: δ 7.53 (d, J = 12.4 Hz, 1H), 7.49 (d, J = 6.4 Hz, 1H), 7.16-7.12 (m, 2H), 7.07 (d, J = 8.4 Hz, 1H), 6.91 (d, J = 8.4 Hz, 1H), 3.43-3.35 (m, 2H), 3.18 (d, J = 9.6 Hz, 2H), 2.40 (s, 3H), 1.41 (d, J = 6.4 Hz, 3H). |
| 1A-140 | CDCl$_3$: δ 8.52 (d, J = 8.0 Hz, 1H), 7.50 (d, J = 1.6 Hz, 1H), 7.46-7.40 (m, 4H), 7.30 (d, J = 2.0 Hz, 1H), 7.31-7.26 (m, 2H), 6.93 (d, J = 11.6 Hz, 1H), 3.82 (s, 2H), 3.38 (q, J = 10.0 Hz, 2H), 2.41 (s, 3H). |
| 1A-141 | CDCl$_3$: δ 8.50 (d, J = 8.0 Hz, 1H), 7.54 (d, J = 8.0 Hz, 2H), 7.43 (d, J = 7.6 Hz, 2H), 7.29 (bs, 1H), 7.21-7.16 (m, 2H), 6.93 (d, J = 11.6 Hz, 1H), 3.81 (d, J = 4.8 Hz, 2H), 3.37 (q, J = 9.6 Hz, 2H), 2.41 (s, 3H). |
| 1A-142 | CDCl$_3$: δ 8.49 (q, J = 4.8 Hz, 1H), 7.69-7.40 (m, 5H), 7.30 (bs, 1H), 7.26-7.21 (m, 3H), 6.99-6.90 (m, 1H), 3.81 (d, J = 6.8 Hz, 2H), 3.41-3.27 (m, 2H), 2.40 (s, 3H). |
| 1A-143 | CDCl$_3$: δ 8.50 (d, J = 7.6 Hz, 1H), 7.58 (d, J = 8.4 Hz, 2H), 7.46 (d, J = 1.6 Hz, 2H), 7.43 (d, J = 8.0 Hz, 2H), 7.35 (t, J = 1.6 Hz, 1H), 7.29 (bs, 1H), 6.92 (d, J = 11.6 Hz, 1H), 3.81 (s, 2H), 3.38 (q, J = 9.6 Hz, 2H), 2.40 (s, 3H). |
| 1A-144 | CDCl$_3$: δ 8.50 (d, J = 7.6 Hz, 1H), 7.61 (d, J = 8.4 Hz, 2H), 7.53 (d, J = 8.4 Hz, 2H), 7.40 (d, J = 7.6 Hz, 2H), 7.34 (d, J = 8.4 Hz, 3H), 6.91 (d, J = 11.6 1H), 3.80 (s, 2H), 3.38 (q, J = 9.6 Hz, 2H), 2.53 (s, 3H), 2.40 (s, 3H). |
| 1A-145 | CDCl$_3$: δ 8.50 (d, J = 7.6 Hz, 1H), 7.62 (d, J = 8.0 Hz, 2H), 7.50 (d, J = 8.0 Hz, 2H), 7.39 (d, J = 8.0 Hz, 2H), 7.32 (bs, 1H), 7.27-7.26 (m, 2H), 6.91 (d, J = 11.6 1H), 3.80 (s, 2H), 3.38 (q, J = 9.6 Hz, 2H), 2.40 (s, 6H). |
| 1A-146 | CDCl$_3$: δ 7.48 (d, J = 8.4 Hz, 2H), 7.44 (d, J = 8.4 Hz, 2H), 7.31 (d, J = 8.4 Hz, 2H), 7.27 (s, 1H), 7.08 (t, J = 5.6 Hz, 3H), 3.50 (s, 1H), 3.45 (s, 1H), 3.23 (s, 3H), 3.20 (d, J = 10.0 Hz, 2H), 2.52 (s, 6H). |
| 1A-147 | CDCl$_3$: δ 7.42 (q, J = 6.5 Hz, 4H), 7.32 (s, 2H), 7.14 (s, 3H), 3.23 (m, 7H), 2.52 (s, 3H). |
| 1A-148 | CDCl$_3$: δ 7.56 (d, J = 6.0 Hz, 1H), 7.44-7.40 (m, 2H), 7.37-7.32 (m, 2H), 7.29-7.26 (m, 2H), 7.12-7.06 (m, 2H), 6.91 (d, J = 8.4 Hz, 2H), 3.49-3.28 (m, 2H), 3.28-3.18 (m, 5H), 2.51 (s, 3H). |
| 1A-149 | CDCl$_3$: δ 7.45 (d, J = 8.0 Hz, 4H), 7.23 (d, J = 8.4 Hz, 3H), 7.09-7.06 (m, 3H), 3.47 (m, 2H), 3.23 (s, 3H), 3.20-3.16 (m, 2H), 2.50 (s, 3H), 2.39 (s, 3H). |

TABLE 3

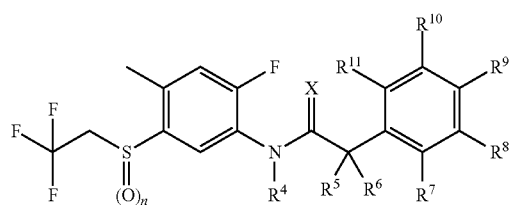

| S. No. | R$^4$ | R$^5$ | R$^6$ | R$^7$ | R$^8$ | R$^9$ | R$^{10}$ | R$^{11}$ | X | n |
|---|---|---|---|---|---|---|---|---|---|---|
| 1B-1 | H | H | H | H | H | S—Et | H | H | O | 0 |
| 1B-2 | H | H | H | H | H | S—n-Pr | H | H | O | 0 |
| 1B-3 | H | H | H | H | H | S—i-Pr | H | H | O | 0 |
| 1B-4 | H | H | H | H | H | (4-phenyl)-phenyl | H | H | O | 0 |
| 1B-5 | H | H | H | H | H | 4-cyano-phenyl | H | H | O | 0 |
| 1B-6 | H | H | H | H | H | 4-dimethylamino-phenyl | H | H | O | 0 |
| 1B-7 | Me | H | H | H | H | S—Et | H | H | O | 0 |
| 1B-8 | Me | H | H | H | H | S—i-Pr | H | H | O | 0 |
| 1B-9 | Me | H | H | H | H | i-Pr | H | H | O | 0 |
| 1B-10 | Me | H | H | H | H | S—n-Pr | H | H | O | 0 |
| 1B-11 | H | H | H | H | H | 2,3,4-Cl$_3$-phenyl | H | H | O | 0 |
| 1B-12 | H | H | H | H | H | 3-Cl-phenyl | H | H | O | 0 |
| 1B-13 | H | H | H | H | H | 4-Ac-phenyl | H | H | O | 0 |
| 1B-14 | Me | H | H | H | H | 4-phenyl-phenyl | H | H | O | 0 |
| 1B-15 | Me | H | H | H | H | 4-cyano-phenyl | H | H | O | 0 |
| 1B-16 | Me | H | H | H | H | 2,3-Cl$_2$-phenyl | H | H | O | 0 |
| 1B-17 | Me | H | H | H | H | 4-S—Et-phenyl | H | H | O | 0 |
| 1B-18 | H | H | H | H | H | 2,3-Cl$_2$-phenyl | H | H | O | 0 |
| 1B-19 | H | H | H | H | H | 3,4-F$_2$-phenyl | H | H | O | 0 |
| 1B-20 | H | H | H | H | H | 2,3,4-F$_3$-phenyl | H | H | O | 0 |
| 1B-21 | H | H | H | H | H | 4-S—Et-phenyl | H | H | O | 0 |
| 1B-22 | H | H | H | H | H | 2,2,2-trifluoroethylthio | H | H | O | 0 |
| 1B-23 | Me | H | H | H | H | 2,2,2-trifluoroethylthio | H | H | O | 0 |

TABLE 3-continued

| S. No. | R⁴ | R⁵ | R⁶ | R⁷ | R⁸ | R⁹ | R¹⁰ | R¹¹ | X | n |
|---|---|---|---|---|---|---|---|---|---|---|
| 1B-24 | H | H | H | H | H | 2,2,2-trifluoroethylthio | H | H | S | 0 |
| 1B-25 | H | H | H | H | H | Cl | H | H | S | 0 |
| 1B-26 | H | H | H | H | H | (3,4-Cl₂)-phenyl | H | H | S | 0 |
| 1B-27 | H | H | H | H | H | phenyl | H | H | S | 0 |
| 1B-28 | H | H | H | H | H | OCF₃ | H | H | S | 0 |
| 1B-29 | Me | H | H | H | H | (3,4-F₂)-phenyl | H | H | O | 0 |
| 1B-30 | Me | H | H | H | H | (2,3,4-F₃)-phenyl | H | H | O | 0 |
| 1B-31 | Me | H | H | H | H | 4-Ac-phenyl | H | H | O | 0 |
| 1B-32 | Me | H | H | H | H | (2,3,4-Cl₃)-phenyl | H | H | O | 0 |
| 1B-33 | Me | H | H | H | H | 3-Cl-phenyl | H | H | O | 0 |
| 1B-34 | Me | H | H | H | H | 3-CF₃-phenyl | H | H | O | 0 |
| 1B-35 | Me | H | H | H | H | 3-OCF₃-phenyl | H | H | O | 0 |
| 1B-36 | Me | H | H | H | H | 2,2,2-trifluoroethylthio | H | H | S | 0 |
| 1B-37 | Me | H | H | H | H | phenyl | H | H | S | 0 |
| 1B-38 | H | H | H | H | H | 3-OCF₃-phenyl | H | H | S | 0 |
| 1B-39 | Me | H | H | H | H | OCF₃ | H | H | S | 0 |
| 1B-40 | H | F | F | H | H | phenyl | H | H | O | 0 |
| 1B-41 | Me | F | F | H | H | phenyl | H | H | O | 0 |
| 1B-42 | H | H | H | 3-CF₃-phenyl | H | H | H | H | O | 0 |
| 1B-43 | H | H | H | H | H | 3-CF₃-phenyl | H | H | S | 0 |
| 1B-44 | H | H | H | 3-OCF₃-phenyl | H | H | H | H | O | 0 |
| 1B-45 | H | H | H | phenyl | H | H | H | H | O | 0 |
| 1B-46 | H | H | H | phenyl | H | H | H | H | S | 0 |
| 1B-47 | H | H | H | 3-OCF₃-phenyl | H | H | H | H | S | 0 |
| 1B-48 | Me | H | H | phenyl | H | H | H | H | O | 0 |
| 1B-49 | Me | H | H | 3-CF₃-phenyl | H | H | H | H | O | 0 |
| 1B-50 | Me | H | H | 3-OCF₃-phenyl | H | H | H | H | O | 0 |
| 1B-51 | Me | H | H | phenyl | H | H | H | H | S | 0 |
| 1B-52 | Me | H | H | 3-CF₃-phenyl | H | H | H | H | S | 0 |
| 1B-53 | H | F | F | H | H | SCF₃ | H | H | O | 0 |
| 1B-54 | Me | F | F | H | H | SCF₃ | H | H | O | 0 |
| 1B-55 | Me | H | H | 3-OCF₃-phenyl | H | H | H | H | S | 0 |
| 1B-56 | H | F | H | H | H | CF₃ | H | H | O | 0 |
| 1B-57 | H | H | H | H | 3-OCF₃-phenyl | H | H | H | O | 0 |
| 1B-58 | H | H | H | H | phenyl | H | H | H | O | 0 |
| 1B-59 | H | H | H | H | 3-CF₃-phenyl | H | H | H | O | 0 |
| 1B-60 | H | H | H | H | 4-CF₃-phenyl | H | H | H | O | 0 |
| 1B-61 | Me | H | H | H | 3-OCF₃-phenyl | H | H | H | O | 0 |
| 1B-62 | Me | H | H | H | phenyl | H | H | H | O | 0 |
| 1B-63 | Me | H | H | H | 3-CF₃-phenyl | H | H | H | O | 0 |
| 1B-64 | Me | H | H | H | 4-CF₃-phenyl | H | H | H | O | 0 |
| 1B-65 | Me | H | H | H | 4-OCF₃-phenyl | H | H | H | O | 0 |
| 1B-66 | H | H | H | H | 2,3-Cl₂-phenyl | H | H | H | O | 0 |
| 1B-67 | H | H | H | H | 2,4-Cl₂-phenyl | H | H | H | O | 0 |
| 1B-68 | H | H | H | H | 2,5-Cl₂-phenyl | H | H | H | O | 0 |
| 1B-69 | H | H | H | H | 3,4-Cl₂-phenyl | H | H | H | O | 0 |
| 1B-70 | H | H | H | H | 3,5-Cl₂-phenyl | H | H | H | O | 0 |
| 1B-71 | H | H | H | H | 3-Cl-phenyl | H | H | H | O | 0 |
| 1B-72 | Me | H | H | H | 3-Cl-phenyl | H | H | H | O | 0 |
| 1B-73 | Me | H | H | H | 2,5-Cl₂-phenyl | H | H | H | O | 0 |
| 1B-74 | Me | H | H | H | 3,4-Cl₂-phenyl | H | H | H | O | 0 |
| 1B-75 | H | F | F | H | H | SCF₃ | H | H | O | 2 |
| 1B-76 | Me | H | H | H | 2,3-Cl₂-phenyl | H | H | H | O | 0 |
| 1B-77 | Me | H | H | H | 2,4-Cl₂-phenyl | H | H | H | O | 0 |
| 1B-78 | Me | H | H | H | 3,5-Cl₂-phenyl | H | H | H | O | 0 |
| 1B-79 | H | H | H | H | H | OCHF₂ | H | H | O | 0 |
| 1B-80 | Me | H | H | H | H | OCHF₂ | H | H | O | 0 |
| 1B-81 | H | H | H | H | H | OCHF₂ | H | H | O | 2 |
| 1B-82 | Me | H | H | H | H | OCHF₂ | H | H | O | 2 |
| 1B-83 | Me | H | H | H | H | OCHF₂ | H | H | O | 1 |
| 1B-84 | H | H | H | H | H | SCF₃ | H | H | O | 2 |
| 1B-85 | H | H | H | H | 3-CF₃-Phenyl | H | H | H | O | 2 |
| 1B-86 | H | F | F | H | H | OCF₃ | H | H | O | 0 |
| 1B-87 | Me | F | F | H | H | OCF₃ | H | H | O | 0 |
| 1B-88 | H | F | F | H | H | OCF₃ | H | H | O | 2 |

TABLE 3-continued

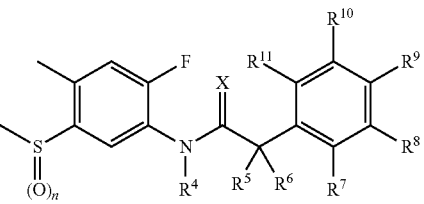

| S. No. | R⁴ | R⁵ | R⁶ | R⁷ | R⁸ | R⁹ | R¹⁰ | R¹¹ | X | n |
|---|---|---|---|---|---|---|---|---|---|---|
| 1B-89 | Me | F | F | H | H | OCF₃ | H | H | O | 2 |
| 1B-90 | H | H | H | H | 3-(benzo[d][1,3]dioxol-5-yl)phenyl | H | H | H | O | 0 |
| 1B-91 | H | H | H | H | 3-F-Phenyl | H | H | H | O | 0 |
| 1B-92 | H | H | H | H | 4-S—Et-Phenyl | H | H | H | O | 0 |
| 1B-93 | H | H | H | H | 2-S—Me-Phenyl | H | H | H | O | 0 |
| 1B-94 | H | H | H | H | (4-Phenyl)Phenyl | H | H | H | O | 0 |
| 1B-95 | H | H | H | H | 4-Cyano-Phenyl | H | H | H | O | 0 |
| 1B-96 | Me | H | H | H | 4-Cyano-Phenyl | H | H | H | O | 0 |
| 1B-97 | Me | H | H | H | (4-Phenyl)Phenyl | H | H | H | O | 0 |
| 1B-98 | Me | H | H | H | 2-S—Me-Phenyl | H | H | H | O | 0 |
| 1B-99 | Me | H | H | H | 4-S—Et-Phenyl | H | H | H | O | 0 |
| 1B-100 | Me | H | H | H | 3-F-Phenyl | H | H | H | O | 0 |
| 1B-101 | Me | H | H | H | 3-(benzo[d][1,3]dioxol-5-yl)phenyl | H | H | H | O | 0 |
| 1B-102 | H | H | H | H | H | cyano | H | H | O | 0 |

TABLE 4

| S. No. | ¹H NMR |
|---|---|
| 1B-1 | CDCl3: δ 8.48 (d, J = 8.0 Hz, 1H), 7.35 (d, J = 8.4 Hz, 2H), 7.26-7.24 (m, 3H), 6.90 (d, J = 11.6 Hz, 1H), 3.72 (s, 2H), 3.37 (q, J = 9.6 Hz, 2H), 2.99-2.93 (m, 2H), 2.39 (s, 3H), 1.30 (t, J = 7.2 Hz, 3H). |
| 1B-2 | CDCl3: δ 8.48 (d, J = 8.0 Hz, 1H), 7.52 (d, J = 8.4 Hz, 1H), 7.47 (d, J = 8.4 Hz, 2H), 7.32-7.23 (m, 3H), 6.93 (d, J = 11.6 Hz, 1H), 3.73 (s, 2H), 3.36 (q, J = 7.2 Hz, 2H), 3.44 (q, J = 9.6 Hz, 2H), 3.39 (q, J = 9.6 Hz, 2H), 2.40 (s, 3H), 0.88 (t, J = 7.2 Hz, 3H). |
| 1B-3 | CDCl3: δ 8.49 (d, J = 7.6 Hz, 1H), 7.52 (d, J = 8.4 Hz, 1H), 7.45 (d, J = 8.4 Hz, 2H), 7.27 (d, J = 8.0 Hz, 2H), 6.91 (d, J = 11.6 Hz, 1H), 3.73 (s, 2H), 3.38 (q, J = 9.6 Hz, 2H), 2.39 (s, 3H), 1.42-141 (m, 1H), 1.31 (d, J = 7.6 Hz, 6H). |
| 1B-4 | CDCl3: δ 8.51 (d, J = 8.0 Hz, 1H), 7.69-7.64 (m, 8H), 7.48-7.42 (m, 4H), 7.38-7.35 (m, 2H), 6.91 (d, J = 11.6 Hz, 1H), 3.82 (s, 2H), 3.38 (q, J = 9.6 Hz, 2H), 2.40 (s, 3H). |
| 1B-5 | CDCl3: δ 8.50 (d, J = 8.0 Hz, 1H), 7.75-7.68 (m, 4H), 7.62 (d, J = 8.0 Hz, 2H), 7.46 (d, J = 8.0 Hz, 2H), 7.31 (bs, 1H), 6.92 (d, J = 12.0 Hz, 1H), 3.82 (s, 2H), 3.38 (q, J = 9.6 Hz, 2H), 2.40 (s, 3H). |
| 1B-6 | CDCl3: δ 8.50 (d, J = 7.6 Hz, 1H), 7.59 (d, J = 8.0 Hz, 2H), 7.51 (d, J = 8.8 Hz, 2H), 7.36-7.32 (m, 3H), 6.90 (d, J = 7.6 Hz, 1H), 6.81 (d, J = 8.0 Hz, 2H), 3.78 (s, 2H), 3.38 (q, J = 9.6 Hz, 2H), 3.00 (s, 6H), 2.39 (s, 3H). |
| 1B-7 | CDCl3: δ 7.25 (m, J = 8.0 Hz, 2H), 7.29 (d, J = 8.0 Hz, 1H), 7.14-7.12 (m, 3H), 7.04 (t, J = 7.6 Hz, 1H), 6.93 (d, J = 8.0 Hz, 1H), 3.41 (q, J = 9.6 Hz, 2H), 3.25 (q, J = 9.6 Hz, 2H), 3.20 (s, 3H), 2.93-2.86 (m, 2H), 2.50 (s, 3H), 1.30 (t, J = 7.2 Hz, 3H). |
| 1B-8 | CDCl3: δ 7.31 (s, 1H), 7.27 (s, 2H), 7.04 (d, J = 10.0 Hz, 1H), 6.94 (d, J = 8.4 Hz, 2H), 3.43-3.25 (m, 5H), 3.21 (s, 3H), 2.50 (s, 3H), 1.33-1.21 (m, 6H). |
| 1B-9 | CDCl3: δ 7.22 (d, J = 8.0 Hz, 1H), 7.09 (d, J = 8.0 Hz, 2H), 7.05 (d, J = 10.0 Hz, 1H), 6.93 (d, J = 8.0 Hz, 2H), 3.47-3.33 (m, 2H), 3.21 (s, 3H), 3.17 (q, J = 9.4 Hz, 2H), 2.88-2.81 (m, 1H), 2.49 (s, 3H), 1.33-1.21 (m, 6H). |
| 1B-10 | CDCl3: δ 7.36 (d, J = 8.4 Hz, 1H), 7.33-7.25 (m, 2H), 7.05 (d, J = 10.4 Hz, 1H), 7.00 (d, J = 8.0 Hz, 1H), 6.96 (d, J = 8.0 Hz, 1H), 3.56-3.23 (m, 6H), 3.21 (s, 3H), 2.50 (s, 3H), 1.42-1.36 (m, 2H), 0.92 (t, J = 7.2 Hz, 3H). |
| 1B-11 | CDCl3: δ 8.49 (d, J = 7.6 Hz, 1H), 7.53 (d, J = 8.4 Hz, 1H), 7.45-7.42 (m, 3H), 7.35-7.30 (m, 1H), 7.23-7.18 (m, 2H), 6.93 (d, J = 12.0 Hz, 1H), 3.82-3.71 (m, 2H), 3.39 (q, J = 9.6 Hz, 2H), 2.40 (s, 3H). |
| 1B-12 | CDCl3: δ 8.50 (d, J = 7.6 Hz, 1H), 7.61-7.58 (m, 3H), 7.48-7.31 (m, 6H), 6.93 (d, J = 11.6 Hz, 1H), 3.81 (s, 2H), 3.36 (q, J = 9.6 Hz, 2H), 2.40 (s, 3H). |
| 1B-13 | CDCl3: δ 8.50 (d, J = 8.0 Hz, 1H), 8.04 (d, J = 8.8 Hz, 2H), 7.70-7.66 (m, 4H), 7.45 (d, J = 8.4 Hz, 2H), 7.31 (bs, 1H), 6.92 (d, J = 11.6 Hz, 1H), 3.82 (s, 2H), 3.38 (q, J = 9.6 Hz, 2H), 2.64 (s, 3H), 2.40 (s, 3H). |
| 1B-14 | CDCl3: δ 7.67-7.62 (m, 6H), 7.52 (d, J = 8.0 Hz, 2H), 7.45 (d, J = 7.6 Hz, 2H), 7.36 (d, J = 7.2 Hz, 1H), 7.28 (d, J = 7.6 Hz, 1H), 7.13-7.07 (m, 3H), 3.56-3.47 (m, 2H), 3.38 (q, J = 9.6 Hz, 2H), 3.24 (s, 3H), 2.51 (s, 3H). |

TABLE 4-continued

| S. No. | ¹H NMR |
|---|---|
| 1B-15 | CDCl3: δ 7.68 (d, J = 8.4 Hz, 2H), 7.64 (d, J = 8.4 Hz, 2H), 7.47 (d, J = 8.4 Hz, 2H), 7.31 (d, J = 7.6 Hz, 1H), 7.16 (d, J = 8.0 Hz, 2H), 7.09 (d, J = 10.0 Hz, 1H), 3.53-3.43 (m, 2H), 3.26 (s, 3H), 3.24 (q, J = 9.6 Hz, 2H), 2.51 (s, 3H). |
| 1B-16 | CDCl3: δ 7.45 (d, J = 7.6 Hz, 1H), 7.37-7.27 (m, 3H), 7.23-7.18 (m, 1H), 7.10-7.02 (m, 3H), 6.90 (d, J = 8.4 Hz, 1H), 3.64-3.51 (m, 2H), 3.36-3.20 (m, 5H), 2.51 (s, 3H). |
| 1B-17 | CDCl3: δ 7.48-7.43 (m, 4H), 7.38-7.35 (m, 2H), 7.27 (s, 1H), 7.10-7.06 (m, 3H), 3.53-3.41 (m, 2H), 3.23 (s, 3H), 3.20 (q, J = 9.6 Hz, 2H), 2.98 (q, J = 7.6 Hz, 2H), 3.50 (s, 3H), 1.29 (t, J = 7.2 Hz, 3H). |
| 1B-18 | CDCl3: δ 8.53-8.46 (m, 1H), 7.54-7.40 (m, 4H), 7.32 (s, 1H), 7.24-7.21 (m, 3H), 6.92 (d, J = 11.6 Hz, 1H), 3.82-3.71 (m, 2H), 3.38 (q, J = 9.6 Hz, 2H), 2.40 (s, 3H). |
| 1B-19 | CDCl3: δ 8.50 (d, J = 7.6 Hz, 1H), 7.55 (d, J = 8.4 Hz, 2H), 7.42-7.36 (m, 3H), 7.30 (bs, 1H), 7.28 (s, 1H), 7.23 (d, J = 10.0 Hz, 1H), 6.92 (d, J = 11.6 Hz, 1H), 3.80 (s, 2H), 3.38 (q, J = 9.6 Hz, 2H), 2.40 (s, 3H). |
| 1B-20 | CDCl3: δ 8.50 (d, J = 7.6 Hz, 1H), 7.53 (d, J = 7.2 Hz, 2H), 7.43 (d, J = 8.0 Hz, 2H), 7.30 (bs, 1H), 7.14 (s, 1H), 7.02 (d, J = 8.8 Hz, 1H), 6.92 (d, J = 12.0 Hz, 1H), 3.81 (s, 2H), 3.38 (q, J = 9.6 Hz, 2H), 2.40 (s, 3H). |
| 1B-21 | CDCl3: δ 8.50 (d, J = 8.0 Hz, 1H), 7.61 (d, J = 8.4 Hz, 2H), 7.52 (d, J = 8.4 Hz, 2H), 7.41-7.38 (m, 4H), 7.31 (bs, 1H), 6.92 (d, J = 11.6 Hz, 1H), 3.80 (s, 2H), 3.38 (q, J = 9.6 Hz, 2H), 2.99 (q, J = 7.2 Hz, 2H), 2.40 (s, 3H), 1.35 (t, J = 7.2 Hz, 3H). |
| 1B-22 | CDCl3: δ 8.48 (d, J = 8.0 Hz, 1H), 7.52 (d, J = 8.0 Hz, 1H), 7.46 (s, 1H), 7.31 (d, J = 8.0 Hz, 2H), 7.24 (s, 1H), 6.92 (d, J = 11.6 Hz, 1H), 3.74 (s, 2H), 3.47 (q, J = 9.6 Hz, 2H), 3.32 (q, J = 9.6 Hz, 2H), 2.40 (s, 3H). |
| 1B-23 | CDCl3: δ 8.48 (d, J = 8.0 Hz, 1H), 7.36 (d, J = 8.0 Hz, 1H), 7.30 (d, J = 9.2 Hz, 1H), 7.07-7.03 (m, 2H), 6.99 (d, J = 8.0 Hz, 2H), 3.44-3.36 (m, 4H), 3.25 (q, J = 9.6 Hz, 2H), 3.21 (s, 3H), 2.50 (s, 3H). |
| 1B-24 | CDCl3: δ 8.48 (d, J = 8.0 Hz, 1H), 7.52 (d, J = 8.0 Hz, 2H), 7.46 (s, 1H), 7.31 (d, J = 8.0 Hz, 2H), 6.92 (d, J = 12.4 Hz, 1H), 3.74 (s, 2H), 3.45-3.35 (m, 4H), 2.40 (s, 3H). |
| 1B-25 | CDCl3: δ 8.48 (d, J = 8.0 Hz, 1H), 7.37 (d, J = 8.4 Hz, 1H), 7.30 (d, J = 8.0 Hz, 1H), 7.17 (d, J = 8.0 Hz, 1H), 7.12 (d, J = 8.4 Hz, 1H), 7.02-6.94 (m, 1H), 6.90 (d, J = 8.4 Hz, 1H), 3.68 (s, 2H), 3.27 (q, J = 9.6 Hz, 2H), 2.45 (s, 3H). |
| 1B-26 | CDCl3: δ 8.75 (d, J = 7.6 Hz, 1H), 8.48 (s, 1H), 7.68 (s, 1H), 7.60 (d, J = 8.4 Hz, 2H), 7.51 (s, 1H), 7.46-7.41 (m, 3H), 6.98 (d, J = 11.6 Hz, 1H), 4.31 (m, 2H), 3.39 (q, J = 9.6 Hz, 2H), 2.42 (s, 3H). |
| 1B-27 | CDCl3: δ 8.75 (d, J = 7.6 Hz, 1H), 8.51 (s, 1H), 7.66 (d, J = 8.0 Hz, 2H), 7.60 (d, J = 7.2 Hz, 2H), 7.47-4.48 (m, 3H), 7.39-7.35 (m, 2H), 6.97 (d, J = 11.6 Hz, 1H), 4.33 (s, 2H), 3.40 (q, J = 9.6 Hz, 2H), 2.50 (s, 3H). |
| 1B-28 | CDCl3: δ 8.73 (d, J = 7.6 Hz, 1H), 8.41 (bs, 1H), 7.41 (d, J = 8.4 Hz, 2H), 7.28 (d, J = 8.8 Hz, 2H), 6.98 (d, J = 7.2 Hz, 1H), 4.26 (s, 2H), 3.39 (q, J = 9.6 Hz, 2H), 2.43 (s, 3H). |
| 1B-29 | CDCl3: δ 7.39 (d, J = 8.4 Hz, 2H), 7.36-7.30 (m, 2H), 7.23-7.18 (m, 2H), 7.12-7.07 (m, 3H), 3.52-3.41 (m, 2H), 3.26-3.18 (m, 5H), 2.51 (s, 3H). |
| 1B-30 | CDCl3: δ 7.37-7.34 (m, 2H), 7.29 (d, J = 8.0 Hz, 1H), 7.13-7.07 (m, 4H), 7.02 (d, J = 7.2 Hz, 1H), 3.50-3.46 (m, 2H), 3.28-3.19 (m, 5H), 2.51 (s, 3H). |
| 1B-31 | CDCl3: δ 8.02 (d, J = 8.4 Hz, 2H), 7.65 (d, J = 8.4 Hz, 2H), 7.51 (d, J = 8.4 Hz, 2H), 7.29 (d, J = 7.6 Hz, 1H), 7.14 (d, J = 8.0 Hz, 2H), 7.09 (d, J = 10.4 Hz, 1H), 3.54-3.41 (m, 2H), 3.29-3.18 (m, 5H), 2.64 (s, 3H), 2.51 (s, 3H). |
| 1B-32 | CDCl3: δ 7.41 (d, J = 8.4 Hz, 1H), 7.37-7.31 (m, 1H), 7.27 (s, 1H), 7.25 (s, 1H), 7.16-7.06 (m, 3H), 6.90 (d, J = 8.4 Hz, 1H), 3.50-3.46 (m, 2H), 3.28-3.20 (m, 5H), 2.51 (s, 3H). |
| 1B-33 | CDCl3: δ 7.53 (s, 1H), 7.45-7.41 (m, 3H), 7.36-7.28 (m, 3H), 7.12-7.07 (m, 3H), 3.48 (q, J = 15.2 Hz, 2H), 3.25-3.18 (m, 5H), 2.51 (s, 3H). |
| 1B-34 | CDCl3: δ 7.68-7.63 (m, 4H), 7.48 (d, J = 8.0 Hz, 2H), 7.30 (d, J = 8.0 Hz, 1H), 7.14 (d, J = 8.4 Hz, 2H), 7.09 (d, J = 10.0 Hz, 1H), 3.48 (q, J = 16.0 Hz, 2H), 3.26-3.19 (m, 5H), 2.51 (s, 3H). |
| 1B-35 | CDCl3: δ 7.55 (d, J = 8.8 Hz, 2H), 7.43 (d, J = 8.0 Hz, 2H), 7.30-7.25 (m, 3H), 7.12-7.07 (m, 3H), 3.48 (q, J = 16.8 Hz, 2H), 3.25-3.18 (m, 5H), 2.51 (s, 3H). |
| 1B-36 | CDCl3: δ 7.30 (d, J = 8.4 Hz, 1H), 7.17-7.10 (m, 2H), 7.00-6.94 (m, 3H), 4.08-3.87 (m, 2H), 3.64 (s, 2H), 3.43-3.29 (m, 3H), 3.21-3.14 (m, 2H), 2.50 (s, 3H). |
| 1B-37 | CDCl3: δ 7.54 (d, J = 8.8 Hz, 2H), 7.46-7.40 (m, 5H), 7.34 (d, J = 7.2 Hz, 2H), 7.08-7.01 (m, 2H), 4.19-3.94 (m, 2H), 3.67 (s, 3H), 3.04 (q, J = 9.6 Hz, 2H), 2.50 (s, 3H). |
| 1B-38 | CDCl3: δ 8.75 (d, J = 7.6 Hz, 1H), 7.63 (d, J = 8.4 Hz, 1H), 7.53 (d, J = 7.6 Hz, 1H), 7.49-7.44 (m, 4H), 7.43-7.28 (m, 1H), 7.25-7.19 (m, 2H), 6.97 (d, J = 11.2 Hz, 1H), 4.33 (s, 2H), 3.40 (q, J = 9.6 Hz, 2H), 2.42 (s, 3H). |
| 1B-39 | CDCl3: δ 7.14 (d, J = 7.2 Hz, 1H), 7.05-6.98 (m, 5H), 4.07-3.93 (m, 2H), 3.65 (s, 3H), 3.17 (q, J = 9.6 Hz, 2H), 2.48 (s, 3H). |
| 1B-40 | CDCl3: δ 8.50 (d, J = 8.0 Hz, 1H), 8.30 (bs, 1H), 7.75 (d, J = 8.4 Hz, 2H), 7.70 (d, J = 8.4 Hz, 2H), 7.59 (d, J = 7.6 Hz, 2H), 7.48-7.44 (m, 2H), 7.40 (d, J = 7.2 Hz, 1H), 7.03 (d, J = 11.6 Hz, 1H), 3.39 (q, J = 9.6 Hz, 2H), 2.44 (s, 3H). |
| 1B-41 | CDCl3: δ 7.56 (d, J = 7.2 Hz, 2H), 7.53 (d, J = 8.0 Hz, 2H), 7.48-7.44 (m, 2H), 7.40 (d, J = 7.6 Hz, 1H), 7.29 (d, J = 7.6 Hz, 2H), 7.15 (d, J = 7.2 Hz, 1H), 6.85 (d, J = 10.4 Hz, 1H), 3.39 (q, J = 9.6 Hz, 2H), 3.65 (s, 3H), 2.44 (s, 3H). |
| 1B-42 | CDCl3: δ 8.40 (d, J = 7.6 Hz, 1H), 7.63 (d, J = 7.2 Hz, 1H), 7.57-7.41 (m, 6H), 7.32 (d, J = 6.8 Hz, 1H), 7.05 (s, 1H), 6.90 (d, J = 9.6 Hz, 1H), 3.68 (s, 2H), 3.36 (q, J = 9.6 Hz, 2H), 2.39 (s, 3H). |
| 1B-43 | CDCl3: δ 8.75 (d, J = 7.6 Hz, 1H), 8.49 (bs, 1H), 7.84 (s, 1H), 7.78 (d, J = 8.0 Hz, 1H), 7.66 (d, J = 8.4 Hz, 2H), 7.63-7.55 (m, 2H), 7.47 (d, J = 8.0 Hz, 2H), 6.97 (d, J = 10.8 Hz, 1H), 4.33 (s, 2H), 3.39 (q, J = 9.6 Hz, 2H), 2.42 (s, 3H). |
| 1B-44 | CDCl3: δ 8.40 (d, J = 7.6 Hz, 1H), 7.45-7.40 (m, 4H), 7.32 (d, J = 6.8 Hz, 1H), 7.23-7.18 (m, 3H), 7.05 (s, 1H), 6.91 (d, J = 9.6 Hz, 1H), 3.70 (s, 2H), 3.35 (q, J = 9.6 Hz, 2H), 2.39 (s, 3H). |
| 1B-45 | CDCl3: δ 8.40 (d, J = 7.6 Hz, 1H), 7.46-7.34 (m, 7H), 7.32-7.29 (m, 2H), 7.04 (s, 1H), 6.89 (d, J = 9.6 Hz, 1H), 3.71 (s, 2H), 3.35 (q, J = 9.6 Hz, 2H), 2.39 (s, 3H). |
| 1B-46 | CDCl3: δ 8.65 (d, J = 8.0 Hz, 1H), 8.29 (s, 1H), 7.64 (d, J = 7.6 Hz, 1H), 7.54 (d, J = 8.8 Hz, 2H), 7.52-7.43 (m, 5H), 7.35 (d, J = 6.0 Hz, 1H), 6.96 (d, J = 9.6 Hz, 1H), 4.20 (s, 2H), 3.37 (q, J = 9.6 Hz, 2H), 2.42 (s, 3H). |
| 1B-47 | CDCl3: δ 8.66 (d, J = 7.6 Hz, 1H), 8.28 (bs, 1H), 7.48-7.42 (m, 4H), 7.35 (d, J = 6.0 Hz, 2H), 7.23 (d, J = 8.8 Hz, 2H), 6.95 (d, J = 11.2 Hz, 1H), 4.22 (s, 2H), 3.37 (q, J = 9.6 Hz, 2H), 2.42 (s, 3H). |
| 1B-48 | CDCl3: δ 7.60 (d, J = 8.0 Hz, 1H), 7.48 (t, J = 7.6 Hz, 1H), 7.38-7.28 (m, 6H), 7.15 (d, J = 7.6 Hz, 1H), 6.99 (d, J = 7.6 Hz, 1H), 6.92 (d, J = 10.4 Hz, 1H), 3.31 (s, 2H), 3.16 (s, 3H), 3.12 (q, J = 9.6 Hz, 2H), 2.43 (s, 3H). |
| 1B-49 | CDCl3: δ 7.33-7.27 (m, 5H), 7.16 (d, J = 7.2 Hz, 1H), 7.07 (d, J = 7.6 Hz, 1H), 6.93 (d, J = 8.0 Hz, 1H), 6.90 (d, J = 10.4 Hz, 1H), 3.38 (s, 2H), 3.16 (s, 3H), 3.09 (q, J = 9.6 Hz, 2H), 2.43 (s, 3H). |
| 1B-50 | CDCl3: δ 7.39-7.29 (m, 5H), 7.18 (d, J = 8.4 Hz, 1H), 7.15 (d, J = 7.6 Hz, 1H), 7.05 (d, J = 7.6 Hz, 1H), 7.01 (d, J = 7.6 Hz, 1H), 6.93 (d, J = 10.0 Hz, 1H), 3.33 (s, 2H), 3.16 (s, 3H), 3.09 (q, J = 9.6 Hz, 2H), 2.44 (s, 3H). |

TABLE 4-continued

| S. No. | ¹H NMR |
|---|---|
| 1B-51 | CDCl3: δ 7.57 (d, J = 7.6 Hz, 1H), 7.47 (t, J = 7.6 Hz, 2H), 7.43 (d, J = 7.6 Hz, 1H), 7.40-7.36 (m, 1H), 7.31 (d, J = 8.4 Hz, 1H), 7.22 (d, J = 7.6 Hz, 1H), 7.16 (d, J = 7.2 Hz, 1H), 7.09 (d, J = 7.6 Hz, 1H), 6.89 (d, J = 6.0 Hz, 1H), 6.82 (d, J = 12.4 Hz, 1H), 3.39-3.67 (m, 2H), 3.62 (s, 3H), 3.08-2.86 (m, 2H), 2.43 (s, 3H). |
| 1B-52 | CDCl3: δ 7.49 (d, J = 7.6 Hz, 1H), 7.38-7.28 (m, 3H), 7.16 (d, J = 8.0 Hz, 1H), 7.09 (d, J = 7.2 Hz, 1H), 6.94 (d, J = 7.6 Hz, 1H), 6.89 (d, J = 10.0 Hz, 1H), 6.82 (d, J = 7.6 Hz, 1H), 6.74 (s, 1H), 3.94-3.72 (m, 2H), 3.62 (s, 3H), 3.07-2.91 (m, 2H), 2.44 (s, 3H). |
| 1B-53 | CDCl3: δ 10.89 (bs, 1H), 7.93 (d, J = 8.0 Hz, 2H), 7.82 (d, J = 8.4 Hz, 2H), 7.62 (d, J = 7.6 Hz, 1H), 7.29 (d, J = 11.2 Hz, 1H), 3.87 (q, J = 9.6 Hz, 2H), 2.40 (s, 3H). |
| 1B-54 | CDCl3: δ 7.82 (d, J = 7.2 Hz, 1H), 7.73 (d, J = 8.0 Hz, 1H), 7.51 (d, J = 7.6 Hz, 1H), 7.32 (d, J = 7.6 Hz, 1H), 7.27 (d, J = 7.6 Hz, 1H), 7.11 (d, J = 10.8 Hz, 1H), 3.89 (q, J = 9.6 Hz, 2H), 3.17 (s, 3H), 2.34 (s, 3H). |
| 1B-55 | CDCl3: δ 7.51 (d, J = 7.2 Hz, 1H), 7.34-7.28 (m, 4H), 7.09 (d, J = 7.6 Hz, 1H), 6.92-6.90 (m, 2H), 6.83 (d, J = 10.0 Hz, 1H), 6.73 (d, J = 7.6 Hz, 1H), 3.99-3.82 (m, 2H), 3.61 (s, 3H), 3.03-2.89 (m, 2H), 2.43 (s, 3H). |
| 1B-56 | CDCl3: δ 10.02 (bs, 1H), 7.56-7.50 (m, 3H), 7.08-6.96 (m, 3H), 5.82 (d, J = 12.4 Hz, 1H), 3.30 (q, J = 9.6 Hz, 2H), 2.45 (s, 3H). |
| 1B-57 | CDCl3: δ 8.49 (d, J = 8.0 Hz, 1H), 7.59-7.31 (m, 8H), 7.22 (d, J = 8.0 Hz, 1H), 6.92 (d, J = 11.6 Hz, 1H), 3.83 (s, 2H), 3.35 (q, J = 9.6 Hz, 2H), 2.40 (s, 3H). |
| 1B-58 | CDCl3: δ 8.50 (d, J = 7.6 Hz, 1H), 7.61-7.55 (m, 4H), 7.51-7.43 (m, 3H), 7.38-7.30 (m, 3H), 6.90 (d, J = 11.2 Hz, 1H), 3.83 (s, 2H), 3.38 (q, J = 9.6 Hz, 2H), 2.39 (s, 3H). |
| 1B-59 | CDCl3: δ 8.50 (d, J = 7.6 Hz, 1H), 7.83 (s, 1H), 7.77 (d, J = 7.6 Hz, 1H), 7.63-7.50 (m, 5H), 7.38 (d, J = 7.6 Hz, 1H), 7.37 (s, 1H), 6.92 (d, J = 11.2 Hz, 1H), 3.84 (s, 2H), 3.38 (q, J = 9.6 Hz, 2H), 2.40 (s, 3H). |
| 1B-60 | CDCl3: δ 8.50 (d, J = 8.0 Hz, 1H), 7.70 (m, 4H), 7.57 (d, J = 8.0 Hz, 2H), 7.51 (t, J = 7.6 Hz, 1H), 7.38 (d, J = 7.6 Hz, 1H), 7.33 (bs, 1H), 6.92 (d, J = 11.6 Hz, 1H), 3.84 (s, 2H), 3.37 (q, J = 9.6 Hz, 2H), 2.40 (s, 3H). |
| 1B-61 | CDCl3: δ 7.44-7.40 (m, 3H), 7.34-7.28 (m, 3H), 7.19 (s, 1H), 7.11 (bs, 1H), 7.07 (d, J = 7.6 Hz, 1H), 7.28 (d, J = 10.0 Hz, 1H), 3.52 (q, J = 9.6 Hz, 2H), 3.24-3.17 (m, 5H), 2.41 (s, 3H). |
| 1B-62 | CDCl3: δ 7.50 (d, J = 7.6 Hz, 1H), 7.41 (t, J = 7.6 Hz, 3H), 7.35-7.30 (m, 3H), 7.13 (bs, 1H), 6.90 (d, J = 10.0 Hz, 1H), 3.52 (q, J = 9.6 Hz, 2H), 3.53 (q, J = 9.6 Hz, 2H), 3.22-3.13 (m, 5H), 2.41 (s, 3H). |
| 1B-63 | CDCl3: δ 7.73 (s, 1H), 7.69 (d, J = 7.2 Hz, 1H), 7.59 (d, J = 8.4 Hz, 1H), 7.53 (t, J = 6.8 Hz, 1H), 7.43 (d, J = 7.6 Hz, 1H), 7.34 (t, J = 7.6 Hz, 1H), 7.28 (d, J = 7.6 Hz, 1H), 7.15 (s, 1H), 7.08 (d, J = 8.0 Hz, 1H), 7.02 (d, J = 10.0 Hz, 1H), 3.53 (q, J = 9.6 Hz, 2H), 3.25-3.17 (m, 5H), 2.43 (s, 3H). |
| 1B-64 | CDCl3: δ 7.77 (d, J = 8.4 Hz, 2H), 7.61 (d, J = 8.4 Hz, 2H), 7.43 (d, J = 8.0 Hz, 1H), 7.34 (t, J = 8.0 Hz, 1H), 7.29 (d, J = 8.0 Hz, 1H), 7.19 (s, 1H), 7.07 (d, J = 7.6 Hz, 1H), 7.03 (d, J = 10.4 Hz, 1H), 3.53 (q, J = 9.6 Hz, 2H), 3.25-3.18 (m, 5H), 2.44 (s, 3H). |
| 1B-65 | CDCl3: δ 7.51 (d, J = 8.4 Hz, 2H), 7.39 (d, J = 8.4 Hz, 1H), 7.32 (d, J = 7.6 Hz, 1H), 7.27 (t, J = 8.8 Hz, 2H), 7.24 (s, 1H), 7.13 (s, 1H), 7.03 (d, J = 7.2 Hz, 2H), 3.53 (q, J = 9.6 Hz, 2H), 3.23-3.16 (m, 5H), 2.43 (s, 3H). |
| 1B-66 | CDCl3: δ 8.50 (d, J = 7.6 Hz, 1H), 7.50-7.46 (m, 2H), 7.39-7.37 (m, 3H), 7.32 (s, 1H), 7.24 (d, J = 7.6 Hz, 2H), 6.92 (d, J = 11.6 Hz, 1H), 3.82 (s, 2H), 3.38 (q, J = 9.6 Hz, 2H), 2.40 (s, 3H). |
| 1B-67 | CDCl3: δ 8.50 (d, J = 8.0 Hz, 1H), 7.50-7.46 (m, 2H), 7.39-7.36 (m, 3H), 7.32-7.27 (m, 3H), 6.91 (d, J = 11.6 Hz, 1H), 3.82 (s, 2H), 3.38 (q, J = 9.6 Hz, 2H), 2.40 (s, 3H). |
| 1B-68 | CDCl3: δ 10.00 (bs, 1H), 7.61 (d, J = 8.8 Hz, 1H), 7.54 (s, 1H), 7.47-7.13 (m, 7H), 3.81-3.73 (m, 4H), 2.36 (s, 3H). |
| 1B-69 | CDCl3: δ 8.49 (d, J = 7.2 Hz, 1H), 7.68 (s, 1H), 7.52-7.47 (m, 4H), 7.42 (d, J = 8.4 Hz, 1H), 7.36 (d, J = 6.8 Hz, 1H), 7.31 (s, 1H), 6.92 (d, J = 11.6 Hz, 1H), 3.82 (s, 2H), 3.38 (q, J = 9.6 Hz, 2H), 2.40 (s, 3H). |
| 1B-70 | CDCl3: δ 8.49 (d, J = 8.0 Hz, 1H), 7.50-7.48 (m, 2H), 7.46 (d, J = 2H), 7.39 (d, J = 8.0 Hz, 1H), 7.35 (t, J = 7.6 Hz, 1H), 7.31 (bs, 1H), 6.92 (d, J = 11.6 Hz, 1H), 3.82 (s, 2H), 3.38 (q, J = 9.6 Hz, 2H), 2.40 (s, 3H). |
| 1B-71 | CDCl3: δ 8.49 (d, J = 7.6 Hz, 1H), 7.58 (s, 1H), 7.55-7.46 (m, 4H), 7.39-7.32 (m, 4H), 6.92 (d, J = 11.6 Hz, 1H), 3.83 (s, 2H), 3.38 (q, J = 9.6 Hz, 2H), 2.40 (s, 3H). |
| 1B-72 | CDCl3: δ 7.46 (s, 1H), 7.40-7.38 (m, 2H), 7.34 (d, J = 2H), 7.33-7.27 (m, 3H), 7.09 (s, 1H), 7.05 (d, J = 7.6 Hz, 1H), 7.02 (d, J = 10.4 Hz, 1H), 3.52 (q, J = 9.6 Hz, 2H), 3.24-3.17 (m, 5H), 2.44 (s, 3H). |
| 1B-73 | CDCl3: δ 7.37 (d, J = 8.4 Hz, 1H), 7.32-7.27 (m, 4H), 7.23 (s, 1H), 7.07-7.00 (m, 3H), 3.52 (q, J = 9.6 Hz, 2H), 3.24-3.16 (m, 5H), 2.46 (s, 3H). |
| 1B-74 | CDCl3: δ 7.58 (s, 1H), 7.48 (d, J = 8.4 Hz, 1H), 7.36-7.27 (m, 4H), 7.11 (s, 1H), 7.06-7.02 (m, 2H), 3.53 (q, J = 9.6 Hz, 2H), 3.26-3.19 (m, 5H), 2.46 (s, 3H). |
| 1B-75 | CDCl3: δ 8.95 (d, J = 7.6 Hz, 1H), 8.33 (bs, 1H), 7.82-7.73 (m, 4H), 7.19 (d, J = 10.8 Hz, 1H), 3.90 (q, J = 9.6 Hz, 2H), 2.70 (s, 3H). |
| 1B-76 | CDCl3: δ 7.45 (d, J = 6.8 Hz, 1H), 7.30-7.26 (m, 3H), 7.23-7.17 (m, 2H), 7.07-7.03 (m, 3H), 3.49 (q, J = 9.6 Hz, 2H), 3.41-3.18 (m, 5H), 2.45 (s, 3H). |
| 1B-77 | CDCl3: δ 7.46 (s, 1H), 7.29-7.26 (m, 3H), 7.22 (d, J = 8.0 Hz, 2H), 7.04-7.02 (m, 3H), 3.50 (q, J = 9.6 Hz, 2H), 3.41-3.18 (m, 5H), 2.46 (s, 3H). |
| 1B-78 | CDCl3: δ 7.51-7.47 (m, 1H), 7.39-7.34 (m, 3H), 7.32-7.29 (m, 2H), 7.08 (d, J = 8.0 Hz, 2H), 7.03 (d, J = 10.0 Hz, 1H), 3.50 (q, J = 9.6 Hz, 2H), 3.27-3.20 (m, 5H), 2.47 (s, 3H). |
| 1B-79 | CDCl3: δ 8.48 (d, J = 7.6 Hz, 1H), 7.34 (d, J = 8.4 Hz, 2H), 7.26 (s, 1H), 7.15 (d, J = 8.4 Hz, 2H), 6.93 (d, J = 7.6 Hz, 1H), 6.70-6.33 (m, 1H), 3.74 (s, 2H), 3.38 (q, J = 9.6 Hz, 2H), 2.40 (s, 3H). |
| 1B-80 | CDCl3: δ 7.29 (d, J = 7.6 Hz, 1H), 7.07 (d, J = 10.4 Hz, 1H), 7.04-6.97 (m, 4H), 6.64-6.27 (m, 1H), 3.41 (q, J = 9.6 Hz, 2H), 3.28-3.21 (m, 5H), 2.50 (s, 3H). |
| 1B-81 | CDCl3: δ 8.95 (d, J = 7.6 Hz, 1H), 7.34 (d, J = 8.4 Hz, 2H), 7.30 (bs, 1H), 7.16 (d, J = 8.4 Hz, 2H), 7.06 (d, J = 10.8 Hz, 1H), 6.71-6.34 (m, 1H), 3.39 (q, J = 9.6 Hz, 2H), 3.77 (s, 2H), 2.64 (s, 3H). |
| 1B-82 | CDCl3: δ 8.88 (d, J = 7.6 Hz, 1H), 7.19 (d, J = 9.6 Hz, 1H), 7.10-6.99 (m, 4H), 6.66-6.29 (m, 1H), 3.93 (q, J = 9.6 Hz, 2H), 3.49-3.41 (m, 2H), 3.22 (s, 3H), 2.72 (s, 3H). |
| 1B-83 | CDCl3: δ 7.75 (s, 1H), 7.17-6.99 (m, 5H), 6.65-6.28 (m, 1H), 3.93 (q, J = 9.6 Hz, 2H), 3.49-3.41 (m, 2H), 3.24 (s, 3H), 2.42 (s, 3H). |
| 1B-84 | CDCl3: δ 8.97 (s, 1H), 7.69 (d, J = 8.0 Hz, 2H), 7.41 (d, J = 8.0 Hz, 2H), 7.30 (bs, 1H), 7.07 (d, J = 11.2 Hz, 1H), 3.89 (q, J = 9.6 Hz, 2H), 3.81 (s, 2H), 2.64 (s, 3H). |
| 1B-85 | CDCl3: δ 8.97 (d, J = 7.6 Hz, 1H), 7.83 (s, 1H), 7.77 (d, J = 7.2 Hz, 1H), 7.64-7.50 (m, 5H), 7.38 (d, J = 7.2 Hz, 2H), 7.05 (d, J = 10.8 Hz, 1H), 3.93-3.86 (m, 4H), 2.63 (s, 3H). |
| 1B-86 | CDCl3: δ 8.46 (d, J = 7.6 Hz, 1H), 8.29 (bs, 1H), 7.74 (d, J = 8.8 Hz, 2H), 7.33 (d, J = 8.4 Hz, 2H), 7.03 (d, J = 11.6 Hz, 1H), 3.37 (q, J = 9.6 Hz, 2H), 2.44 (s, 3H). |

TABLE 4-continued

| S. No. | $^1$H NMR |
|---|---|
| 1B-87 | CDCl3: δ 7.26-7.23 (m, 3H), 7.15 (d, J = 8.4 Hz, 2H), 6.82 (d, J = 10.4 Hz, 1H), 3.31-3.25 (m, 5H), 2.45 (s, 3H). |
| 1B-88 | CDCl3: δ 8.94 (d, J = 7.6 Hz, 1H), 8.33 (bs, 1H), 7.74 (d, J = 8.8 Hz, 2H), 7.34 (d, J = 8.0 Hz, 2H), 7.18 (d, J = 11.2 Hz, 1H), 3.91 (q, J = 9.6 Hz, 2H), 2.68 (s, 3H). |
| 1B-89 | CDCl3: δ 7.88 (d, J = 7.2 Hz, 1H), 7.32 (d, J = 8.4 Hz, 2H), 7.20 (d, J = 8.0 Hz, 2H), 7.05 (d, J = 9.6 Hz, 1H), 3.92 (q, J = 9.6 Hz, 2H), 3.27 (s, 3H), 2.71 (s, 3H). |
| 1B-90 | CDCl3: δ 8.49 (d, J = 7.6 Hz, 1H), 7.50-7.41 (m, 3H), 7.32 (bs, 1H), 7.28 (d, J = 7.6 Hz, 1H), 7.06 (d, J = 6.4 Hz, 2H), 6.92 (s, 1H), 6.89 (d, J = 10.8 Hz, 1H), 6.00 (s, 2H), 3.81 (s, 2H), 3.37 (q, J = 9.6 Hz, 2H), 3.39 (s, 3H). |
| 1B-91 | CDCl3: δ 8.49 (d, J = 7.6 Hz, 1H), 7.55 (d, J = 9.2 Hz, 2H), 7.49 (t, J = 7.6 Hz, 1H), 7.43-7.28 (m, 5H), 7.05 (t, J = 9.2 Hz, 1H), 6.91 (d, J = 11.2 Hz, 1H), 3.83 (s, 2H), 3.37 (q, J = 9.6 Hz, 2H), 2.40 (s, 3H). |
| 1B-92 | CDCl3: δ 8.49 (d, J = 8.0 Hz, 1H), 7.56-7.45 (m, 5H), 7.39 (d, J = 8.4 Hz, 2H), 7.31 (d, J = 7.6 Hz, 2H), 6.91 (d, J = 11.6 Hz, 1H), 3.82 (s, 2H), 3.37 (q, J = 9.6 Hz, 2H), 2.99 (q, J = 7.2 Hz, 2H), 2.39 (s, 3H), 1.35 (t, J = 7.2 Hz, 3H). |
| 1B-93 | CDCl3: δ 8.49 (d, J = 8.0 Hz, 1H), 7.47 (t, J = 8.0 Hz, 1H), 7.39 (d, J = 6.8 Hz, 2H), 7.37-7.33 (m, 3H), 7.33 (s, 1H), 7.29 (s, 1H), 7.22 (t, J = 6.4 Hz, 1H), 6.91 (d, J = 11.6 Hz, 1H), 3.81 (s, 2H), 3.37 (q, J = 9.6 Hz, 2H), 2.39 (s, 3H), 2.35 (s, 3H). |
| 1B-94 | CDCl3: δ 8.50 (d, J = 8.0 Hz, 1H), 7.68 (s, 4H), 7.63 (t, J = 7.2 Hz, 4H), 7.52-7.44 (m, 3H), 7.38-7.33 (m, 3H), 6.91 (d, J = 11.6 Hz, 1H), 3.85 (s, 2H), 3.37 (q, J = 9.6 Hz, 2H), 2.39 (s, 3H). |
| 1B-95 | CDCl3: δ 8.49 (d, J = 7.6 Hz, 1H), 7.47 (d, J = 8.4 Hz, 2H), 7.69 (d, J = 8.0 Hz, 2H), 7.57-7.50 (m, 3H), 7.40 (d, J = 7.2 Hz, 1H), 7.32 (bs, 1H), 6.93 (d, J = 11.6 Hz, 1H), 3.83 (s, 2H), 3.37 (q, J = 9.6 Hz, 2H), 2.40 (s, 3H). |
| 1B-96 | CDCl3: δ 7.70 (d, J = 8.4 Hz, 2H), 7.62 (d, J = 8.4 Hz, 2H), 7.43 (d, J = 7.6 Hz, 1H), 7.36 (d, J = 7.6 Hz, 1H), 7.30 (d, J = 7.6 Hz, 1H), 7.22 (s, 1H), 7.07 (d, J = 7.2 Hz, 1H), 7.04 (d, J = 10.4 Hz, 1H), 3.52 (q, J = 9.6 Hz, 2H), 3.27-3.18 (m, 5H), 2.46 (s, 3H). |
| 1B-97 | CDCl3: δ 7.66-7.63 (m, 4H), 7.59 (d, J = 8.0 Hz, 2H), 7.48-7.44 (m, 3H), 7.38-7.30 (m, 3H), 7.18 (s, 1H), 7.02-7.00 (m, 2H), 3.54 (q, J = 9.6 Hz, 2H), 3.22-3.15 (m, 5H), 2.39 (s, 3H). |
| 1B-98 | CDCl3: δ 7.34-7.27 (m, 4H), 7.20-7.14 (m, 3H), 7.03-6.99 (m, 3H), 3.52 (q, J = 9.6 Hz, 2H), 3.22 (s, 3H), 3.14 (q, J = 9.6 Hz, 2H), 2.44 (s, 3H), 2.36 (s, 3H). |
| 1B-99 | CDCl3: δ 7.44-7.35 (m, 5H), 7.29 (d, J = 7.6 Hz, 1H), 7.24 (d, J = 7.6 Hz, 2H), 7.12 (s, 1H), 7.02-6.98 (m, 1H), 3.53 (q, J = 9.6 Hz, 2H), 3.21-3.14 (m, 5H), 2.98 (q, J = 7.2 Hz, 2H), 2.42 (s, 3H), 1.05 (t, J = 7.2 Hz, 3H). |
| 1B-100 | CDCl3: δ 7.41-7.34 (m, 2H), 7.33-7.27 (m, 3H), 7.18 (d, J = 10.4 Hz, 1H), 7.10 (s, 1H), 7.06-7.00 (m, 3H), 3.53 (q, J = 9.6 Hz, 2H), 3.23-3.16 (m, 5H), 2.44 (s, 3H). |
| 1B-101 | CDCl3: δ 7.34 (d, J = 7.6 Hz, 1H), 7.28 (s, 1H), 7.23 (d, J = 7.6 Hz, 1H), 7.05 (s, 1H), 7.01 (d, J = 10.4 Hz, 1H), 6.98-6.99 (m, 3H), 6.85 (d, J = 8.4 Hz, 1H), 5.99 (s, 2H), 3.52 (q, J = 9.6 Hz, 2H), 3.21-3.14 (m, 5H), 2.44 (s, 3H). |
| 1B-102 | CDCl3: δ 8.45 (d, J = 7.6 Hz, 1H), 7.70-7.68 (m, 2H), 7.48-7.46 (m, 2H), 7.23 (bs, 1H), 6.96 (d, J = 11.6 Hz, 1H), 3.81 (s, 2H), 3.36 (q, J = 9.6 Hz, 2H), 2.41 (s, 3H). |

Below are Preparation Examples in which the "parts" refers to "parts by weight."

Preparation Example 1: Emulsions 10 parts of each compound of the invention was dissolved in 45 parts of Solvesso 150 and 35 parts of N-methylpyrrolidone. 10 parts of an emulsifier (trade name: Sorpol 3005X, produced by Toho Chemical Industry Co., Ltd.) was added thereto. The mixtures were mixed by stirring to give 10% emulsions.

Preparation Example 2: Wettable Powders 20 parts of each compound of the invention was added to a mixture of 2 parts of sodium lauryl sulfate, 4 parts of sodiumlignin sulfonate, 20 parts of fine powder of synthetic hydrated silicon dioxide, and 54 parts of clay. The mixtures were mixed by stirring with a juice mixer to give 20% wettable powders.

Preparation Example 3: Granules 2 parts of sodium dodecylbenzenesulfonate, 10 parts of bentonite, and 83 parts of clay were added to 5 parts of each compound of the invention, and each mixture was sufficiently mixed by stirring. An appropriate amount of water was added thereto. The resulting mixtures were further stirred and granulated with a granulator. The granules were air-dried to give 5% granules.

Preparation Example 4: Dusts 1 part of each compound of the invention was dissolved in an appropriate amount of acetone. 5 parts of fine powder of synthetic hydrated silicon dioxide, 0.3 parts of acidic isopropyl phosphate (PAP), and 93.7 parts of clay were added thereto. The mixtures were mixed by stirring with a juice mixer, and acetone was removed by evaporation to give 1% dust.

Preparation Example 5: Flowable Preparations 20 parts of each compound of the invention was mixed with 20 parts of water containing 3 parts of polyoxyethylene tristyrylphenyl ether phosphoric acid ester triethanolamine and 0.2 parts of Rhodorsil 426R. The mixtures were subjected to wet pulverization with a DYNO-Mill, and mixed with 60 parts of water containing 8 parts of propylene glycol and 0.32 parts of xanthan gum to give 20% suspensions in water.

Test Examples are given below to demonstrate that the compounds of the invention are useful as an active ingredient for miticides.

Test Example 1 (Miticidal Test on Two-Spotted Spider Mites)

A piece of non-woven fabric (4.5×5.5 cm) was suspended inside a plastic cup through an incision made in the lid of the plastic cup. After water was poured into the cup, the cup was covered with the lid. A kidney bean leaf (about 3.5×4.5 cm)

was then placed on the sufficiently soaked, non-woven fabric. Another kidney bean leaf with two-spotted spider mites (about 30 mite samples) was placed on top of the first leaf, and the fabric and leaves were placed in a thermostatic chamber having a temperature of 25±2° C. and a humidity of 40%.

Miticidal formulations containing the compound of the invention (200 ppm) were prepared by adding an aqueous solution (100 ppm) of Sorpol 355 (manufactured by Tobo Kagaku Co. Ltd.) to a methanol solution of the compound of the invention.

These miticidal formulations were sprayed onto the leaves, and the leaves were air-dried and placed in a thermostatic chamber (25±2° C. and a humidity of 50%). The mortality rate of the two-spotted spider mites was calculated after 2 days.

The compounds that exhibited the mortality rate of 50% or more are as follows:
Compound Nos.: 1A-2, 1A-5, 1A-8, 1A-12, 1A-13, 1A-14, 1A-15, 1A-20, 1A-23, 1A-24, 1A-27, 1A-28, 1A-30, 1A-33, 1A-42, 1A-43, 1A-45, 1A-46, 1A-47, 1A-48, 1A-49, 1A-50, 1A-51, 1A-52, 1A-53, 1A-54, 1A-55, 1A-56, 1A-57, 1A-58, 1A-59, 1A-60, 1A-62, 1A-63, 1A-65, 1A-67, 1A-68, 1A-72, 1A-73, 1A-74, 1A-75, 1A-76, 1A-77, 1A-78, 1A-82, 1A-83, 1A-85, 1A-86, 1A-87, 1A-88, 1A-90, 1A-91, 1A-92, 1A-93, 1A-94, 1A-95, 1A-96, 1A-97, 1A-103, 1A-104, 1A-107, 1A-108, 1A-109, 1A-111, 1A-112, 1A-113, 1A-114, 1A-116, 1A-117, 1A-118, 1A-119, 1A-120, 1A-121, 1A-122, 1A-123, 1A-126, 1A-127, 1A-128, 1B-1, 1B-2, 1B-3, 1B-5, 1B-7, 1B-8, 1B-9, 1B-10, 1B-11, 1B-12, 1B-15, 1B-16, 1B-17, 1B-18, 1B-19, 1B-20, 1B-22, 1B-23, 1B-24, 1B-25, 1B-26, 1B-27, 1B-28, 1B-29, 1B-30, 1B-32, 1B-33, 1B-34, 1B-35, 1B-36, 1B-37, 1B-38, 1B-39, 1B-41, 1B-43, 1B-48, 1B-49, 1B-50, 1B-54, 1B-55, 1B-56, 1B-57, 1B-58, 1B-59, 1B-61, 1B-62, 1B-63, 1B-64, 1B-65, 1B-66, 1B-67, 1B-68, 1B-69, 1B-70, 1B-71, 1B-72, 1B-73, 1B-74, 1B-76, 1B-77, 1B-78, 1B-79, 1B-80, 1B-82, 1B-83, 1B-87, 1B-90, 1B-96, 1B-97, 1B-98, 1B-99, 1B-100, 1B-101, 1B-102.

Test Example 2 (Ovicidal Test on Two-Spotted Spider Mites)

A piece of non-woven fabric (4.5×5.5 cm) was suspended inside a plastic cup through an incision made in the lid of the plastic cup. After water was poured into the cup, the cup was covered with the lid. A kidney bean leaf (about 3.5×4.5 cm) was then placed on the sufficiently soaked, non-woven fabric. Twenty female adults of two-spotted spider mite were placed on the top of the leaf, and the fabric and leaf were placed in a thermostatic chamber having a temperature of 25±2° C. and a humidity of 40% and 16L8D.

The next day, after the number of the female adults was adjusted once more to 20, 2 ml of a miticidal formulation containing the compound of the invention (200 ppm) prepared in the same manner as in test example 1 was sprayed onto the leaf, and the leaf was air-dried and placed in a thermostatic chamber (25±2° C. and a humidity of 50%). The ovicidal rate of the two-spotted spider mites was calculated 6 days after the spraying of the miticidal formulation. The compounds that exhibited a mortality of 50% or more at 500 ppm are as follows:
Compound Nos.: 1A-2, 1A-8, 1A-12, 1A-13, 1A-14, 1A-20, 1A-23, 1A-27, 1A-33, 1A-42, 1A-43, 1A-47, 1A-48, 1A-49, 1A-50, 1A-51, 1A-52, 1A-53, 1A-54, 1A-55, 1A-56, 1A-57, 1A-58, 1A-59, 1A-60, 1A-61, 1A-63, 1A-65, 1A-67, 1A-68, 1A-69, 1A-70, 1A-71, 1A-72, 1A-73, 1A-74, 1A-76, 1A-77, 1A-78, 1A-82, 1A-83, 1A-85, 1A-86, 1A-87, 1A-88, 1A-90, 1A-91, 1A-93, 1A-94, 1A-95, 1A-96, 1B-1, 1B-2, 1B-3, 1B-5, 1B-7, 1B-8, 1B-9, 1B-10, 1B-11, 1B-12, 1B-15, 1B-16, 1B-17, 1B-18, 1B-19, 1B-20, 1B-22, 1B-23, 1B-24, 1B-25, 1B-26, 1B-27, 1B-28, 1B-29, 1B-30, 1B-32, 1B-33, 1B-34, 1B-35, 1B-36, 1B-37, 1B-38, 1B-39, 1B-41, 1B-43, 1B-48, 1B-49, 1B-50, 1B-54, 1B-55, 1B-56, 1B-57, 1B-58, 1B-59, 1B-61, 1B-62, 1B-63, 1B-64, 1B-65, 1B-66, 1B-67, 1B-68, 1B-69, 1B-70, 1B-71, 1B-72, 1B-73, 1B-74, 1B-76, 1B-77, 1B-78, 1B-79, 1B-80, 1B-82, 1B-83, 1B-86, 1B-87, 1B-88, 1B-90, 1B-96, 1B-97, 1B-98, 1B-99, 1B-100, 1B-101.

(Note)
It is understood that patents, patent applications and literatures cited herein are incorporated herein by reference, as if the contents thereof are specifically described herein. The present application claims priority to PCT Application No. PCT/IB2016/055523 and Indian Patent Application No. 201611024522, the entire content of which is incorporated herein by reference.

INDUSTRIAL APPLICABILITY

The present invention provides novel benzylamide compounds, methods for producing the same, and miticides and thus the present inventions are particularly useful in the agricultural industry.

The invention claimed is:
1. A benzylamide compound represented by Formula (1):

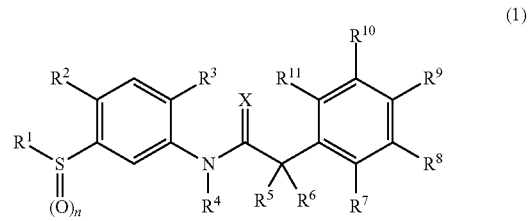

or a salt thereof,
wherein $R^1$ represents $C_{1-6}$ haloalkyl;
$R^2$ and $R^3$ are identical or different and each represent halogen, cyano, or $C_{1-6}$ alkyl;
$R^4$ represents hydrogen, formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkylcarbonyl, $C_{1-6}$ haloalkylcarbonyl, $C_{1-6}$ alkoxycarbonyl, $C_{1-6}$ haloalkoxy carbonyl, arylcarbonyl, aryloxycarbonyl, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, aryl, aryl $C_{1-6}$ alkyl, arylsulfonyl, arylsulfinyl, arylthio, or heterocyclic, all the substituents defined as $R^4$ may optionally be further substituted;
$R^5$ and $R^6$ are identical or different and each represent hydrogen, halogen, $C_{1-6}$ alkyl, or $C_{1-6}$ haloalkyl; $R^5$ and $R^6$, taken together with the carbon atom to which they bond, may bond to each other to form a 3- to 8-membered ring, via or not via at least one heteroatom;
$R^7$, $R^8$, $R^9$, $R^{10}$, and R are identical or different and each represent hydrogen, halogen, nitro, cyano, hydroxyl, formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkylcarbonyl, $C_{1-6}$ haloalkylcarbonyl, arylcarbonyl, aryloxycarbonyl, $C_{1-6}$ alkoxycarbonyl, $C_{1-6}$ haloalkoxycarbonyl, $C_{1-6}$ cyanoalkyl, $C_{1-6}$ cyanoalkoxy, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, $C_{3-8}$ cycloalkylsulfonyl, $C_{3-8}$ cycloalkylsulfinyl, $C_{3-8}$ cycloalkylthio, $C_{3-8}$ cycloalkyl $C_{1-6}$ alkylsulfonyl, $C_{3-8}$ cycloalkyl $C_{1-6}$ alkylsulfinyl, $C_{3-8}$ cycloalkyl $C_{1-6}$ alkylthio, $C_{1-6}$ alkoxy $C_{1-6}$ alkylsulfonyl, $C_{1-6}$ alkoxy $C_{1-6}$ alkylsulfinyl, $C_{1-6}$ alkoxy $C_{1-6}$ alkylthio, $C_{2-6}$ alkenyloxy, $C_{2-6}$ haloalkenyloxy, $C_{2-6}$ alkynyloxy, $C_{2-6}$ haloalkynyloxy, $C_{1-6}$ alkylsulfonyloxy, $C_{1-6}$ haloalkylsulfonyloxy, $C_{1-6}$ alkylsulfinyloxy, $C_{1-6}$ haloalkylsulfinyloxy, carboxyl, OCN, SCN, $SF_5$, substituted or unsubstituted amino, aryl, aryl $C_{1-6}$ alkyl, aryloxy, aryl $C_{1-6}$ alkoxy, arylsulfonyl, arylsulfinyl, arylthio, aryl $C_{1-6}$ alkylsulfonyl, aryl $C_{1-6}$ alkylsulfinyl, aryl $C_{1-6}$ alkylthio, heterocyclic, heterocyclic $C_{1-6}$ alkyl, or heterocyclic oxy, all of which may optionally be further substituted;

$R^7$ and $R^8$, $R^8$ and $R^9$, $R^9$ and $R^{10}$, or $R^{10}$ and $R^{11}$, taken together with the benzene ring to which they bond, may bond to each other to form a 3- to 8-membered ring via or not via at least one heteroatom;

X represents oxygen or sulfur; and n represents an integer of 0 to 2.

2. The benzylamide compound or the salt thereof according to claim 1, wherein $R^4$ is hydrogen, or $C_{1-6}$ alkyl.

3. The benzylamide compound or the salt thereof according to claim 1, wherein $R^7$, $R^8$, $R^9$, $R^{10}$, and $R^{11}$ are identical or different and each represent hydrogen, halogen, nitro, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, substituted or unsubstituted amino, aryl, or heterocyclic.

4. A pesticide composition containing a carrier and a benzylamide compound represented by Formula (1):

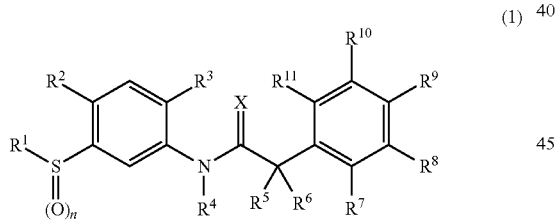

(1)

or the salt thereof, wherein $R^1$ represents $C_{1-6}$ haloalkyl;

$R^2$ and $R^3$ are identical or different and each represent halogen, cyano, or $C_{1-6}$ alkyl;

$R^4$ represents hydrogen, formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkylcarbonyl, $C_{1-6}$ haloalkylcarbonyl, $C_{1-6}$ alkoxycarbonyl, $C_{1-6}$ haloalkoxy carbonyl, arylcarbonyl, aryloxycarbonyl, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, aryl, aryl $C_{1-6}$ alkyl, arylsulfonyl, arylsulfinyl, arylthio, or heterocyclic, all the substituents defined as $R^4$ may optionally be further substituted;

$R^5$ and $R^6$ are identical or different and each represent hydrogen, halogen, $C_{1-6}$ alkyl, or $C_{1-6}$ haloalkyl; $R^5$ and $R^6$, taken together with the carbon atom to which they bond, may bond to each other to form a 3- to 8-membered ring, via or not via at least one heteroatom;

$R^7$, $R^8$, $R^9$, $R^{10}$, and R are identical or different and each represent hydrogen, halogen, nitro, cyano, hydroxyl, formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkylcarbonyl, $C_{1-6}$ haloalkylcarbonyl, arylcarbonyl, aryloxycarbonyl, $C_{1-6}$ alkoxycarbonyl, $C_{1-6}$ haloalkoxycarbonyl, $C_{1-6}$ cyanoalkyl, $C_{1-6}$ cyanoalkoxy, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, $C_{3-8}$ cycloalkylsulfonyl, $C_{3-8}$ cycloalkylsulfinyl, $C_{3-8}$ cycloalkylthio, $C_{3-8}$ cycloalkyl $C_{1-6}$ alkylsulfonyl, $C_{3-8}$ cycloalkyl $C_{1-6}$ alkylsulfinyl, $C_{3-8}$ cycloalkyl $C_{1-6}$ alkylthio, $C_{1-6}$ alkoxy $C_{1-6}$ alkylsulfonyl, $C_{1-6}$ alkoxy $C_{1-6}$ alkylsulfinyl, $C_{1-6}$ alkoxy $C_{1-6}$ alkylthio, $C_{2-6}$ alkenyloxy, $C_{2-6}$ haloalkenyloxy, $C_{2-6}$ alkynyloxy, $C_{2-6}$ haloalkynyloxy, $C_{1-6}$ alkylsulfonyloxy, $C_{1-6}$ haloalkylsulfonyloxy, $C_{1-6}$ alkylsulfinyloxy, $C_{1-6}$ haloalkylsulfinyloxy, carboxyl, OCN, SCN, $SF_5$, substituted or unsubstituted amino, aryl, aryl $C_{1-6}$ alkyl, aryloxy, aryl $C_{1-6}$ alkoxy, arylsulfonyl, arylsulfinyl, arylthio, aryl $C_{1-6}$ alkylsulfonyl, aryl $C_{1-6}$ alkylsulfinyl, aryl $C_{1-6}$ alkylthio, heterocyclic, heterocyclic $C_{1-6}$ alkyl, or heterocyclic oxy, all of which may optionally be further substituted;

$R^7$ and $R^8$, $R^8$ and $R^9$, $R^9$ and $R^{10}$, or $R^{10}$ and $R^{11}$, taken together with the benzene ring to which they bond, may bond to each other to form a 3- to 8-membered ring via or not via at least one heteroatom;

X represents oxygen or sulfur; and n represents an integer of 0 to 2.

5. A miticide composition containing a carrier and a benzylamide compound represented by Formula (1):

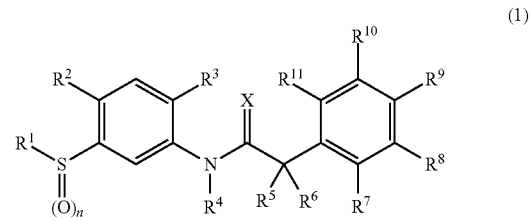

(1)

or the salt thereof, wherein $R^1$ represents $C_{1-6}$ haloalkyl;

$R^2$ and $R^3$ are identical or different and each represent halogen, cyano, or $C_{1-6}$ alkyl;

$R^4$ represents hydrogen, formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkylcarbonyl, $C_{1-6}$ haloalkylcarbonyl, $C_{1-6}$ alkoxycarbonyl, $C_{1-6}$ haloalkoxy carbonyl, arylcarbonyl, aryloxycarbonyl, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, aryl, aryl $C_{1-6}$ alkyl, arylsulfonyl, arylsulfinyl, arylthio, or heterocyclic, all the substituents defined as $R^4$ may optionally be further substituted;

$R^5$ and $R^6$ are identical or different and each represent hydrogen, halogen, $C_{1-6}$ alkyl, or $C_{1-6}$ haloalkyl; $R^5$ and $R^6$, taken together with the carbon atom to which they bond, may bond to each other to form a 3- to 8-membered ring, via or not via at least one heteroatom;

$R^7$, $R^8$, $R^9$, $R^{10}$, and R are identical or different and each represent hydrogen, halogen, nitro, cyano, hydroxyl, formyl, $C_{1-6}$ alkyl, $C_{1-6}$ haloalkyl, $C_{1-6}$ alkoxy, $C_{1-6}$ haloalkoxy, $C_{1-6}$ alkoxy $C_{1-6}$ alkyl, $C_{1-6}$ haloalkoxy $C_{1-6}$ alkyl, $C_{3-8}$ cycloalkyl, $C_{3-8}$ cycloalkyl $C_{1-6}$ alkyl, $C_{1-6}$ alkylcarbonyl, $C_{1-6}$ haloalkylcarbonyl, arylcarbonyl, aryloxycarbonyl, $C_{1-6}$ alkoxycarbonyl, $C_{1-6}$ haloalkoxycarbonyl, $C_{1-6}$ cyanoalkyl, $C_{1-6}$ cyanoalkoxy, $C_{2-6}$ alkenyl, $C_{2-6}$ haloalkenyl, $C_{2-6}$ alkynyl, $C_{2-6}$ haloalkynyl, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, $C_{3-8}$ cycloalkylsulfonyl, $C_{3-8}$ cycloalkylsulfinyl, $C_{3-8}$ cycloalkylthio, $C_{3-8}$ cycloalkyl $C_{1-6}$ alkylsulfonyl, $C_{3-8}$ cycloalkyl $C_{1-6}$ alkylsulfinyl, $C_{3-8}$ cycloalkyl $C_{1-6}$ alkylthio, $C_{1-6}$ alkoxy $C_{1-6}$ alkylsulfonyl, $C_{1-6}$ alkoxy $C_{1-6}$ alkylsulfinyl, $C_{1-6}$ alkoxy $C_{1-6}$ alkylthio, $C_{2-6}$ alkenyloxy, $C_{2-6}$ haloalkenyloxy, $C_{2-6}$ alkynyloxy, $C_{2-6}$ haloalkynyloxy, $C_{1-6}$ alkylsulfonyloxy, $C_{1-6}$ haloalkylsulfonyloxy, $C_{1-6}$ alkylsulfinyloxy, $C_{1-6}$ haloalkylsulfinyloxy, carboxyl, OCN, SCN, $SF_5$, substituted or unsubstituted amino, aryl, aryl $C_{1-6}$ alkyl, aryloxy, aryl $C_{1-6}$ alkoxy, arylsulfonyl, arylsulfinyl, arylthio, aryl $C_{1-6}$ alkylsulfonyl, aryl $C_{1-6}$ alkylsulfinyl, aryl $C_{1-6}$ alkylthio, heterocyclic, heterocyclic $C_{1-6}$ alkyl, or heterocyclic oxy, all of which may optionally be further substituted;

$R^7$ and $R^8$, $R^8$ and $R^9$, $R^9$ and $R^{10}$, or $R^{10}$ and $R^{11}$, taken together with the benzene ring to which they bond, may bond to each other to form a 3- to 8-membered ring via or not via at least one heteroatom;

X represents oxygen or sulfur; and n represents an integer of 0 to 2 wherein the carrier is a solid carrier, liquid carrier, or gaseous carrier..

6. The pesticide according to claim 4 or the miticide according to claim 5, wherein $R^4$ is hydrogen, or $C_{1-6}$ alkyl.

7. The pesticide according to claim 4 or the miticide according to claim 5, wherein $R^7$, $R^8$, $R^9$, $R^{10}$, and $R^{11}$ are identical or different and each represent hydrogen, halogen, nitro, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ haloalkylsulfonyl, $C_{1-6}$ alkylsulfinyl, $C_{1-6}$ haloalkylsulfinyl, $C_{1-6}$ alkylthio, $C_{1-6}$ haloalkylthio, substituted or unsubstituted amino, aryl, or heterocyclic.

* * * * *

UNITED STATES PATENT AND TRADEMARK OFFICE
CERTIFICATE OF CORRECTION

PATENT NO. : 11,000,037 B2
APPLICATION NO. : 16/318598
DATED : May 11, 2021
INVENTOR(S) : Tetsuya Imai et al.

It is certified that error appears in the above-identified patent and that said Letters Patent is hereby corrected as shown below:

In the Claims

Claim 1, Column 70, Lines 49-50, replace "haloalkoxy carbonyl" with --haloalkoxycarbonyl--

Claim 1, Column 70, Line 62, replace "and R" with --and $R^{11}$--

Claim 4, Column 72, Line 4, replace "and R" with --and $R^{11}$--

Claim 5, Column 72, Lines 58-59, replace "haloalkoxy carbonyl" with --haloalkoxycarbonyl--

Claim 5, Column 73, Line 4, replace "and R" with --and $R^{11}$--

Claim 5, Column 74, Line 11, replace "0 to 2" with --0 to 2,--

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*